(12) United States Patent
Carruthers et al.

(10) Patent No.: US 7,317,025 B2
(45) Date of Patent: Jan. 8, 2008

(54) NON-PEPTIDIC NPY Y2 RECEPTOR INHIBITORS

(75) Inventors: Nicholas I. Carruthers, Poway, CA (US); Wenying Chai, San Diego, CA (US); Scott L. Dax, Landenberg, PA (US); Jill A. Jablonowski, San Diego, CA (US); Xiaobing Li, Flemington, NJ (US); Timothy W. Lovenberg, San Diego, CA (US); William V. Murray, Belle Mead, NJ (US); Dale A. Rudolph, San Diego, CA (US); Mark Seierstad, San Diego, CA (US); Mark A. Youngman, Warminster, PA (US)

(73) Assignee: Johnson & Johnson Pharmaceutical Research & Development, LLC, Raritan, NJ (US)

( * ) Notice: Subject to any disclaimer, the term of this patent is extended or adjusted under 35 U.S.C. 154(b) by 428 days.

(21) Appl. No.: 10/949,055

(22) Filed: Sep. 24, 2004

(65) Prior Publication Data

US 2005/0070534 A1    Mar. 31, 2005

Related U.S. Application Data

(60) Provisional application No. 60/505,462, filed on Sep. 24, 2003.

(51) Int. Cl.
| | |
|---|---|
| *A61K 31/445* | (2006.01) |
| *A61K 31/405* | (2006.01) |
| *C07D 209/00* | (2006.01) |
| *C07D 209/02* | (2006.01) |
| *C07D 209/04* | (2006.01) |
| *C07D 211/00* | (2006.01) |

(52) U.S. Cl. .................. 514/315; 514/320; 514/415; 548/452; 548/465; 548/469; 546/184; 546/196
(58) Field of Classification Search ................ 514/315, 514/320, 415; 548/452, 465, 469; 546/184, 546/196
See application file for complete search history.

(56) References Cited

U.S. PATENT DOCUMENTS

2003/0153553 A1    8/2003    Mattei et al.

FOREIGN PATENT DOCUMENTS

| WO | WO 97/09308 | 3/1997 |
|---|---|---|
| WO | WO 00/17166 | 3/2000 |
| WO | WO 03/032992 | 4/2003 |

OTHER PUBLICATIONS

Peakdale Molecular Catalog page for ID# PFC-0817, N-(1-acetyl-2,3-dihydro-1H-indol-6-yl)-N-(1-benzyl-piperidin-4-yl)-3-phenyl-acrylamide.*

PCT International Search Report, dated Jan. 19, 2005, for PCT Int'l. Appln. No. PCT/US2004/031378.
Doods, Henri et al., "BIIE0246: A selective and high affinity neuropeptide Y Y2 receptor antagonist", European Journal of Pharmacology, Amsterdam, Netherlands, vol. 384, No. 2-3, Nov. 19, 1999, pp. R3-R5.
Grouzmann Eric et al., "Characterization of a selective antagonist of neuropeptide Y at the Y2 receptor. Synthesis and Pharmacological evaluation of a Y2 antagonist", Journal of Biological Chemistry, American Society of Biological Chemists, Baltimore, Maryland, US, vol. 272, No. 12, Mar. 21, 1997, pp. 7699-7706.
Jablonowski, Jill et al., "Novel non-peptidic neuropeptide Y Y2 receptor antagonists", Bioorganic & Medicinal Chemistry Letters, 14(5), 1239-1242.
Andres, C.J. et al. Differentially Functionalized Diamines as Novel Ligands for the NPY2 Receptor. Bioorg. Med. Chem. Lett. 2003, 13(17), 2883-2885.
Baldock, P.A. Hypothalamic Y2 Receptors Regulate Bone Formation. J. Clin. Invest. 2002, 109(7), 915-921.
Batterham, R.L. et al. Gut Hormone PYY(3-36) Physiologically Inhibits Food Intake. Nature 2002, 418(6898), 650-654.
Blomqvist, A.G. and H. Herzog. Y-Receptor Subtypes—How Many More? Trends Neurosci. 1997, 20(7), 294-298.
Bonaventure, P. et al. Characterization of N-(1-Acetyl-2,3-dihydro-1H-indol-6-yl)-3-(3-cyano-phenyl)-N-[1-(2-cyclopentyl-ethyl)-piperidin-4-yl]-acrylamide (JNJ-5207787), a Small Molecule Antagonist of the Neuropeptide Y Y2 Receptor. J. Pharmacol. Exp. Ther. 2004, 308(3), 1130-1137.
Clark, J.T. et al. Neuropeptide Y and Human Pancreatic Polypeptide Stimulate Feeding Behavior in Rats. Endocrinology 1984, 115(1), 427-429.
Flood, J.F. et al. Modulation of Memory Processing by Neuropeptide Y. Brain Res. 1987, 421(1-2), 280-290.
Heilig, M. et al. Antidepressant Drugs Increase the Concentration of Neuropeptide Y (NPY)-like Immunoreactivity in the Rat Brain. Eur. J. Pharmacol. 1988, 147(3), 465-467.
Heilig, M. et al. Centrally Administered Neuropeptide Y (NPY) Produces Anxiolytic-like Effects in Animal Anxiety Models. Psychopharmacology 1989, 98(4), 524-529.
Heilig, M. et al. Anxiolytic-Like Effect of Neuropeptide Y (NPY), but Not Other Peptides in an Operant Conflict Test. Regul. Pept. 1992, 41(1), 61-69.
Heilig, M. et al. Anxiolytic-Like Action of Neuropeptide Y: Mediation by Y1 Receptors in Amygdala, and Dissociation from Food Intake Effects. Neuropsychopharmacology 1993, 8(4), 357-363.
Herzog, H. Hypothalamic Y2 Receptors: Central Coordination of Energy Homeostasis and Bone Mass Regulation. Drug News Perspect. 2002, 15(8), 506-510.

(Continued)

*Primary Examiner*—Kamal A. Saeed
*Assistant Examiner*—Susannah Chung

(57) ABSTRACT

The invention provides novel non-peptidic NPY Y2 receptor inhibitors useful in treating or preventing: anxiolytic disorders or depression; injured mammalian nerve tissue; conditions responsive to treatment through administration of a neurotrophic factor; neurological disorders; bone loss; substance related disorders; obesity; or an obesity-related disorder. Compounds of the invention are also useful in modulating endocrine functions, particularly endocrine functions controlled by the pituitary and hypothalamic glands, and are therefore useful in the treatment or prevention of inovulation and infertility.

10 Claims, No Drawings

OTHER PUBLICATIONS

Kalra, S.P. and W.R. Crowley, Neuropeptide Y: A Novel Neuroendocrine Peptide in the Control of Pituitary Hormone Secretion, and its Relation to Luteinizing Hormone. Front. Neuroendrocrinol. 1992, 13(1), 1-46.

Levine, A.S. et al. Neuropeptide Y: A Potent Inducer of Consummatory Behavior in Rats. Peptides 1984, 5(6), 1025-1029.

Morris, M.J. et al. Increases in Plasma Neuropeptide Y Concentrations During Sympathetic Activation in Man. J. Auton. Nerv. Syst. 1986, 17(2), 143-149.

Naveilhan, P. et al. Normal Feeding Behavior, Body Weight and Leptin Response Require the Neuropeptide Y Y2 Receptor. Nature Med. 1999, 5(10), 1188-1193.

Rimondini, R. et al. Suppression of Ethanol Self-administration by the Neuropeptide Y (NPY) Y2 Receptor Antagonist BIIE0246: Evidence for the Sensitization in Rats with a History of Dependence. Neurosci. Lett. 2005, 375(2), 129-133.

Stanley, B.G. and S.F. Liebowitz. Neuropeptide Y: Stimulation of Feeding and Drinking by Injection into the Paraventricular Nucleus. Life Sci. 1984, 35(26), 2635-2642.

Stanley, B.G. and S.F. Liebowitz. Neuropeptide Y Injected in the Paraventricular Hypothalamus: A Powerful Stimulant of Feeding Behavior. Proc. Nat. Acad. Sci. U.S.A. 1985, 82(11), 3940-3943.

Thiele, T.E. et al. Ethanol Consumption and Resistance are Inversely Related to Neuropeptide Y Levels. Nature 1998, 396(6709), 366-369.

Thiele, T.E. and N.E. Badia-Elder. A Role for Neuropeptide Y in Alcohol Intake Control: Evidence from Human and Animal Research. Physiol. Behav. 2003, 79(1), 95-101.

Thiele, T.E. et al. Alcoholism and Obesity: Overlapping Neuropeptide Pathways? Neuropeptides 2003, 37(6), 321-337.

Thiele, T.E. et al. Assessment of Ethanol Consumption and Water Drinking by NPY Y2 Receptor Knockout Mice. Peptides 2004, 25(6), 975-983.

Thiele, T.E. et al. A Role for Neuropeptide Y in Neurobiological Responses to Ethanol and Drugs of Abuse. Neuropeptides 2004, 38(4), 235-243.

Thorsell, A. et al. Blockade of Central Neuropeptide Y (NPY) Y2 Receptors Reduces Ethanol Self-Administration in Rats. Neurosci. Lett. 2002, 332(1), 1-4.

Widdowson, P.S. et al. Reduced Neuropeptide Y Concentrations in Suicide Brain. J. Neurochem. 1992, 59(1), 73-80.

Peakdale Molecular Catalog page for ID# PFC-0817 (N-(1-Acetyl-2,3-dihydro-1H-indol-6-yl)-N-(1-benzyl-piperidin-4-yl)-3-phenyl-acrylamide).

* cited by examiner

NON-PEPTIDIC NPY Y2 RECEPTOR INHIBITORS

This application claims priority to provisional application, which is U.S. Ser. No. 60/505,462 filed Sep. 24, 2003. The complete disclosures of the aforementioned related U.S. patent application is hereby incorporated herein by reference for all purposes.

FIELD OF THE INVENTION

The invention provides novel non-peptidic NPY Y2 receptor inhibitors useful in treating or preventing: anxiolytic disorders and depression; injured mammalian nerve tissue; a condition responsive to treatment through administration of a neurotrophic factor; a neurological disorder; bone loss; substance related disorders; obesity; or an obesity-related disorder. Compounds of the invention are also useful in modulating endocrine functions; particularly endocrine functions controlled by the pituitary and hypothalamic glands, and may be used to treat inovulation and infertility.

BACKGROUND OF THE INVENTION

Regulation and function of the mammalian central nervous system is governed by a series of interdependent receptors, neurons, neurotransmitters, and proteins. The neurons play a vital role in this system, for when externally or internally stimulated, they react by releasing neurotransmitters that bind to specific proteins. Common examples of endogenous small molecule neurotransmitters such as acetylcholine, adrenaline, norepinephrine, dopamine, serotonin, glutamate, and gamma-aminobutyric acid are well known, as are the specific receptors that recognize these compounds as ligands ("The Biochemical Basis of Neuropharmacology", Sixth Edition, Cooper, J. R.; Bloom, F. E.; Roth, R. H. Eds., Oxford University Press, New York, N.Y. 1991).

In addition to the endogenous small molecule neurotransmitters, there is increasing evidence that neuropeptides play an integral role in neuronal operations. Neuropeptides are now believed to be co-localized with perhaps more than one-half of the 100 billion neurons of the human central nervous system. In addition to being found in humans, neuropeptides have been discovered in a number of animal species. In some instances, the composition of these peptides is remarkably homogenous among species. This finding suggests that the function of neuropeptides is vital and has been impervious to evolutionary changes. Furthermore, neuropeptides, unlike small molecule neurotransmitters, are typically synthesized by the neuronal ribosome. In some cases, the active neuropeptides are produced as part of a larger protein that is enzymatically processed to yield the active substance. Based upon these differences, compared to small molecule neurotransmitters, neuropeptide-based strategies may offer novel therapies for the treatment of CNS diseases and disorders. Specifically, agents that affect the binding of neuropeptides to their respective receptors or ameliorate responses that are mediated by neuropeptides are potential therapies for diseases associated with neuropeptides.

There are a number of afflictions that are associated with the complex interdependent system of receptors and ligands within the central nervous system; these include neurodegenerative diseases, affective disorders such as anxiety, depression, pain and schizophrenia, and affective conditions that include a metabolic component, namely obesity. Such conditions, disorders, and diseases have been treated with small molecules and peptides that modulate neuronal responses to endogenous neurotransmitters.

One example of this class of neuropeptides is neuropeptide Y (NPY). NPY was first isolated from porcine brain (Tatemoto, K. et al. Nature 1982, 296, 659) and was shown to be structurally similar to other members of the pancreatic polypeptide (PP) family such as peptide YY, which is primarily synthesized by endocrine cells in the gut, and pancreatic polypeptide, which is synthesized by the pancreas. NPY is a single peptide protein that consists of thirty-six amino acids containing an amidated C-terminus. Like other members of the pancreatic polypeptide family, NPY has a distinctive conformation that consists of an N-terminal polyproline helical region and an amphiphilic alpha-helix joined by a characteristic PP-fold (Vladimir, S. et al. Biochemistry 1990, 20, 4509). Furthermore, NPY sequences from a number of animal species have been elucidated and all show a high degree of amino acid homology to the human protein (more than 94% in rat, dog, rabbit, pig, cow, sheep) (see Larhammar, D. in "The Biology of Neuropeptide Y and Related Peptides", Colmers, W. F. and Wahlestedt, C. Eds., Humana Press, Totowa, N.J. 1993).

Endogenous receptor proteins that bind NPY and related peptides as ligands have been identified and distinguished, and several such proteins have been cloned and expressed. Six different receptor subtypes [Y1, Y2, Y3, Y4(PP), Y5, Y6 (formerly designated as a Y5 receptor)] are recognized today based upon binding profile, pharmacology, and/or composition if identity is known (Wahlestedt, C. et al. Ann. N.Y. Acad. Sci. 1990, 611, 7; Larhammar, D. et al. J. Biol. Chem. 1992, 267, 10935; Wahlestedt, C. et al. Regul. Pept. 1986, 13, 307; Fuhlendorff, J. U. et al. Proc. Natl. Acad. Sci. U.S.A. 1990, 87, 182; Grundemar, L. et al. J. Pharmacol. Exp. Ther. 1991, 258, 633; Laburthe, M. et al. Endocrinology 1986, 118, 1910; Castan, I. et al. Endocrinology 1992, 131, 1970; Gerald, C. et al. Nature 1996, 382, 168; Weinberg, D. H. et al. J. Biol. Chem. 1996, 271, 16435; Gehlert, D. et al. Curr. Pharm. Des. 1995, 1, 295; Lundberg, J. M. et al. Trends in Pharmacological Sciences 1996, 17, 301). Most and perhaps all NPY receptor proteins belong to the family of so-called G-protein coupled receptors (GPCRs). The neuropeptide Y5 receptor, a putative GPCR, is negatively coupled to cellular cyclic adenosine monophosphate (cAMP) levels via the action of adenylate cyclase (Gerald, C. et al. Nature 1996, 382, 168; Gerald, C. et al. PCT WO 96/16542). For example, NPY inhibits forskolin-stimulated cAMP production/levels in a neuroblastoma cell line. A Y5 ligand that mimics NPY in this fashion is an agonist whereas one that competitively reverses the NPY inhibition of forskolin-stimulated cAMP production is an antagonist.

The neuropeptide Y2 receptor has high affinity for NPY and PYY, but unlike the Y1 receptor, is relatively resistant to the effect of the N-terminal deletion and retains a high binding affinity for the C-terminal fragments such as $NPY_{13-36}$ (Blomqvist, A. G. et al. Trends Neurosci. 1997, 20, 294-298).

NPY itself is the archetypal substrate for the NPY receptors and its binding can elicit a variety of pharmacological and biological effects in vitro and in vivo. When administered to the brain of live animals (intracerebroventricularly (icv) or into the amygdala), NPY produces anxiolytic effects in established animal models of anxiety such as the elevated plus-maze, Vogel punished drinking, and Geller-Seifter's bar-pressing conflict paradigms (Heilig, M. et al. Psychopharmacology 1989, 98, 524; Heilig, M. et al. Regul. Pept. 1992, 41, 61; Heilig, M. et al. Neuropsychopharmacology 1993, 8, 357). Thus, compounds that mimic NPY are postulated to be useful for the treatment of anxiolytic disorders.

The immunoreactivity of NPY is notably decreased in the cerebrospinal fluid of patients with major depression and those of suicide victims (Widdowson, P. S. et al. J. Neurochem. 1992, 59, 73), and rats treated with tricyclic antidepressants display significant increases of NPY relative to a control group (Heilig, M. et al. Eur. J. Pharmacol. 1988, 147, 465). These findings suggest that an inadequate NPY response may play a role in some depressive illnesses, and that compounds that regulate the NPY-ergic system may be useful for the treatment of depression.

NPY improves memory and performance scores in animal models of learning (Flood, J. F. et al. Brain Res. 1987, 421, 280) and therefore may serve as a cognition enhancer for the treatment of neurodegenerative diseases such as Alzheimer's Disease (AD) as well as AIDS-related and senile dementia.

Elevated plasma levels of NPY are present in animals and humans experiencing episodes of high sympathetic nerve activity such as surgery, newborn delivery and hemorrhage (Morris, M. J. et. al. J. Auton. Nerv. Syst. 1986, 17, 143). Thus, chemical substances that alter the NPY-ergic system may be useful for alleviating migraine, pain, and the condition of stress.

NPY also mediates endocrine functions such as the release of luteinizing hormone (LH) in rodents (Kalra, S. P. et. al. Front. Neuroendrocrinol. 1992, 13, 1). Since LH is vital for mammalian ovulation, a compound that mimics the action of NPY could be useful for the treatment of infertility, particularly in women with so-called luteal phase defects.

NPY is a powerful stimulant of food intake; as little as one-billionth of a gram, when injected directly into the CNS, causes satiated rats to overeat (Clark, J. T. et al. Endocrinology 1984, 115, 427; Levine, A. S. et al. Peptides 1984, 5, 1025; Stanley, B. G. et al. Life Sci. 1984, 35, 2635; Stanley, B. G. et al. Proc. Nat. Acad. Sci. U.S.A. 1985, 82, 3940). Thus NPY is orexigenic in rodents but not anxiogenic when given intracerebroventricularly and so antagonism of neuropeptide receptors may be useful for the treatment of diabetes and eating disorders such as obesity, anorexia nervosa, and bulimia nervosa.

It is known that the anxiolytic properties of NPY are mediated through postsynaptic Y1 receptors, whereas presynaptic Y2 receptors negatively control the release of NPY and other cotransmitters (e.g. GABA). Consequently, antagonism of the Y2 receptor may lead to enhanced GABAergic and NPYergic effects and Y2 receptor antagonists should prove useful in the treatment of depression and anxiety.

Recently, a key role of presynaptic hypothalamic Y2 receptor has been suggested in central coordination of energy homeostasis and bone mass regulation (Herzog, H. et al. Drug News & Perspectives 2002, 15, 506-510). Studies analyzing Y2 receptor knockout mice have started to unravel some of the individual functions of this receptor subtype. Y2 receptor knockout mice do show a reduced body weight despite an increase in food intake, which is possibly due to the lack of the feedback inhibition of the postprandially released $PYY_{3-36}$ (Batterham, R. L. et al. Nature 2002, 418, 650-654). The Y2 receptor knockout mice also show a significant increase in bone formation (Baldock, P. A. J. Clin. Invest. 2002, 109, 915-921). Specific deletion of the Y2 receptor in the hypothalamus in adult conditional Y2 receptor knockout mice also causes an increase in bone formation.

Grouzmann and coworkers described a peptide-based ligand, T4-[NPY 33-36], which showed considerable affinity ($IC_{50}$=67 nM) for the NPY Y2 receptor (Grouzmann, E., et al. J. Biol. Chem. 1997, 272, 7699-7706). BIIE0246 also binds to the NYP Y2 receptor with significant affinity ($IC_{50}$=3.3 nM) (Doods, H., et al. Eur. J. Pharmacol. 1999, 384, R3-R5). However, the therapeutic potential for these compounds is limited due to their peptide-like composition and elevated molecular weight.

Studies also indicate that NPY Y2 is involved in the neurobiological responses to ethanol and other drugs of abuse. Thiele and coworkers (Neuropeptides, 2004, 38(4), 235-243; Peptides 2004, 25(6), 975-983) described the low ethanol consumption of Y2 receptor knockout mice, as well as their increased voluntary water consumption. Therefore, modulators of NPY Y2 may allow for the treatment of alcohol and drug abuse.

Accordingly, it is an object of the present invention to provide novel non-peptidic NPY Y2 receptor inhibitors that are useful in modulating or treating: anxiolytic disorders and depression; a condition requiring treatment of injured mammalian nerve tissue; a condition amenable to treatment through administration of a neurotrophic factor; a neurological disorder; bone loss; substance related disorders; obesity; an obesity-related disorder; and a condition related to an endocrine function including inovulation and infertility.

SUMMARY OF THE INVENTION

The invention provides novel non-peptidic NPY Y2 receptor inhibitors of the formula (I):

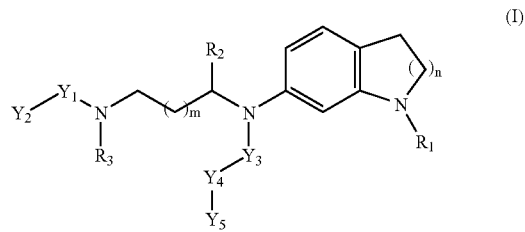

wherein
the fused pyrrolidine ring optionally contains a single carbon-carbon double bond or a single carbon ring member adjacent to the nitrogen is optionally =O substituted;
n is 1 or 2;
m is 0, 1, or 2;
$Y_1$ is a $C_{0-5}$ alkylene, $C_{0-5}$ alkenylene, $C_{0-5}$ alkynylene, $C_{0-5}$acylene; —CH(CONR$^f$R$^9$)— (where R$^f$ and R$^9$ are independently H or $C_{1-4}$alkyl), or —CH(CO$_2$C$_{1-4}$alkyl)-;
$Y_2$ is H, phenyl, $C_{4-8}$ cycloalkyl or $C_{4-8}$ cycloalkenyl, each ring optionally substituted with R$^q$;
$Y_3$ is —CH$_2$—, carbonyl or sulfone;
$Y_4$ is a substituted or unsubstituted $C_{2-7}$ alkyl, $C_{2-7}$ alkenyl, $C_{2-7}$ alkynyl or $C_{3-7}$cycloalkyl;
$Y_5$ is phenyl, furanyl, thiophenyl, pyrrolyl, pyrrolinyl, pyrrolidinyl, dioxolanyl, oxazolyl, thiazolyl, imidazolyl, imidazolidinyl, pyrazolyl, pyrazolinyl, pyrazolidinyl, oxadiazolyl, triazolyl, thiadiazolyl, pyranyl, pyridyl, piperidinyl, dioxanyl, morpholinyl, dithianyl, thiomorpholinyl, pyridazinyl, pyrimidinyl, pyrazinyl, piperazinyl, naphthalenyl, quinolonyli purinyl, indolyl, benzofuranyl, or benzothiophenyl, each optionally mono-, di- or tri-substituted with R$^q$;

$R_1$ is H or is

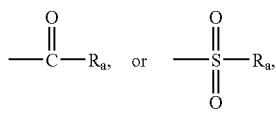

where $R_a$ is H, a substituted or unsubstituted $C_{1-5}$ alkyl, $C_{1-5}$ alkenyl, $C_{1-5}$ alkynyl or $C_{1-5}$ acyl, where the substituent is $C_{1-4}$alkoxy or one or more fluoro;

$R_2$ and $R_3$ are independently selected from H, a substituted or unsubstituted $C_{1-5}$ alkyl, $C_{1-5}$ alkenyl, or $C_{1-5}$ alkynyl, or $R_2$ and $R_3$ may be taken together with the nitrogen of $R_3$ attachment to form piperidine or pyrrolidine or azepine; and $R^q$ is selected from the group consisting of —OH, —$C_{1-6}$ alkyl, —$OC_{1-6}$ alkyl, Ph—, —OPh, benzyl, —Obenzyl, —$C_{3-6}$ cycloalkyl, —$OC_{3-6}$ cycloalkyl, —CN, —$NO_2$, —$N(R^y)R^z$ (wherein $R^y$ and $R^z$ are independently selected from H, $C_{1-6}$ alkyl, $C_{1-6}$ alkenyl, or $R^y$ and $R^z$ may be taken together with the nitrogen of attachment to form an otherwise aliphatic hydrocarbon ring, said ring having 4 to 7 members, optionally having one carbon replaced with O, =N—, NH or $N(C_{1-4}alkyl)$, optionally having one carbon substituted with —OH, and optionally having one or two unsaturated bonds in the ring), —(C=O)N($R^y$)$R^z$, —(N—$R^t$)$COR^t$, —(N—$R^t$)$SO_2C_{1-6}$alkyl (wherein $R^t$ is H or $C_{1-6}$alkyl or two $R^t$ in the same substituent may be taken together with the amide of attachment to form an otherwise aliphatic hydrocarbon ring, said ring having 4 to 6 members), —(C=O)$C_{1-6}$alkyl, —(S=O)$_n$—$C_{1-6}$ alkyl (wherein n is selected from 0, 1 or 2), —$SO_2N(R^y)$$R^z$, —$SCF_3$, halo, —$CF_3$, —$OCF_3$, —COOH and —$COOC_{1-6}$alkyl;

and enantiomers, diastereomers, hydrates, solvates and pharmaceutically acceptable salts, esters and amides thereof.

The invention also features pharmaceutical compositions containing such compounds and methods of using such compositions in the treatment or prevention of disease states mediated by NPY Y2 receptor activity.

These and additional aspects of the invention are disclosed in the following detailed description.

DETAILED DESCRIPTION OF THE INVENTION

In a preferred embodiment, the invention provides compounds of formula (I) that have the formula (II):

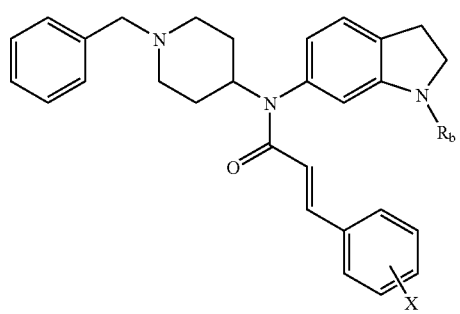

(II)

where $R_b$ is H, $COCH_3$, CHO, $COCH_2COCH_3$, $COCO_2C_2H_5$, $CH_3$, $SO_2CH_3$, or $COCF_3$ and X is 4-$CF_3$, 3-$CF_3$, 2-$CF_3$, 3-Br, 3-F, 3-Cl, 3-$CH_3$, 3-$NO_2$, 3-CN, 3-$SOCF_3$, 3,5-diF, 3,5-di$CH_3$, 3,5-diCl, or 4-Cl.

In another preferred embodiment, the invention provides compounds of formula (I) that have the formula (III):

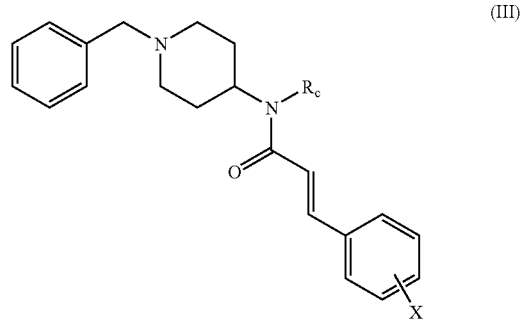

(III)

where $R_c$ is N-(1-acetyl)-tetrahydroquinolin-7-yl, 2-oxo-2,3-dihydro-1H-indol-6-yl, or N-(1-acetyl)-1H-indol-6-yl and X is 4-$CF_3$, 3-$CF_3$, 2-$CF_3$, 3-Br, 3-F, 3-Cl, 3-$CH_3$, 3-$NO_2$, 3-CN, 3-$SOCF_3$, 3,5-diF, 3,5-di$CH_3$, 3,5-diCl, or 4-Cl.

In another preferred embodiment, the invention provides compounds of formula (I) that have the formula (IV):

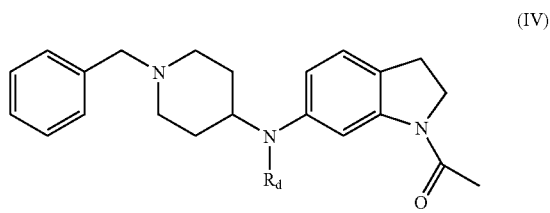

(IV)

where $R_d$ is $COCH_2CH_2C_6H_4X$, $CO(C_3H_4)C_6H_4X$, E-$CH_2CH=CHC_6H_4X$, E-$SO_2CH=CHC_6H_4X$, $COC\equiv CC_6H_4X$, Z—$COCH=CHC_6H_4X$, (E,E)—CO$(CH=CH)_2C_6H_5$, $CH=CH_2$, E-$COCH=CH$(3-thiophenyl)X, E—$COCH=CH$(pyridyl)X, E-$COCH=CH$(1-hydroxypyridyl), or E-$COCH=CH$(2-imidazolyl)X and X is 4-$CF_3$, 3-$CF_3$, 2-$CF_3$, 3-Br, 3-F, 3-Cl, 3-$CH_3$, 3-$NO_2$, 3-CN, 3-$SOCF_3$, 3,5-diF, 3,5-di$CH_3$, 3,5-diCl, or 4-Cl.

In another preferred embodiment, the invention provides compounds of formula (I) that have the formula (V):

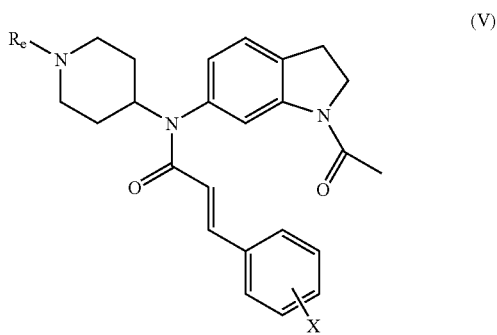

(V)

where $R_e$ is $COC_6H_5$, $CH_2CH_2C_6H_5$, $CH_2CH_2CH_2C_6H_5$, $CH(CO_2CH_3)C_6H_5$, $CH(CONHCH_2CH_3)C_6H_5$, $CH_2C_6H_{11}$, $CH_2CH_2C_6H_{11}$, or $CH_2CH_2C_5H_9$, and X is 4-$CF_3$, 3-$CF_3$, 2-$CF_3$, 3-Br, 3-F, 3-Cl, 3-$CH_3$, 3-$NO_2$, 3-CN, 3-$SOCF_3$, 3,5-diF, 3,5-di$CH_3$, 3,5-diCl, or 4-Cl.

In another preferred embodiment, the invention provides compounds of formula (I) that have the formula (VI):

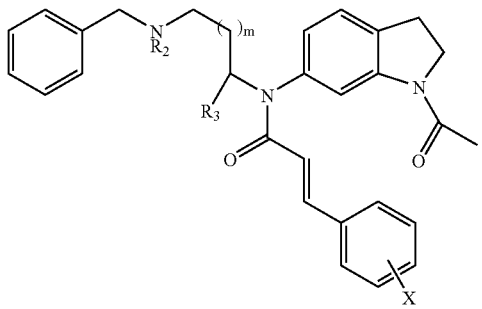

where $R_2$ is H, $C_{1-3}$alkyl, or allyl and $R_3$ is H, or $R_2$ and $R_3$ are taken together to be a divalent moiety —$CH_2$—, m is 1 or 2, and X is 4-$CF_3$, 3-$CF_3$, 2-$CF_3$, 3-Br, 3-F, 3-Cl, 3-$CH_3$, 3-$NO_2$, 3-CN, 3-$SOCF_3$, 3,5-diF, 3,5-di$CH_3$, 3,5-diCl, or 4-Cl.

Preferred compounds of the present invention are selected from the group consisting of:

| EX | CHEMICAL NAME |
|---|---|
| 1 | trans-N-(1-Acetyl-2,3-dihydro-1H-indol-6-yl)-N-(1-benzyl-piperidin-4-yl)-3-phenyl-acrylamide; |
| 2 | trans-N-(1-Benzyl-piperidin-4-yl)-N-(2,3-dihydro-1H-indol-6-yl)-3-phenyl-acrylamide; |
| 3 | trans-N-(1-Benzyl-piperidin-4-yl)-N-(1-formyl-2,3-dihydro-1H-indol-6-yl)-3-phenyl-acrylamide; |
| 4 | trans-N-(1-Benzyl-piperidin-4-yl)-N-[1-(3-oxo-butyryl)-2,3-dihydro-1H-indol-6-yl]-3-phenyl-acrylamide; |
| 5 | trans-{6-[(1-Benzyl-piperidin-4-yl)-(3-phenyl-acryloyl)-amino]-2,3-dihydro-indol-1-yl}-oxo-acetic acid ethyl ester; |
| 6 | trans-N-(1-Benzyl-piperidin-4-yl)-N-(1-methyl-2,3-dihydro-1H-indol-6-yl)-3-phenyl-acrylamide; |
| 7 | trans-N-(1-Benzyl-piperidin-4-yl)-N-(1-methanesulfonyl-2,3-dihydro-1H-indol-6-yl)-3-phenyl-acrylamide; |
| 8 | trans-N-(1-Benzyl-piperidin-4-yl)-3-phenyl-N-[1-(2,2,2-trifluoro-acetyl)-2,3-dihydro-1H-indol-6-yl]-acrylamide; |
| 9 | trans-N-(1-Acetyl-1,2,3,4-tetrahydro-quinolin-7-yl)-N-(1-benzyl-piperidin-4-yl)-3-phenyl-acrylamide; |
| 10 | trans-N-(1-Benzyl-piperidin-4-yl)-N-(2-oxo-2,3-dihydro-1H-indol-6-yl)-3-phenyl-acrylamide; |
| 11 | trans-N-(1-Acetyl-1H-indol-6-yl)-N-(1-benzyl-piperidin-4-yl)-3-phenyl-acrylamide; |
| 12 | N-(1-Acetyl-2,3-dihydro-1H-indol-6-yl)-N-(1-benzyl-piperidin-4-yl)-3-phenyl-propionamide; |
| 13 | trans-2-Phenyl-cyclopropanecarboxylic acid (1-acetyl-2,3-dihydro-1H-indol-6-yl)-(1-benzyl-piperidin-4-yl)-amide; |
| 14 | trans-1-{6-[(1-Benzyl-piperidin-4-yl)-(3-phenyl-allyl)-amino]-2,3-dihydro-indol-1-yl}-ethanone; |
| 15 | trans-2-Phenyl-ethenesulfonic acid (1-acetyl-2,3-dihydro-1H-indol-6-yl)-(1-benzyl-piperidin-4-yl)-amide; |
| 16 | 3-Phenyl-propynoic acid (1-acetyl-2,3-dihydro-1H-indol-6-yl)-(1-benzyl-piperidin-4-yl)-amide; |
| 17 | cis-N-(1-Acetyl-2,3-dihydro-1H-indol-6-yl)-N-(1-benzyl-piperidin-4-yl)-3-phenyl-acrylamide; |
| 18 | trans,trans-5-Phenyl-penta-2,4-dienoic acid (1-acetyl-2,3-dihydro-1H-indol-6-yl)-(1-benzyl-piperidin-4-yl)-amide; |
| 19 | N-(1-Acetyl-2,3-dihydro-1H-indol-6-yl)-N-(1-benzyl-piperidin-4-yl)-acrylamide; |
| 20 | trans-N-(1-Acetyl-2,3-dihydro-1H-indol-6-yl)-N-(1-benzyl-piperidin-4-yl)-3-thiophen-3-yl-acrylamide; |
| 21 | trans-N-(1-Acetyl-2,3-dihydro-1H-indol-6-yl)-N-(1-benzyl-piperidin-4-yl)-3-pyridin-2-yl-acrylamide; |
| 22 | trans-N-(1-Acetyl-2,3-dihydro-1H-indol-6-yl)-N-(1-benzyl-piperidin-4-yl)-3-pyridin-3-yl-acrylamide; |
| 23 | trans-N-(1-Acetyl-2,3-dihydro-1H-indol-6-yl)-N-(1-benzyl-piperidin-4-yl)-3-pyridin-4-yl-acrylamide; |
| 24 | trans-N-(1-Acetyl-2,3-dihydro-1H-indol-6-yl)-N-(1-benzyl-piperidin-4-yl)-3-(1-oxy-pyridin-4-yl)-acrylamide; |
| 25 | trans-N-(1-Acetyl-2,3-dihydro-1H-indol-6-yl)-N-(1-benzyl-piperidin-4-yl)-3-(1H-imidazol-2-yl)-acrylamide; |
| 26 | trans-N-(1-Acetyl-2,3-dihydro-1H-indol-6-yl)-N-(1-benzyl-piperidin-4-yl)-3-(4-trifluoromethyl-phenyl)-acrylamide; |
| 27 | trans-N-(1-Acetyl-2,3-dihydro-1H-indol-6-yl)-N-(1-benzyl-piperidin-4-yl)-3-(3-trifluoromethyl-phenyl)-acrylamide; |
| 28 | trans-N-(1-Acetyl-2,3-dihydro-1H-indol-6-yl)-N-(1-benzyl-piperidin-4-yl)-3-(2-trifluoromethyl-phenyl)-acrylamide; |
| 29 | trans-N-(1-Acetyl-2,3-dihydro-1H-indol-6-yl)-N-(1-benzyl-piperidin-4-yl)-3-(3-bromo-phenyl)-acrylamide; |
| 30 | trans-N-(1-Acetyl-2,3-dihydro-1H-indol-6-yl)-N-(1-benzyl-piperidin-4-yl)-3-(3-fluoro-phenyl)-acrylamide; |
| 31 | trans-N-(1-Acetyl-2,3-dihydro-1H-indol-6-yl)-N-(1-benzyl-piperidin-4-yl)-3-(3-chloro-phenyl)-acrylamide; |
| 32 | trans-N-(1-Acetyl-2,3-dihydro-1H-indol-6-yl)-N-(1-benzyl-piperidin-4-yl)-3-m-tolyl-acrylamide; |
| 33 | trans-N-(1-Acetyl-2,3-dihydro-1H-indol-6-yl)-N-(1-benzyl-piperidin-4-yl)-3-(3-nitro-phenyl)-acrylamide; |
| 34 | trans-N-(1-Acetyl-2,3-dihydro-1H-indol-6-yl)-N-(1-benzyl-piperidin-4-yl)-3-(3-cyano-phenyl)-acrylamide; |
| 35 | trans-N-(1-Acetyl-2,3-dihydro-1H-indol-6-yl)-N-(1-benzyl-piperidin-4-yl)-3-(3-trifluoromethanesulfinyl-phenyl)-acrylamide; |
| 36 | trans-N-(1-Acetyl-2,3-dihydro-1H-indol-6-yl)-N-(1-benzyl-piperidin-4-yl)-3-(3,5-difluoro-phenyl)-acrylamide; |
| 37 | trans-N-(1-Acetyl-2,3-dihydro-1H-indol-6-yl)-N-(1-benzyl-piperidin-4-yl)-3-(3,5-dimethyl-phenyl)-acrylamide; |
| 38 | trans-N-(1-Acetyl-2,3-dihydro-1H-indol-6-yl)-N-(1-benzyl-piperidin-4-yl)-3-(3,5-dichloro-phenyl)-acrylamide; |
| 39 | trans-N-(1-Acetyl-2,3-dihydro-1H-indol-6-yl)-N-(1-benzoyl-piperidin-4-yl)-3-phenyl-acrylamide; |
| 40 | trans-N-(1-Acetyl-2,3-dihydro-1H-indol-6-yl)-N-(1-phenethyl-piperidin-4-yl)-3-phenyl-acrylamide; |
| 41 | trans-N-(1-Acetyl-2,3-dihydro-1H-indol-6-yl)-3-phenyl-N-[1-(3-phenyl-propyl)-piperidin-4-yl]-acrylamide; |
| 42 | trans-N-(1-Acetyl-2,3-dihydro-1H-indol-6-yl)-N-(1-cyclohexylmethyl-piperidin-4-yl)-3-phenyl-acrylamide; |
| 43 | trans-N-(1-Acetyl-2,3-dihydro-1H-indol-6-yl)-N-[1-(2-cyclohexyl-ethyl)-piperidin-4-yl]-3-phenyl-acrylamide; |
| 44 | trans-N-(1-Acetyl-2,3-dihydro-1H-indol-6-yl)-N-[1-(2-cyclopentyl-ethyl)-piperidin-4-yl]-3-phenyl-acrylamide; |
| 45 | trans-N-(1-Acetyl-2,3-dihydro-1H-indol-6-yl)-N-(1-benzyl-piperidin-3-yl)-3-phenyl-acrylamide; |
| 46 | trans-N-(1-Acetyl-2,3-dihydro-1H-indol-6-yl)-N-(1-benzyl-pyrrolidin-3-yl)-3-phenyl-acrylamide; |
| 47 | trans-N-(1-Acetyl-2,3-dihydro-1H-indol-6-yl)-N-(3-benzylamino-propyl)-3-phenyl-acrylamide; |
| 48 | trans-N-(1-Acetyl-2,3-dihydro-1H-indol-6-yl)-N-[3-(allyl-benzyl-amino)-propyl]-3-phenyl-acrylamide; |
| 49 | trans-N-(1-Acetyl-2,3-dihydro-1H-indol-6-yl)-3-(4-chloro-phenyl)-N-[1-(2-cyclohexyl-ethyl)-piperidin-4-yl]-acrylamide; |
| 50 | trans-N-(1-Acetyl-2,3-dihydro-1H-indol-6-yl)-N-[1-(2-cyclohexyl-ethyl)-piperidin-4-yl]-3-(3-nitro-phenyl)-acrylamide; |
| 51 | trans-N-(1-Acetyl-2,3-dihydro-1H-indol-6-yl)-3-(4-chloro-phenyl)-N-[1-(2-cyclopentyl-ethyl)-piperidin-4-yl]-acrylamide; |
| 52 | trans-N-(1-Acetyl-2,3-dihydro-1H-indol-6-yl)-N-[1-(2-cyclopentyl-ethyl)-piperidin-4-yl]-3-(3-nitro-phenyl)-acrylamide; |
| 53 | trans-N-(1-Acetyl-2,3-dihydro-1H-indol-6-yl)-3-(3-cyano-phenyl)-N-[1-(2-cyclopentyl-ethyl)-piperidin-4-yl]-acrylamide; |
| 54 | trans-N-(1-Acetyl-2,3-dihydro-1H-indol-6-yl)-N-(1-benzyl-piperidin-4-yl)-3-(4-chloro-phenyl)-acrylamide; |
| 55 | trans-{4-[(1-Acetyl-2,3-dihydro-1H-indol-6-yl)-(3-phenyl-acryloyl)-amino]-piperidin-1-yl}-phenyl-acetic acid methyl ester; and |
| 56 | trans-N-(1-Acetyl-2,3-dihydro-1H-indol-6-yl)-N-[1-(ethylcarbamoyl-phenyl-methyl)-piperidin-4-yl]-3-phenyl-acrylamide. |

Although all the compounds of formula (I) are novel for the uses and in the formulations taught herein, not all compounds of formula I are novel as such. The compound of the structure:

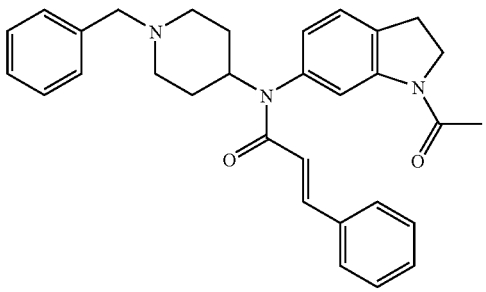

was available from Peakdale Molecular (ID# PRD-0817) prior to the date of the present invention.

The present invention includes the pharmaceutically acceptable acid addition salts of compounds of formula (I). The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, saccharate, ethanesulfonate, benzenesulfonate, and pamoate [i.e., 1,1'-methylene-bis-(2-hydroxy-3 naphthoate)] salts.

The invention also includes base addition salts of formula (I). The chemical bases that may be used as reagents to prepare pharmaceutically acceptable base salts of those compounds of formula (I) that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e, calcium and magnesium), ammonium or water-soluble amine addition salts such as N-methylglucamine (meglumine), and the lower alkanolammonium and other base salts of pharmaceutically acceptable organic amines. See example, S. M. Berge, et al., "Pharmaceutical Salts," J. Pharm. Sci., 1977, 66:1-19, which is incorporated herein by reference.

Representative pharmaceutically acceptable amides of the invention include those derived from ammonia, primary $C_{1-6}$ alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl)amines. Representative pharmaceutically acceptable esters of the invention include $C_{1-7}$alkyl, $C_{5-7}$cycloalkyl, phenyl, and phenyl($C_{1-6}$)alkyl esters. Preferred esters include methyl esters.

The compounds of this invention include all stereoisomers (i.e., cis and trans isomers) and all optical isomers of compounds of the formula (I) (e.g., R and S enantiomers), as well as racemic, diastereomeric and other mixtures of such isomers, as well as all polymorphs of the compounds.

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety.

Representative compounds of the present invention can be synthesized in accordance with the general synthetic methods described below. Since the scheme is an illustration, the invention should not be construed as being limited by the chemical reactions and conditions expressed. The preparation of the various starting materials used in the schemes is well within the skill of persons versed in the art.

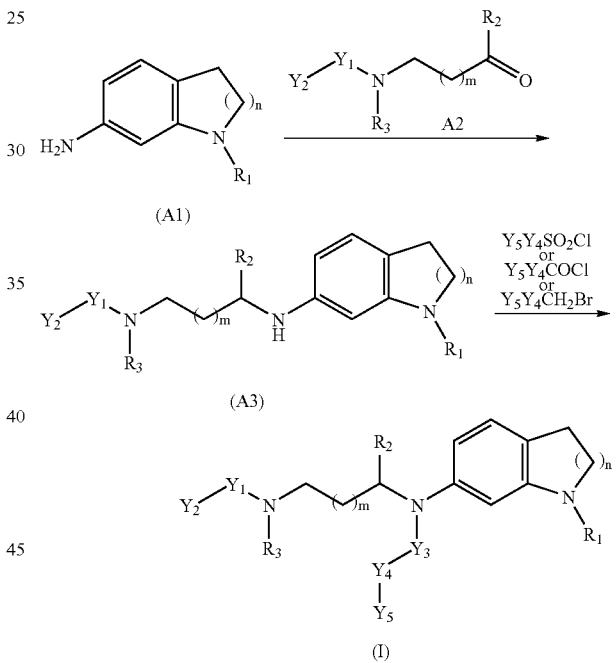

The compounds of formula (I) of the invention may be produced by any number of reaction schemes. Referring to Scheme A, wherein $Y_1$-$Y_5$, $R_{1-3}$, and n are as defined previously, a 1-substituted-6-aminoindoline A1 can be reacted with ketone (A2) under conditions of a reductive amination to form amine (A3). The reaction is typically performed using Na(OAc)$_3$BH as the reducing agent in the presence of AcOH, in a solvent such as CH$_2$Cl$_2$ or 1,2-dichloroethane. The amine (A3) is then reacted with a carboxylic acid under peptide coupling conditions, with a sulfonyl chloride or an acyl chloride in the presence of a suitable base such as triethylamine, or with an alkyl halide, to form derivative (I). Acyl chlorides useful in the transformation can also be prepared from commercially available carboxylic acids using oxalyl chloride and catalytic DMF. Suitable protecting groups are used where appropriate throughout the synthesis.

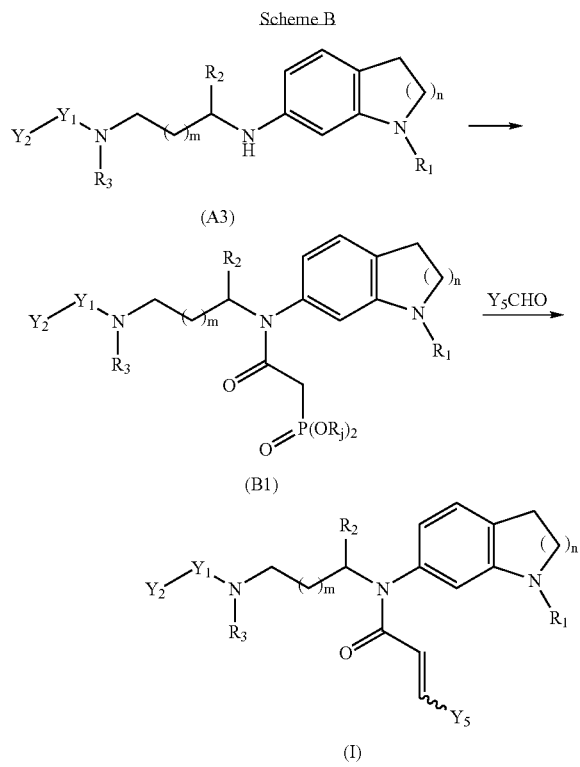

Referring to Scheme B, the compounds of formula (I) may be prepared by an alternate method. Amine (A3) is converted to phosphonate (B1) by reaction with an appropriate phosphonoacetic acid ester. Typically a mixture of amine (A3) and the phosponoacetic acid ester is heated at reflux in a hydrocarbon solvent such as xylenes, with or without the addition of catalytic DMAP. Phosphonate (B1) is then coupled with an appropriate aldehyde to form enamide (I). The cis and trans double bond isomers are independently accessible using this sequence. Suitable conditions for obtaining the trans isomer involve use of the phosphonic acid diethyl ester (B1) in the presence of LiCl and DBU in acetonitrile. The cis isomer can be obtained by reacting the phosphonic acid bis-(2,2,2-trifluoro-ethyl)ester (B1) with a base. such as potassium bis(trimethylsilyl)amide in the presence of a solvating agent such as 18-crown-6.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C., et al., J. Org. Chem. 1978, 43, 2921), thin-layer chromatography, crystallization and distillation.

As used herein, the following terms have the following respective meanings. Other terms that are used to describe the present invention have the same definitions as those generally used by those skilled in the art. Specific examples recited in any definition are not intended to be limiting in any way.

"Hydrocarbon" refers to a substituted or unsubstituted organic compound.

"Acetal" refers to a compound in which two ether oxygens are bound to the same carbon. A "ketal" is an acetal derived from a ketone (a compound of the formula RR'CO, where R and R' are alkyl, aryl, or heterocyclic radicals).

"Acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

"Acyl" means a compound of the formula RCO, where R is aliphatic (characterized by a straight chain of carbon atoms), alicyclic (a saturated hydrocarbon containing at least one ring), or aromatic.

"Alkyl" refers to a fully saturated monovalent hydrocarbon radical containing carbon and hydrogen, which may be a straight chain, branched, or cyclic. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl and cyclohexyl. "Cycloalkyl" groups refer to cyclic alkyl groups such as cyclopropyl, cyclobutyl, cyclopentyl and cyclohexyl. $C_1$-$C_7$ alkyl groups are preferably used in the present invention.

"Substituted alkyl" refers to alkyls as just described which include one or more functional groups such an alkyl containing from 1 to 6 carbon atoms, preferably a lower alkyl containing 1-3 carbon atoms, aryl, substituted aryl, acyl, halogen (i.e., alkyl halos, e.g., $CF_3$), hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like. The term "substituted cycloalkyl" has essentially the same definition as and is subsumed under the term "substituted alkyl" for purposes of describing the present invention. An "alkyl phenone" is an aromatic ketone bound to an alkyl; an "alkenyl phenone is an aromatic ketone bound to an alkylene.

"Amine" refers to substituted or unsubstituted aliphatic amines (e.g., ethyl amine), aromatic amines (e.g., aniline), saturated heterocyclic amines (e.g., piperidine), substituted derivatives such as an alkyl morpholine, aromatic heterocyclic compounds including but not limited to pyridine, purine, or indoline.

"Aralkyl" refers to an alkyl group with an aryl substituent, and the term "aralkylene" refers to an alkenyl group with an aryl substituent; the term "alkaryl" refers to an aryl group that has an alkyl substituent, and the term "alkarylene" refers to an arylene group with an alkyl substituent.

"Alkenyl" refers to a branched or unbranched hydrocarbon group typically although not necessarily containing 2 to about 24 carbon atoms and at least one double bond, such as ethenyl, n-propenyl, isopropenyl, n-butenyl, isobutenyl, octenyl, decenyl, and the like. Generally, though not necessarily, alkenyl groups herein contain 2 to about 12 carbon atoms. The term "lower alkenyl" intends an alkenyl group of two to six carbon atoms, preferably two to four carbon atoms.

"Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

"Aryl" refers to a substituted or unsubstituted monovalent aromatic radical having a single ring (e.g., phenyl) or multiple condensed rings (e.g., naphthyl). Other examples include heterocyclic aromatic ring groups having one or more nitrogen, oxygen, or sulfur atoms in the ring, such as imidazolyl, furyl, pyrrolyl, pyridyl, thienyl and indolyl, among others. The term "arylene" refers to the diradical derived from aryl (including substituted aryl) as exemplified by 1,2-phenylene, 1,3-phenylene, 1,4-phenylene, 1,2-naphthylene and the like.

"Substituted aryl" refers to an aryl as just described that contains one or more functional groups such as lower alkyl, acyl, aryl, halogen, alkylhalos (e.g., $CF_3$), hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like.

"Alkynyl" as used herein refers to a branched or unbranched hydrocarbon group typically although not necessarily containing 2 to about 24 carbon atoms and at least one triple bond, such as ethynyl, n-propynyl, isopropynyl, n-butynyl, isobutynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

"Alkoxy" as used herein refers to an alkyl group bound through an ether linkage; that is, an "alkoxy" group may be represented as —O-alkyl where alkyl is as defined above. A "lower alkoxy" group intends an alkoxy group containing one to six, more preferably one to four, carbon atoms.

"Allenyl" is used herein in the conventional sense to refer to the group —CH=C=CH$_2$. An "allenyl" group may be unsubstituted or substituted with one or more non-hydrogen substituents.

"Anomer" as used herein means one of a pair of isomers of a cyclic carbohydrate resulting from creation of a new point of symmetry when a rearrangement of atoms occurs at an aldehyde or ketone position.

"Halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refer to an alkyl, alkenyl or alkynyl group, respectively, in which at least one of the hydrogen atoms in the group has been replaced with a halogen atom.

"Heterocycle" or "heterocyclic" refers to a carbocylic ring wherein one or more carbon atoms have been replaced with one or more heteroatoms such as nitrogen, oxygen or sulfur. Examples of heterocycles include, but are not limited to, furan, thiphene, pyrrole, pyrroline, pyrrolidine, dioxolane, oxazole, thiazole, imidazole, imidazolie, imidazolidine, pyrazole, pyrazoline, pyrazolidine, oxadiazole, triazole, thiadiazole, pyran, pyridine, piperidine, dioxane, morpholine, dithiane, thiomorpholine, pyridazine, pyrimidine, pyrazine, piperazine, triazine, trithiane, naphthalene, quinolone, purine, indole, benzofuran, or benzothiophene.

"Heteroatom-containing" refers to a molecule or molecular fragment in which one or more carbon atoms is replaced with an atom other carbon, e.g., nitrogen, oxygen, sulfur, phosphorus or silicon.

"Substituted heterocycle" refers to a heterocycle as just described that contains one or more functional groups such as lower alkyl, acyl, aryl, cyano, halogen, hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like. In other instances where the term "substituted" is used, the substituents which fall under this definition may be readily gleaned from the other definitions of substituents which are presented in the specification as well the circumstances under which such substituents occur in a given chemical compound.

"Substituted" as in "substituted alkyl" or "substituted alkenyl" means that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, silyl, and the like. When the term "substituted" appears prior to a list of possible substituted groups, it is intended that the term apply to every member of that group.

"Effective amount" refers to the amount of a selected compound, intermediate, or reactant that is used to produce an intended result. The precise amount of a compound, intermediate, or reactant used will vary depending upon the particular compound selected and its intended use, the age and weight of the subject, route of administration, and so forth, but may be easily determined by routine experimentation. In the case of the treatment of a condition or disease state, an effective amount is that amount which is used to effectively treat the particular condition or disease state.

The term "subjects" is used throughout the specification to describe an animal, preferably a human, to whom treatment, including prophylactic treatment, with the compositions according to the present invention is provided.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of a novel NPYY2 inhibitor of the instant invention that may be combined with the carrier materials to produce a single dosage form will vary depending upon the host treated, and the particular mode of administration. Preferably, the compositions should be formulated to contain between about 10 milligrams to about 500 milligrams of active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Compounds of the invention are potent, non-peptidic, low molecular weight, selective NPY Y2 inhibitors and are useful in the treating or preventing: anxiolytic disorders and depression; injured mammalian nerve tissue; conditions responsive to treatment through administration of a neurotrophic factor; neurological disorders; bone loss; substance related disorders; and metabolic disorders such as obesity or an obesity-related disorder. Compounds of the invention modulate endocrine functions; particularly those controlled by the pituitary and hypothalamic glands, and therefore may be used to treat inovulation and infertility that may be due to insufficient release of luteinizing hormone (LH) or luteal phase defect.

The compounds compete with the endogenous ligands NPY and possibly non-endogenous ligands, and bind to the NPY2 receptor. In addition, the compounds demonstrate antagonist activity by antagonizing the action of NPY upon binding to the Y2 receptor. The compounds described herein are ligands of the NPY2 receptor, but are not necessarily limited solely in their pharmacological or biological action due to binding to this or any neuropeptide, neurotransmitter or G-protein coupled receptor. For example, the described compounds may also undergo binding to dopamine or serotonin receptors.

"Anxiolytic disorders" include affective disorders such as all types of depression, bipolar disorder, cyclothymia, and dysthymia, anxiety disorders such as generalized anxiety disorder, panic, phobias and obsessive-compulsive disorder, stress disorders including post-traumatic stress disorder, hemorrhagic stress, stress-induced psychotic episodes, psychosocial dwarfism, stress headaches, stress-induced immune systems disorders such as stress-induced fever, and stress-related sleep disorders, and can include eating disorders such as anorexia nervosa, bulimia nervosa, and obesity, and drug addiction.

"Depression" refers to major depressive disorders, dysthymia, bipolar or manic disorders, and the like.

"Nerve tissue" as used herein refers to any vertebrate nerve tissue, particularly including mammalian cells of the central nervous system (CNS) and peripheral nervous system (PNS). More particularly, nerve tissue includes spinal cord neuronal structures, peripheral nervous system nerves, and even nerve cells of the brain.

"Nerve tissue injury", "injured mammalian nerve tissue", or "CNS or PNS nerve tissue injury" include any damage to relevant nerve tissue irrespective of cause, e.g., injuries attributable to trauma including but not limited to nerve tissue lesions, traumatically-induced compression, tumors, hemorrhage, infectious processes, spinal stenosis, or impaired blood supply.

"Treating injured mammalian nerve tissue" includes, but is not limited, to the in vivo administration of compounds, compositions, and methods of the instant invention to restore action potential or nerve impulse conduction through a nerve tissue lesion. The term may also include such administration in an effort to reduce the damaging effects of any injury to mammalian nerve tissue, whether through restoration of action potential or nerve impulse conduction, by stimulating growth or proliferation of nervous tissue, by ameliorating unwanted conditions in the extracellular microenvironment near an injury, or otherwise.

"Neurotrophic factor", as used herein, refers to compounds that are capable of stimulating growth or proliferation of nervous tissue, including compounds of the instant invention and known neurotrophic factors described previously herein.

"Neurological disorders" include CNS disorders such as tinitus, spasticity, and neuropathic pain, supranuclear palsy, AIDS related dementias, multiinfarct dementia, neurodegenerative disorders such as Alzheimer's disease, Parkinson's disease, and Huntington's disease, head trauma, spinal cord trauma, ischemic neuronal damage, amyotrophic lateral sclerosis, and disorders of pain perception such as fibromyalgia and epilepsy.

"Bone loss" refers to enhancement of bone growth or prevention of bone loss caused by conditions such as osteoporosis, osteomalacia, Paget's disease, disorders of bone homeostasis, and the like.

"Substance related disorders" refer to misuse, addiction, or dependence disorders related to the consumption of alcohol, amphetamines, cannabis, hallucinogens, inhalants, nicotine, opioids, phencyclidine, or sedatives.

"Obesity" refers to a condition in which a subject has a body mass index of greater than or equal to 30. "Overweight" refers to a condition in which a subject has a body mass index of greater or equal to 25.0. The body mass index and other definitions are according to the "NIH Clinical Guidelines on the Identification and Evaluation, and Treatment of Overweight and Obesity in Adults" (1998).

"Obesity-related disorder" includes anorexia nervosa, wasting, AIDS-related weight loss, bulimia, cachexia, lipid disorders including hyperlipidemia and hyperuricemia, insulin resistance, noninsulin dependent diabetes mellitus (NIDDM, or Type II diabetes), insulin dependent diabetes mellitus (IDDM or Type I diabetes), diabetes-related complications including microangiopathic lesions, ocular lesions, retinopathy, neuropathy, and renal lesions, cardiovascular disease including cardiac insufficiency, coronary insufficiency, and high blood pressure, atherosclerosis, atheromatous disease, stroke, hypertension, Syndrome X, gallbladder disease, osteoarthritis, sleep apnea, forms of cancer such as uterine, breast, colorectal, kidney, and gallbladder, high cholesterol levels, complications of pregnancy, menstrual irregularities, hirsutism, muscular dystrophy, infertility, and increased surgical risk.

EXAMPLES

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention. Unless otherwise noted, the materials used in the examples were obtained from readily available commercial sources or synthesized by standard methods known to those skilled in the art.

Protocol for Preparative Reversed-Phase HPLC

Gilson® Liquid Chromatograph
Column: YMC-Pack ODS-A, 5 µm, 75×30 mm
Flow rate: 10 mL/min
Detection: λ=220 & 254 nm
Mobile Phase: (10 to 95% acetonitrile/water, 0.05% trifluoroacetic acid)

Protocol for LC/MS (Reversed-Phase)

Hewlett Packard Series 1100
Column: Agilent ZORBAX® C8, 5 µm, 4.6×150 mm
Flow rate: 1 mL/min
Detection: λ=220 & 254 nm
Ionization Method: ESI
Gradient: acetonitrile/water, 0.05% trifluoroacetic acid Mass spectra were obtained on an Agilent series 1100 MSD using electrospray ionization (ESI) in either positive or negative modes as indicated. Preparative thin-layer chromatography was performed using Merck silica gel 60 $F_{254}$ plates measuring 20 cm×20 cm×0.5 mm.

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Example 1

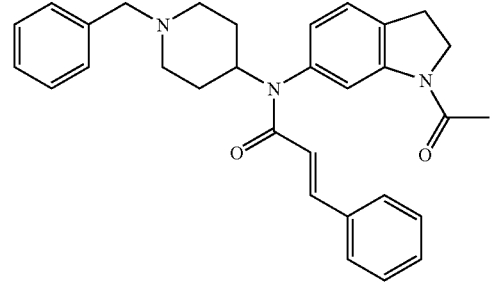

trans-N-(1-Acetyl-2,3-dihydro-1H-indol-6-yl)-N-(1-benzyl-piperidin-4-yl)-3-phenyl-acrylamide To a solution of 1-[6-(1-benzyl-piperidin-4-ylamino)-2,3-dihydro-indol-1-yl]-ethanone (250 mg, 0.72 mmol) in $CH_2Cl_2$ (10 mL) was added cinnamoyl chloride (160 mg, 0.93 mmol) and triethylamine (TEA, 0.30 mL, 2.2 mmol). The mixture was stirred at 25° C. for 16 h. After concentration, the residue was purified by preparative TLC (PTLC, 20% EtOAc/$CH_2Cl_2$) to provide 290 mg (85%) of the desired product. $^1$H NMR (500 MHz, $CDCl_3$): 8.05 (s, 1H), 7.62 (d, J=15.5 Hz, 1H), 7.32-7.20 (m, 10H), 7.17 (d, J=7.9 Hz, 1H), 6.74 (dd, J=6.8, 1.5 Hz, 1H), 6.15 (d, J=15.5 Hz, 1H), 4.80-4.69 (m, 1H), 4.20-4.09 (m, 3H), 3.51-3.45 (m, 1H), 3.31-3.20 (m, 2H), 2.95-2.82 (m, 2H), 2.23 (s, 3H), 2.19-2.08 (m, 2H), 1.91-1.71 (m, 2H). MS: exact mass calculated for $C_{31}H_{33}N_3O_2$, 479.26; m/z found, 480.3 $[M+H]^+$.

Example 2

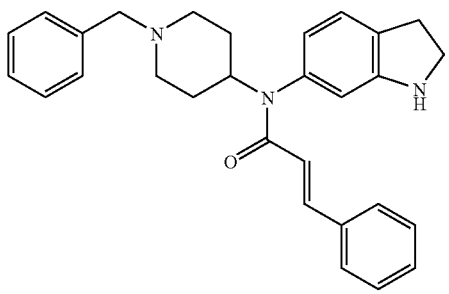

trans-N-(1-Benzyl-piperidin-4-yl)-N-(2,3-dihydro-1H-indol-6-yl)-3-phenyl-acrylamide Step A. 6-Amino-2,3-dihydro-indole-1-carboxylic acid tert-butyl ester. To a mixture of 6-nitroindoline (2 mmol) and TEA (2.2 mmol) in $CH_2Cl_2$ (20 mL) was added di-tert-butyl dicarbonate (2 mmol). The mixture was stirred at 25° C. for 16 h. The mixture was washed with satd. aq. $NaHCO_3$ (20 mL) and brine (20 mL), and then was dried and concentrated. The residue was dissolved in MeOH (4 mL), and $FeCl_3.6H_2O$ (7 mg), $Me_2NNH_2$ (21 mmol), and charcoal (50 mg) were added. The resulting mixture was heated at reflux for 4 h. The mixture was filtered through diatomaceous earth and the filtrate was concentrated to obtain the desired compound in quantitative yield.

Step B. 6-(1-Benzyl-piperidin-4-ylamino)-2,3-dihydro-indole-1-carboxylic acid tert-butyl ester. 1-Benzyl-4-piperidone (1 mmol) was stirred with 6-amino-2,3-dihydro-indole-1-carboxylic acid tert-butyl ester (1.2 mmol), Na$(OAc)_3BH$ (1.3 mmol) and AcOH (1 mmol) in $CH_2Cl_2$ (20 mL). The resulting mixture was stirred at 25° C. for 16 h. The mixture was washed with satd. aq. $NaHCO_3$ (20 mL), and the organic layer was dried and concentrated to provide the crude desired compound.

Step C. trans-6-[(1-Benzyl-piperidin-4-yl)-(3-phenyl-acryloyl)-amino]-2,3-dihydro-indole-1-carboxylic acid tert-butyl ester. To a solution of the product of Step B (1 mmol) in $CH_2Cl_2$ (10 mL) was added cinnamoyl chloride (1 mmol) and TEA (1.1 mmol). The resulting mixture was stirred at 25° C. for 16 h. The mixture was washed with satd aq. $NaHCO_3$ (20 mL), and the organic layer was dried and concentrated. After purification by silica gel chromatography, the desired compound was obtained (60%).

Step D. To a solution of the product of Step C (1 mmol) in $CH_2Cl_2$ (10 mL) was added TFA (1 mL). The mixture was stirred at 25° C. for 16 h. After concentration, the title compound was obtained as its TFA salt in quantitative yield. $^1$H NMR (500 MHz, $CDCl_3$): 9.78 (s, 1H), 7.65 (d, J=15.5 Hz, 1H), 7.46-7.23 (m, 12H), 7.08 (d, J=8.3 Hz, 1H), 6.13 (d, J=15.5 Hz, 1H), 4.99-4.95 (br m, 1H), 4.15-3.95 (m, 4H), 3.40-3.31 (m, 4H), 3.02-2.88 (br m, 2H), 2.11-1.56 (m, 4H). MS: exact mass calculated for $C_{29}H_{31}N_3O$, 437.25; m/z found, 438.3 $[M+H]^+$.

Example 3

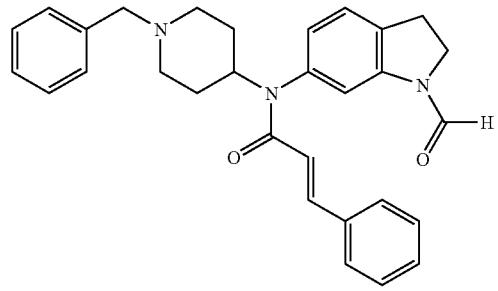

trans-N-(1-Benzyl-piperidin-4-yl)-N-(1-formyl-2,3-dihydro-1H-indol-6-yl)-3-phenyl-acrylamide To a solution of the compound prepared in Example 2 (24 mg, 0 062 mmol) in acetonitrile (2 mL) was added formic acid (2.2 μL, 0.060 mmol) and 1,1'-carbonyldiimidazole (11 mg, 0.060 mmol). The mixture was stirred at 25° C. for 16 h. After concentration, the residue was purified by PTLC (20% $EtOAc/CH_2Cl_2$) to give the title compound (10 mg, 39%). $^1$H NMR (500 MHz, $CDCl_3$): 8.88 (s, 0.75H), 8.52 (s, 0.25H), 7.66 (d, J=15.6 Hz, 1H), 7.33-7.21 (m, 12H), 6.78 (dd, J=6.2, 1.7 Hz, 1H), 6.14-6.11 (m, 1H), 4.77-4.72 (m, 1H), 4.22-4.13 (m, 2H), 3.47-3.45 (m, 2H), 3.27-3.19 (m, 2H), 3.00-2.82 (br m, 2H), 2.17-2.13 (br m, 2H), 1.84-1.78 (m, 2H), 1.50-1.44 (m, 2H). MS: exact mass calculated for $C_{30}H_{31}N_3O_2$, 465.24; m/z found, 466.2 $[M+H]^+$.

Example 4

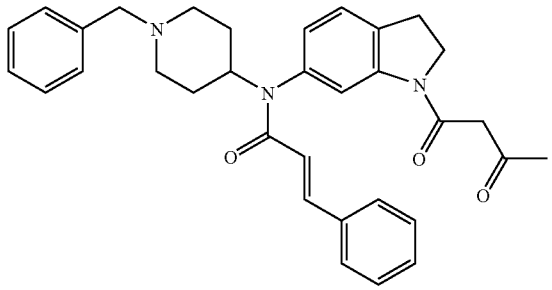

trans-N-(1-Benzyl-piperidin-4-yl)-N-[1-(3-oxo-butyryl)-2,3-dihydro-1H-indol-6-yl]-3-phenyl-acrylamide To a solution of the compound prepared in Example 2 (41 mg, 0.092 mmol) in $CH_2Cl_2$ (3 mL) was added TEA (1.5 μL, 0.010 mmol) and diketene (8.1 μL, 0.10 mmol). The mixture was stirred at 25° C. for 16 h. After concentration, the residue was purified by PTLC (20% $EtOAc/CH_2Cl_2$) to give the title compound (26 mg, 53%). $^1$H NMR (500 MHz, $CDCl_3$): 8.04 (s, 1H), 7.65-7.61 (m, 1H), 7.30-7.16 (m, 12H), 6.79-6.72 (m, 2H), 6.18-6.11 (m, 1H), 4.76-4.71 (m, 1H), 4.20-4.10 (m, 2H), 3.45 (s, 2H), 3.35-3.25 (m, 2H), 2.95-2.85 (m, 2H), 2.34 (s, 3H), 2.25-2.10 (m, 2H), 2.00-1.85 (br m, 1H), 1.85-1.75 (br m, 1H), 1.65-1.50 (m, 1H),

Example 5

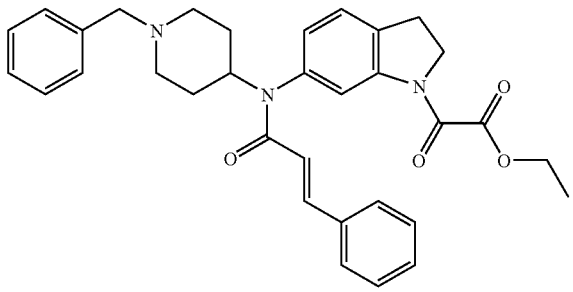

trans-{6-[(1-Benzyl-piperidin-4-yl)-(3-phenyl-acryloyl)-amino]-2,3-dihydro-indol-1-yl}-oxo-acetic acid ethyl ester To a solution of the compound prepared in Example 2 (48 mg, 0.11 mmol) in CH$_2$Cl$_2$ (3 mL) was added pyridine (18 μL, 0.22 mmol), 4-(dimethylamino)-pyridine (DMAP, 1.2 mg, 0.010 mmol), and chloro-oxo-acetic acid ethyl ester (25 μL, 0.22 mmol). The mixture was stirred at 25° C. for 16 h. After concentration, the residue was purified by PTLC (20% EtOAc/CH$_2$Cl$_2$) to give the title compound (15 mg, 36%). $^1$H NMR (500 MHz, CDCl$_3$): 8.04 (s, 1H), 7.64 (d, J=15.5 Hz, 1H), 7.28-7.19 (m, 10H), 7.03 (dd, J=8.1, 1.8 Hz, 1H), 6.13 (d, J=15.5 Hz, 1H), 4.75-4.72 (m, 1H), 4.40-4.32 (m, 4H), 3.45-3.44 (m, 2H), 3.28 (q, J=7.8 Hz, 2H), 2.94-2.82 (br m, 2H), 2.13 (t, J=7.8 Hz, 2H), 1.88-1.86 (br m, 1H), 1.79-1.77 (br m, 1H), 1.59-1.48 (m, 1H), 1.43-1.38 (m, 4H). MS: exact mass calculated for C$_{33}$H$_{35}$N$_3$O$_4$, 537.26; m/z found, 538.3 [M+H]$^+$.

Example 6

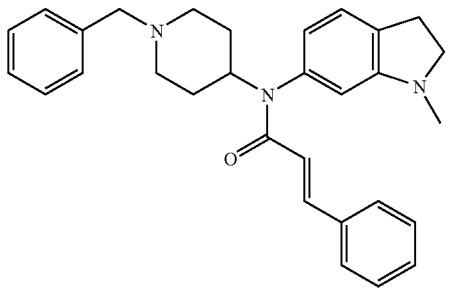

trans-N-(1-Benzyl-piperidin-4-yl)-N-(1-methyl-2,3-dihydro-1H-indol-6-yl)-3-phenyl-acrylamide Step A. 1-Methyl-2,3-dihydro-1H-indol-6-ylamine. 6-Nitroindoline (2 mmol) was combined with methyl iodide (2.2 mmol), n-Bu$_4$I (7.4 mg, 0.020 mmol), and K$_2$CO$_3$ (350 mg, 2.5 mmol) in acetone (10 mL). The mixture was stirred at 25° C. for 16 h. The mixture was partitioned between CH$_2$Cl$_2$ and satd. aq. NaHCO$_3$ (20 mL), and the organic layer was dried and concentrated. Purification by silica gel chromatography provided 1-methyl-6-nitroindoline (300 mg, 84%). To a solution of 1-methyl-6-nitroindoline (194 mg, 1.15 mmol) in MeOH (2 mL) was added FeCl$_3$.6H$_2$O (3 mg), Me$_2$NNH$_2$ (0.80 mL, 11 mmol), and charcoal (25 mg). The mixture was heated at reflux for 4 h. The mixture was filtered through diatomaceous earth, and the filtrate was concentrated to provide the desired compound in quantitative yield.

Step B. (1-Benzyl-piperidin-4-yl)-(1-methyl-2,3-dihydro-1H-indol-6-yl)-amine. The product from Step A (161 mg, 1.1 mmol) was converted to the desired compound as in Example 2, Step B.

Step C. The title compound (80 mg, 35%) was prepared as in Example 2, Step C. $^1$H NMR (500 MHz, CDCl$_3$): 7.63 (d, J=15.5 Hz, 1H), 7.30-7.25 (m, 10H), 7.02 (d, J=7.4 Hz, 1H), 6.38-6.36 (d, J=8.8 Hz, 1H), 6.25 (d, J=15.5 Hz, 1H), 6.14 (s, 1H), 4.73-4.68 (m, 1H), 3.46-3.34 (m, 4H), 3.02-2.86 (m, 4H), 2.73 (s, 3H), 2.17-2.12 (m, 2H), 1.86-1.77 (m, 2H), 1.61-1.51 (m, 2H). MS: exact mass calculated for C$_{30}$H$_{33}$N$_3$O, 451.26; m/z found, 452.2 [M+H]$^+$.

Example 7

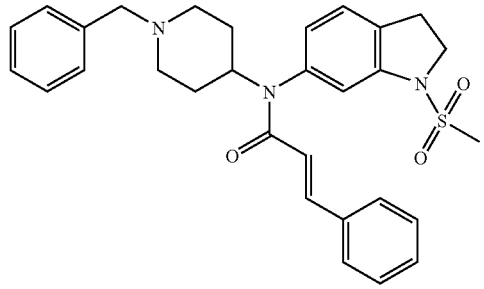

trans-N-(1-Benzyl-piperidin-4-yl)-N-(1-methanesulfonyl-2,3-dihydro-1H-indol-6-yl)-3-phenyl-acrylamide Step A. 1-Methanesulfonyl-6-nitro-2,3-dihydro-1H-indole. To a solution of 6-nitroindoline (2 mmol) in CH$_2$Cl$_2$ (10 mL) was added pyridine (180 μL, 2.2 mmol), DMAP (0.1 mmol), and methanesulfonyl chloride (170 μL, 2.2 mmol). The resulting mixture was stirred at 25° C. for 16 h. The mixture was then washed with satd. aq. NaHCO$_3$ (20 mL), and the organic layer was dried and concentrated. Purification by silica gel chromatography provided the desired compound (410 mg, 85%).

Step B. 1-Methanesulfonyl-2,3-dihydro-1H-indol-6-ylamine. To a solution of 1-methanesulfonyl-6-nitroindoline (240 mg, 1.0 mmol) in MeOH (2 mL) was added with FeCl$_3$.6H$_2$O (3 mg), Me$_2$NNH$_2$ (0.80 mL, 11 mmol), and charcoal (25 mg). The mixture was heated at reflux for 4 h. After filtration through a pad of diatomaceous earth, the filtrate was concentrated to obtain the title compound in quantitative yield.

Step C. (1-Benzyl-piperidin-4-yl)-(1-methanesulfonyl-2,3-dihydro-1H-indol-6-yl)-amine. The crude title compound was prepared from the product from Step B (420 mg, 1.1 mmol) as in Example 2, Step B.

Step D. The title compound (77 mg, 50%) was prepared from the product of Step C as in Example 2, Step C. $^1$H NMR (500 MHz, CDCl$_3$): 7.63 (d, J=15.5 Hz, 1H), 7.29-7.18 (m, 12H), 6.73 (dd, J=8.3, 1.8 Hz, 1H), 6.10 (d, J=15.5 Hz, 1H), 4.79-4.71 (m, 1H), 4.04 (q, J=9.3 Hz, 1H), 3.45 (s, 2H), 3.19 (q, J=8.2 Hz, 1H), 2.91-2.89 (br m, 2H), 2.81 (s, 3H), 2.16-2.14 (br m, 2H) 1.89-1.78 (br m, 2H), 1.55-1.40 (br m, 2H). MS: exact mass calculated for C$_{30}$H$_{33}$N$_3$O$_3$S, 515.22; m/z found, 516.3 [M+H]$^+$.

Example 8

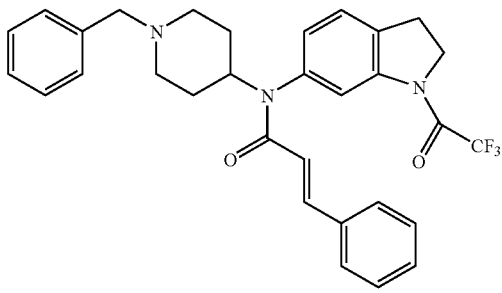

trans-N-(1-Benzyl-piperidin-4-yl)-3-phenyl-N-[1-(2,2,2-trifluoro-acetyl)-2,3-dihydro-1H-indol-6-yl]-acrylamide To a solution of the compound prepared in Example 2 (48 mg, 0.11 mmol) in CH$_2$Cl$_2$ (3 mL) was added 1,3-dicyclohexylcarbodiimide (23 mg, 0.11 mmol) and TFA (13 mg, 0.11 mmol). The mixture was stirred at 25° C. for 16 h. After concentration, the residue was purified by PTLC (20% EtOAc/CH$_2$Cl$_2$) to give the title compound (24 mg, 41%). $^1$H NMR (500 MHz, CDCl$_3$): 7.65 (d, J=15.5 Hz, 1H), 7.29-7.23 (m, 11H), 6.92-6.90 (d, J=8.5 Hz, 1H), 6.12 (d, J=15.5 Hz, 1H), 4.79-4.74 (m, 1H), 4.38 (t, J=7.6 Hz, 1H), 3.46 (s, 2H), 3.33 (q, J=7.8 Hz, 2H), 3.00-2.82 (br m, 2H), 2.14 (t, J=11.4 Hz, 1H) 1.90-1.78 (m, 2H), 1.54-1.41 (m, 2H). MS: exact mass calculated for C$_{31}$H$_{30}$F$_3$N$_3$O$_2$, 533.58; m/z found, 534.2 [M+H]$^+$.

Example 9

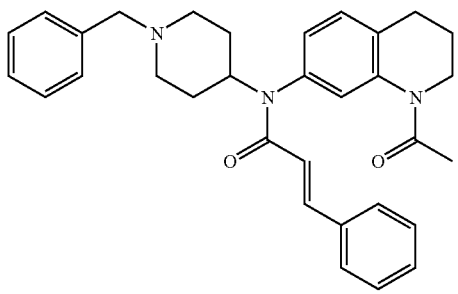

trans-N-(1-Acetyl-1,2,3,4-tetrahydro-quinolin-7-yl)-N-(1-benzyl-piperidin-4-yl)-3-phenyl-acrylamide Step A. 7-Amino-3,4-dihydro-2H-quinoline-1-carboxylic acid tert-butyl ester. 7-Nitro-1,2,3,4-tetrahydroquinoline (280 mg, 1.0 mmol) was converted to the desired compound (100%) as in Example 2, Step A.

Step B. 7-(1-Benzyl-piperidin-4-ylamino)-3,4-dihydro-2H-quinoline-1-carboxylic acid tert-butyl ester. The product from Step A (250 mg, 1.0 mmol) was converted to the desired compound (210 mg, 50%) as in Example 2, Step B.

Step C. N-(1-Benzyl-piperidin-4-yl)-3-phenyl-N-(1,2,3,4-tetrahydro-quinolin-7-yl)-acrylamide. The product from Step B (110 mg, 0.25 mmol) was converted to the desired compound (85 mg, 57%) as in Example 2, Step C.

Step D. N-(1-Acetyl-1,2,3,4-tetrahydro-quinolin-7-yl)-N-(1-benzyl-piperidin-4-yl)-3-phenyl-acrylamide. The desired compound (100%) was obtained as its TFA salt from the product of Step C (85 mg) as in Example 2, Step D.

Step E. To a solution of the product from Step D (25 mg, 0.044 mmol) in CH$_2$Cl$_2$ (10 mL) was added pyridine (7.0 μL, 0.090 mmol), DMAP (0.5 mg, 4 μmol), and acetyl chloride (6.3 μL, 0.089 mmol). The mixture was stirred at 25° C. for 16 h. After concentration, the residue was purified by PTLC (20% EtOAc/CH$_2$Cl$_2$) to give the title compound (11 mg, 50%). $^1$H NMR (500 MHz, CDCl$_3$): 7.64 (d, J=15.5 Hz, 1H), 7.35-7.17 (m, 12H), 6.88-6.87 (br m, 1H), 6.13 (d, J=15.5 Hz, 1H), 4.77-4.72 (m, 1H), 3.92-3.80 (m, 1H), 3.80-3.69 (m, 1H), 3.49 (s, 2H), 2.94-2.92 (br m, 2H), 2.85-2.75 (br m, 2H), 2.24-2.10 (br m, 5H), 2.04-1.99 (m, 2H), 1.88-1.75 (br m, 2H), 1.58-1.44 (br m, 2H). MS: exact mass calculated for C$_{32}$H$_{35}$N$_3$O$_2$, 493.27; m/z found, 494.2 [M+H]$^+$.

Example 10

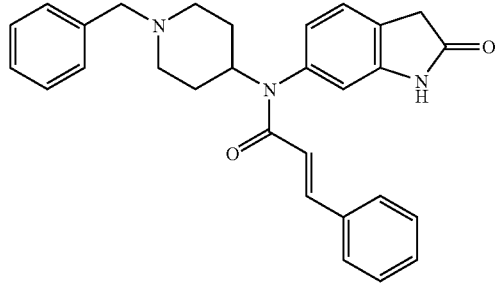

trans-N-(1-Benzyl-piperidin-4-yl)-N-(2-oxo-2,3-dihydro-1H-indol-6-yl)-3-phenyl-acrylamide Step A. 6-Nitro-1,3-dihydro-indol-2-one. To a solution of (2,4-dinitrophenyl)-acetic acid methyl ester (5 mmol) in 50 mL of ethanol was added a suspension of 10% Pd/C (0.12 g) in ethanol/dimethoxyethane (1:1). The mixture was hydrogenated at 50 psi until hydrogen uptake ceased. The mixture was filtered to remove the catalyst, and the filtrate was concentrated. The residue was diluted with 10 mL of 1 M HCl and heated at reflux for 20 min. The mixture was cooled to rt, neutralized with 1 M NaOH to pH 7, and extracted with EtOAc (3×). The organic layers were combined, dried over Na$_2$SO$_4$, and concentrated to give the desired compound as a semi-solid, which was used directly in the next step.

Step B. The title compound (75 mg, 31%) was prepared from the product of Step A as in Example 2, Steps B and C. $^1$H NMR (500 MHz, CDCl$_3$): 9.39 (s, 1H), 7.65 (d, J=15.5 Hz, 1H), 7.32-7.14 (m, 10H), 7.04 (t, J=7.0 Hz, 1H), 6.71 (dd, J=7.8, 1.6 Hz, 1H), 6.14 (br s, 1H), 6.06 (d, J=15.5 Hz, 1H), 4.85-4.72 (m, 1H), 3.59-3.30 (m, 4H), 3.06-3.04 (br m, 1H), 2.85-2.83 (br m, 1H), 2.23-2.09 (m, 2H), 1.83-1.57 (m, 4H). MS: exact mass calculated for $C_{29}H_{29}N_3O_2$, 451.23; m/z found, 452.2 $[M+H]^+$.

Example 11

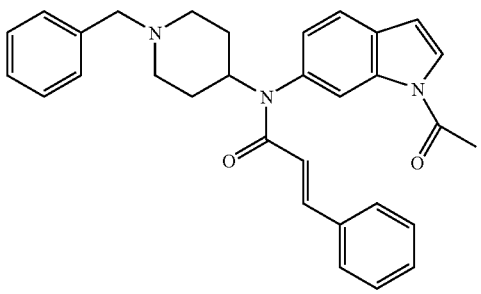

trans-N-(1-Acetyl-1H-indol-6-yl)-N-(1-benzyl-piperidin-4-yl)-3-phenyl-acrylamide Step A. 1H-Indol-6-ylamine. The desired compound (100%) was prepared from 6-nitroindole (650 mg, 4.0 mmol) as in Example 7, Step B.

Step B. (1-Benzyl-piperidin-4-yl)-(1H-indol-6-yl)-amine. The desired compound (756 mg, 62%) was prepared from the product from Step A (530 mg, 4.0 mmol) as in Example 2, Step B.

Step C. trans-N-(1-Benzyl-piperidin-4-yl)-N-(1H-indol-6-yl)-3-phenyl-acrylamide. The desired compound (135 mg, 62%) was prepared from the product from Step B (150 mg, 0.50 mmol) as in Example 2, Step C.

Step D. To a solution of the product from Step C (80 mg, 0.2 mmol) in THF (20 mL) was added NaH (95%, 8.8 mg, 0.37 mmol). After 10 min, acetyl chloride (26 μL, 0.37 mmol) was added. The resulting mixture was stirred at 25° C. for 16 h. After concentration, the residue was purified by PTLC (20% EtOAc/$CH_2Cl_2$) to give the title compound (35 mg, 41%). $^1H$ NMR (500 MHz, $CDCl_3$): 7.63 (d, J=15.6 Hz, 1H), 7.57 (d, J=8.1 Hz, 1H), 7.52 (d, J=3.4 Hz 1H), 7.34-7.12 (m, 11H), 7.03 (d, J=8.7 Hz, 1H), 6.71 (d, J=3.4 Hz, 1H), 6.09 (d, J=15.6 Hz, 1H), 4.81-4.78 (m, 1H), 3.44 (s, 2H), 2.91-2.87 (m, 2H), 2.65 (s, 3H), 2.20-2.05 (m, 1H), 1.94-1.92 (br m, 1H), 1.83-1.81 (br m, 1H), 1.57-1.41 (m, 3H). MS: exact mass calculated for $C_{31}H_{31}N_3O_2$, 477.24; m/z found, 478.3 $[M+H]^+$.

Example 12

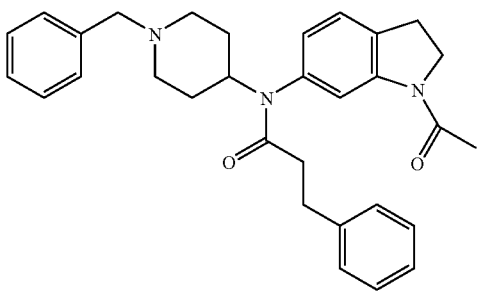

N-(1-Acetyl-2,3-dihydro-1H-indol-6-yl)-N-(1-benzyl-piperidin-4-yl)-3-phenyl-propionamide trans-N-(1-Acetyl-2,3-dihydro-1H-indol-6-yl)-N-(1-benzyl-piperidin-4-yl)-3-phenyl-acrylamide (Example 1, 0.6 g, 1 mmol) was dissolved in 50 mL of MeOH and 20% Pd(OH)$_2$/C (21 mg) was added in portions over the course of the reaction. The mixture was shaken in a Parr hydrogenator at ~50 psi overnight. The mixture was filtered through a pad of diatomaceous earth. The filtrate was concentrated to yield the crude product contaminated with de-benzylated material. The mixture was purified by reverse-phase HPLC to yield the desired product as its TFA salt as a light pink powder (0.06 g, 8%). $^1H$ NMR (400 MHz, DMSO-$d_6$): 9.13 (br s, 1H), 7.80 (s, 1H), 7.45 (s, 5H), 7.32-7.09 (m, 4H), 7.06 (d, J=9.1 Hz, 2H), 6.69 (dd, J=6.3, 2.4 Hz, 1H), 4.78-4.6 (m, 1H), 4.23 (d, J=9.2 Hz, 2H), 4.12 (q, J=8.8 Hz, 2H), 3.39-3.23 (m, 2H), 3.23-3.01 (m, 4H), 2.77 (t, J=8.7 Hz, 2H), 2.25-2.02 (m, 5H), 1.97-1.80 (m, 2H), 1.65-1.33 (m, 2H). MS: exact mass calculated for $C_{31}H_{35}N_3O_2$, 481.27; m/z found, 482.3 $[M+H]^+$.

Example 13

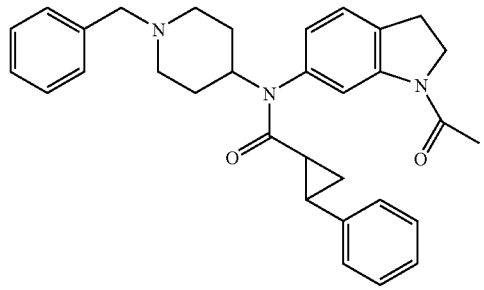

trans-2-Phenyl-cyclopropanecarboxylic acid(1-acetyl-2,3-dihydro-1H-indol-6-yl)-(1-benzyl-piperidin-4-yl)-amide To a solution of 1-[6-(1-benzyl-piperidin-4-ylamino)-2,3-dihydro-indol-1-yl]-ethanone (0.353 g, 1.01 mmol) in 50 mL of acetonitrile was added diisopropylethylamine (0.193 mL, 1.11 mmol) and trans-2-phenyl-1-cyclopropanecarbonyl chloride (90%, 0.174 mL, 1.01 mmol). The reaction mixture was stirred overnight, and then was filtered through diatomaceous earth. The filtrate was evaporated and the residue was chromatographed over silica gel (acetone/MeOH/$CH_2Cl_2$) to provide the desired product as a tan solid (0.30 g, 61%). $^1H$ NMR (400 MHz, $CDCl_3$): 8.04 (s, 1H), 7.38-6.98 (m, 9H), 6.97-6.82 (m, 2H), 6.76 (dd, J=12.5, 6.2 Hz, 1H), 4.65 (br t, J=12.7 Hz, 1H), 4.12 (t, J=9.5 Hz, 1H), 4.09-3.87 (m, 1H), 3.44 (s, 2H), 3.26-3.07 (m, 2H), 2.97-2.79 (m, 2H), 2.51-2.47 (m, 1H), 2.29-1.98 (m, 5H), 1.92-1.66 (m, 2H), 1.65-1.29 (m, 4H), 1.08-0.96 (m, 1H). MS: exact mass calculated for $C_{32}H_{35}N_3O_2$, 493.27; m/z found, 494.3 $[M+H]^+$.

Example 14

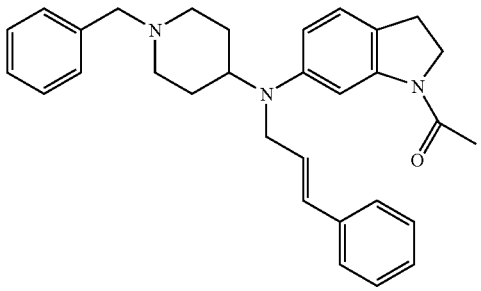

trans-1-{6-[(1-Benzyl-piperidin-4-yl)-(3-phenyl-allyl)-amino]-2,3-dihydro-indol-1-yl}-ethanone 1-[6-(1-Benzyl-piperidin-4-ylamino)-2,3-dihydro-indol-1-yl]-ethanone (0.357 g, 1.02 mmol) was dissolved in acetonitrile (50 mL) with stirring. Cinnamyl bromide (0.212 g, 1.08 mmol) was added and the reaction was stirred for 3 days. Concentration of the reaction mixture gave a residue that was chromatographed using reverse-phase HPLC to provide the TFA salt of the desired product as a tan powder (0.183 g, 31%). LC/MS analysis showed a nearly 1:1 mixture of products, both showing the correct molecular ion. MS: exact mass calculated for $C_{31}H_{35}N_3O$, 465.28; m/z found, 466.3 $[M+H]^+$.

Example 15

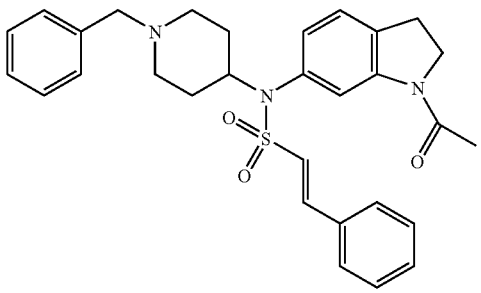

trans-2-Phenyl-ethenesulfonic acid(1-acetyl-2,3-dihydro-1H-indol-6-yl)-(1-benzyl-piperidin-4-yl)-amide A mixture of 1-[6-(1-benzyl-piperidin-4-ylamino)-2,3-dihydro-indol-1-yl]-ethanone (0.10 g, 0.29 mmol), 2-phenyl-ethenesulfonyl chloride (87 mg, 0.43 mmol), and TEA (0.08 mL, 0.57 mmol) in $CH_2Cl_2$ (5 mL) was stirred at rt for 20 h. The reaction mixture was concentrated, and the residue was purified on silica gel (60-70% EtOAc/hexanes) to afford the title compound (138 mg, 92%). $^1H$ NMR (500 MHz, $CDCl_3$): 8.12 (s, 1H), 7.50-7.48 (m, 2H), 7.43 (s, 1H), 7.41-7.39 (m, 3H), 7.25 (d, J=6.8 Hz, 2H), 7.20 (t, J=7.0 Hz, 3H), 7.15 (d, J=7.9 Hz, 1H), 6.91 (d, J=7.8 Hz, 1H), 6.86 (d, J=15.0 Hz, 1H), 4.13 (t, J=8.0 Hz, 2H), 3.98-3.40 (m, 1H), 3.41 (s, 2H), 3.20 (t, J=8.5 Hz, 2H), 2.87 (d, J=10.5 Hz, 2H), 2.20 (s, 3H), 2.06-2.02 (m, 2H), 1.88 (d, J=10.7 Hz, 2H), 1.61-1.55 (m, 2H). MS: exact mass calculated for $C_{30}H_{33}N_3O_3S$, 515.22; m/z found, 516.3 $[M+H]^+$.

Example 16

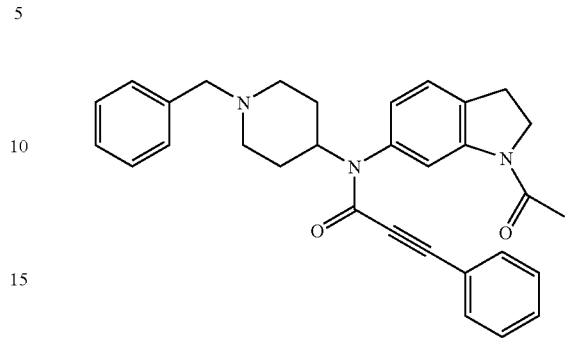

3-Phenyl-propynoic acid(1-acetyl-2,3-dihydro-1H-indol-6-yl)-(1-benzyl-piperidin-4-yl)-amide A mixture of phenyl-propynoic acid (220 mg, 1.5 mmol) and thionyl chloride (3.0 mL) in toluene (3.0 mL) was heated at reflux for 4 h. The reaction mixture was cooled to rt and the excess thionyl chloride and toluene were removed under reduced pressure. The resulting crude acid chloride was dissolved in $CH_2Cl_2$ (5 mL) and treated with 1-[6-(1-benzyl-piperidin-4-ylamino)-2,3-dihydro-indol-1-yl]-ethanone (349 mg, 1.0 mmol) and TEA (0.28 mL, 2.0 mmol) at rt for 20 h. The reaction mixture was concentrated, and the residue was purified on silica gel (60-70% EtOAc/hexanes) to afford the title compound (402 mg, 84%). $^1H$ NMR (500 MHz, $CDCl_3$): 8.12 (s, 1H), 7.28-7.18 (m, 9H), 7.09 (d, J=7.8 Hz, 2H), 6.86 (dd, J=8.0, 1.7 Hz, 1H), 4.65-4.59 (m, 1H), 4.13 (t, J=8.5 Hz, 2H) 3.44 (s, 2H), 3.24 (t, J=8.5 Hz, 2H), 2.89 (d, J=10.7 Hz, 2H), 2.22 (s, 3H), 2.10 (t, J=10.8 Hz, 2H), 1.90-1.78 (m, 2H), 1.63-1.58 (m, 2H). MS: exact mass calculated for $C_{31}H_{31}N_3O_2$, 477.24; m/z found, 478.3 $[M+H]^+$.

Example 17

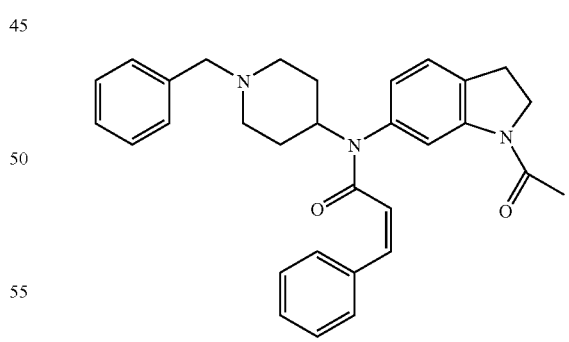

cis-N-(1-Acetyl-2,3-dihydro-1H-indol-6-yl)-N-(1-benzyl-piperidin-4-yl)-3-phenyl-acrylamide Step A. {[(1-Acetyl-2,3-dihydro-1H-indol-6-yl)-(1-benzyl-piperidin-4-yl)-carbamoyl]-methyl}-phosphonic acid bis-(2,2,2-trifluoro-ethyl) ester. A mixture of 1-[6-(1-benzyl-piperidin-4-ylamino)-2,3-dihydro-indol-1-yl]-ethanone (0.50 g, 1.4 mmol) and [bis-(2,2,2-trifluoro-ethoxy)-phosphoryl]- acetic acid methyl ester (910 mL, 4.3 mmol) was dissolved in 10 mL of xylenes and heated at reflux for 12 h. The mixture was concentrated in vacuo and the residue was purified by silica gel chromatography (EtOAc) to afford 468 mg (52%) of the desired intermediate as a yellow foam. $^1$H NMR (500 MHz, CDCl$_3$): 7.97 (br s, 1H), 7.27-7.19 (m, 6H), 6.76-6.74 (m, 1H), 4.56-4.38 (m, 4H), 4.16-4.12 (m, 2H), 3.42 (s, 2H), 3.27-3.22 (m, 2H), 2.91-2.86 (m, 4H), 2.24 (s, 3H), 2.09-2.04 (m, 2H), 1.80-1.73 (m, 2H), 1.60 (br s, 1H), 1.47-1.39 (m, 2H). MS: exact mass calculated for C$_{28}$H$_{32}$F$_6$N$_3$O$_5$P, 635.20; m/z found, 636.2 [M+H]$^+$, 658.2 [M+Na]$^+$.

Step B. To a mixture of the product of Step A (0.100 g, 0.157 mmol) and 18-crown-6 (208 mg, 0.787 mmol) in 1 mL of THF at −78° C. was added 314 μL of potassium bis(trimethylsilyl)amide (0.5 M in toluene) followed by benzaldehyde (16 mL, 0.157 mmol). After 30 min, the reaction was quenched by the addition of satd. aq. NH$_4$Cl and EtOAc. The organic layer was separated, dried over Na$_2$SO$_4$, filtered, and concentrated in vacuo. The crude material was purified by PTLC (70% EtOAc/hexanes) to afford 57 mg (75%) of the title compound as a white foam. $^1$H NMR (500 MHz, CDCl$_3$): 7.90 (s, 1H), 7.40 (d, J=5.0 Hz, 2H), 7.32-7.19 (m, 8H), 6.96 (d, J=6.9 Hz, 1H), 6.36 (d, J=8.7 Hz, 1H), 6.28 (d, J=12.5 Hz, 1H), 5.78 (d, J=12.5 Hz, 1H), 4.67 (br s, 1H), 4.11-4.07 (m, 2H), 3.43 (s, 2H), 3.18 (br s, 2H), 2.87-2.85 (m, 2H), 2.20 (s, 3H), 2.13-2.8 (m, 2H), 1.79 (br s, 2H), 1.43 (br s, 2H). MS: exact mass calculated for C$_{31}$H$_{33}$N$_3$O$_2$, 479.26; m/z found, 480.2 [M+H]$^+$, 502.3 [M+Na]$^+$.

Example 18

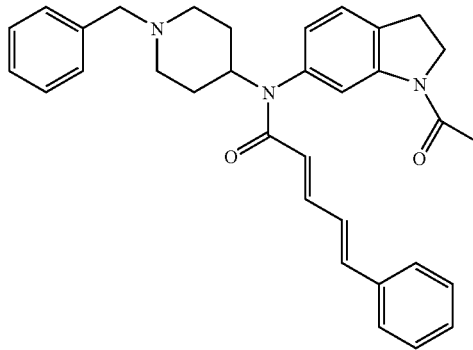

trans,trans-5-Phenyl-penta-2,4-dienoic acid (1-acetyl-2,3-dihydro-1H-indol-6-yl)-(1-benzyl-piperidin-4-yl)-amide Step A. {[(1-Acetyl-2,3-dihydro-1H-indol-6-yl)-(1-benzyl-piperidin-4-yl)-carbamoyl]-methyl}-phosphonic acid diethyl ester. A mixture of 1-[6-(1-benzyl-piperidin-4-ylamino)-2,3-dihydro-indol-1-yl]-ethanone (2.5 g, 7.16 mmol), methyl diethylphosphonoacetate (4.0 mL, 21 mmol) and catalytic DMAP was suspended in 36 mL of m-xylenes and heated at reflux for 48 h. The solution was concentrated in vacuo and the residue was purified by silica gel chromatography (5% MeOH/EtOAc) to afford 2.5 g (65%) of the desired intermediate. $^1$H NMR (500 MHz, CDCl$_3$): 7.97 (br s, 1H), 7.27-7.15 (m, 6H), 6.80-6.79 (m, 1H), 4.62-4.60 (m, 1H), 4.21-4.06 (m, 6H), 3.41 (s, 2H), 3.23-3.20 (m, 2H), 2.84 (br s, 2H), 2.74-2.70 (m, 2H), 2.22 (s, 3H), 2.08-2.04 (m, 2H), 1.81-1.72 (m, 2H), 1.48-1.26 (m, 7H). MS: exact mass calculated for C$_{28}$H$_{38}$N$_3$O$_5$P, 527.25; m/z found, 528.3 [M+H]$^+$, 550.2 [M+Na]$^+$.

Step B. To a mixture of the product of Step A (157 mg, 0.309 mmol) and LiCl (62.5 mg, 1.48 mmol) in 3.5 mL of acetonitrile was added 1,8-diazabicyclo[5.4.0]undec-7-ene (DBU, 40.4 μL, 0.324 mmol) followed by 3-phenyl-propenal (43 μL, 0.34 mmol). The mixture was stirred at rt for 12 h and then was diluted with satd. aq. NH$_4$Cl and CH$_2$Cl$_2$. The organic layer was separated and washed with brine, dried over Na$_2$SO$_4$, filtered and concentrated in vacuo. Purification by silica gel chromatography (60% EtOAc/hexanes) afforded 125 mg (80%) of the title compound. $^1$H NMR (500 MHz, CDCl$_3$): 8.01 (s, 1H), 7.41-7.17 (m, 10H), 6.80-6.60 (m, 5H), 5.74-5.71 (m, 1H), 4.73-3.68 (m, 1H), 4.16-4.11 (m, 2H), 3.44 (br s, 2H), 3.28-3.23 (m, 2H), 2.88 (br s, 2H), 2.23 (s, 3H), 2.14-2.10 (m, 2H), 1.86-1.76 (m, 2H), 1.63-1.42 (m, 2H).

Example 19

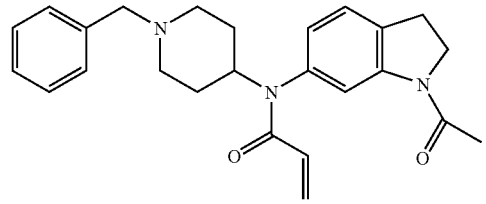

N-(1-Acetyl-2,3-dihydro-1H-indol-6-yl)-N-(1-benzyl-piperidin-4-yl)-acrylamide

The title compound (0.34 g, 83%), obtained as a pale yellow glassy solid, was prepared from 1-[6-(1-benzyl-piperidin-4-ylamino)-2,3-dihydro-indol-1-yl]-ethanone (0.350 g, 1.00 mmol) and acryloyl chloride (0.080 mL, 1.0 mmol) as in Example 13. $^1$H NMR (300 MHz, CDCl$_3$): 7.98 (s, 1H), 7.34-7.12 (m, 6H), 6.72 (dd, J=9.1, 2.2 Hz, 1H), 6.31 (dd, J=15.3, 2.2 Hz, 1H), 5.88 (dd, J=12.5, 10.1 Hz, 1H), 5.43 (dd, J=10.1, 2.2 Hz, 1H), 4.77-4.61 (m, 1H), 4.13 (t, J=8.6 Hz, 2H), 3.44 (s, 2H), 3.24 (t, J=9.4 Hz, 2H), 2.88 (br d, J=10.2 Hz, 2H), 2.23 (s, 3H), 2.12 (t, J=12.5 Hz, 2H), 1.90-1.70 (br m, 2H), 1.60-1.35 (br m, 2H). MS: exact mass calculated for C$_{25}$H$_{29}$N$_3$O$_2$, 403.23; m/z found, 404.3 [M+H]$^+$.

Example 20

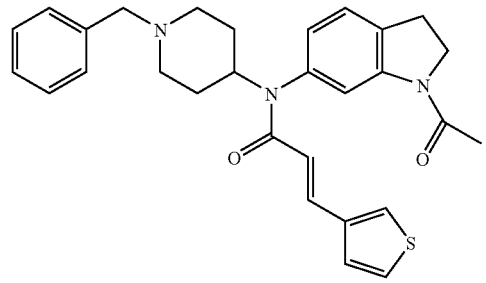

trans-N-(1-Acetyl-2,3-dihydro-1H-indol-6-yl)-N-(1-benzyl-piperidin-4-yl)-3-thiophen-3-yl-acrylamide To a mixture of trans-3-thiophen-3-yl-acrylic acid (66 mg, 0.43 mmol) and oxalyl chloride (45 μL, 0.52 mmol) in 2 mL of CH$_2$Cl$_2$ was added a catalytic amount of DMF. After stirring at rt for 2 h, the mixture was concentrated in vacuo. The resulting crude acid chloride was dissolved in CH$_2$Cl$_2$ and treated with TEA (80 μL, 0.58 mmol) and 1-[6-(1- benzyl-piperidin-4-ylamino)-2,3-dihydro-indol-1-yl]-ethanone (0.100 g, 0.286 mmol). After stirring for 4 h, the mixture was washed with satd. aq. NaHCO$_3$ followed by brine. The organic layer was dried over Na$_2$SO$_4$, filtered, and concentrated in vacuo. Purification by silica gel chromatography (60% EtOAc/hexanes) afforded 118 mg (64%) of the title compound. $^1$H NMR (500 MHz, CDCl$_3$): 8.02 (br s, 1H), 7.83 (d, J=15.7 Hz, 1H), 7.39-7.16 (m, 8H), 6.94-6.93 (m, 1H), 6.73-6.72 (m, 1H), 5.97 (d, J=15.7 Hz, 1H), 4.74-4.70 (m, 1H), 4.17-4.13 (m, 2H), 3.45 (br s, 2H), 3.28-3.23 (m, 2H), 2.88 (br s, 3H), 2.23 (s, 3H), 2.13 (m, 2H), 1.88-1.76 (m, 3H). MS: exact mass calculated for C$_{29}$H$_{18}$N$_3$O$_2$, 485.21; m/z found, 486.2 [M+H]$^+$, 508.1 [M+Na]$^+$.

Example 21

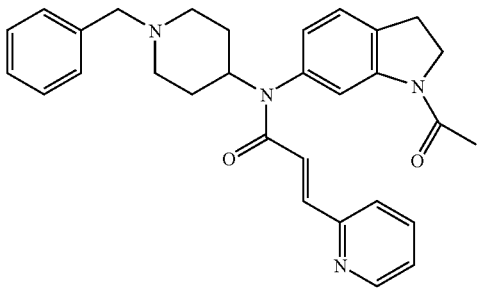

trans-N-(1-Acetyl-2,3-dihydro-1H-indol-6-yl)-N-(1-benzyl-piperidin-4-yl)-3-pyridin-2-yl-acrylamide The title compound (186 mg, 88%) was as in Example 18 using pyridine-2-carbaldehyde in place of 3-phenyl-propenal. $^1$H NMR (500 MHz, CDCl$_3$): 8.47 (br s, 1H), 8.04 (s, 1H), 7.65-7.57 (m, 2H), 7.31-7.11 (m, 8H), 6.76-6.74 (m, 1H), 6.67 (d, J=15.3 Hz, 1H), 4.76-4.71 (m, 1H), 4.15-4.11 (m, 2H), 3.44 (s, 2H), 3.26-3.22 (m, 2H), 2.89 (br s, 2H), 2.21 (s, 3H), 2.15-2.10 (m, 2H), 2H), 1.90-1.76 (m, 2H), 1.62-1.42 (m, 2H). MS: exact mass calculated for C$_{30}$H$_{32}$N$_4$O$_2$, 480.25; m/z found, 481.2 [M+H]$^+$, 503.2 [M+Na]$^+$.

Example 22

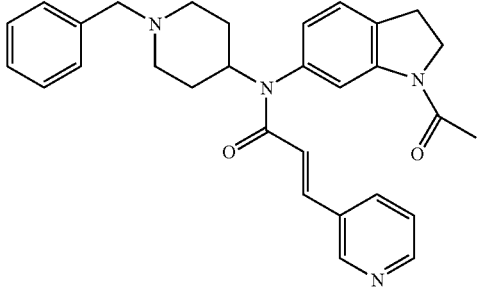

trans-N-(1-Acetyl-2,3-dihydro-1H-indol-6-yl)-N-(1-benzyl-piperidin-4-yl)-3-pyridin-3-yl-acrylamide The title compound (184 mg, 85%) was prepared as in Example 18 using pyridine-3-carbaldehyde in place of 3-phenyl-propenal. $^1$H NMR (500 MHz, CDCl$_3$): 8.55-8.44 (m, 2H), 8.04 (s, 1H), 7.60-7.53 (m, 2H), 7.28-7.17 (m, 7H), 6.75-6.73 (m, 1H), 6.23 (d, J=15.8 Hz, 1H), 4.74-4.69 (m, 1H), 4.18-4.13 (m, 2H), 3.44 (br s, 2H), 3.29-3.24 (m, 2H), 2.89 (br s, 2H), 2.23 (s, 3H), 2.15-2.10 (m, 2H), 1.88-1.78 (m, 2H), 1.55-1.44 (m, 2H). MS: exact mass calculated for C$_{30}$H$_{32}$N$_4$O$_2$, 480.25; m/z found, 481.2 [M+H]$^+$, 503.2 [M+Na]$^+$.

Example 23

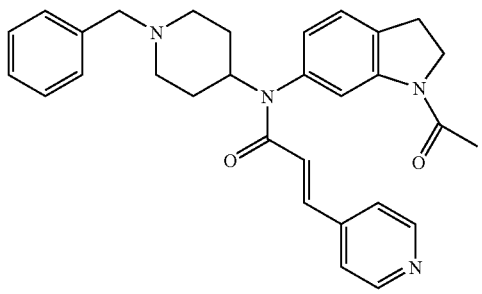

trans-N-(1-Acetyl-2,3-dihydro-1H-indol-6-yl)-N-(1-benzyl-piperidin-4-yl)-3-pyridin-4-yl-acrylamide The title compound (190 mg, 90%) was prepared as in Example 18 using pyridine-4-carbaldehyde in place of 3-phenyl-propenal. $^1$H NMR (500 MHz, CDCl$_3$): 8.50-8.49 (m, 2H), 8.04 (s, 1H), 7.53 (d, J=15.5 Hz, 1H), 7.30-7.18 (m, 6H), 7.10-7.09 (m, 2H), 6.74-6.73 (m, 1H), 6.31 (d, J=15.5 Hz, 1H), 4.73-4.68 (m, 1H), 4.18-4.14 (m, 2H), 3.44 (s, 2H), 3.30-3.25 (m, 2H), 2.89 (br s, 2H), 2.24 (s, 3H), 2.15-2.10 (m, 2H), 1.88-1.77 (m, 2H), 1.54-1.43 (m, 2H). MS: exact mass calculated for C$_{30}$H$_{32}$N$_4$O$_2$, 480.25; m/z found, 481.2 [M+H]$^+$, 503.2 [M+Na]$^+$.

Example 24

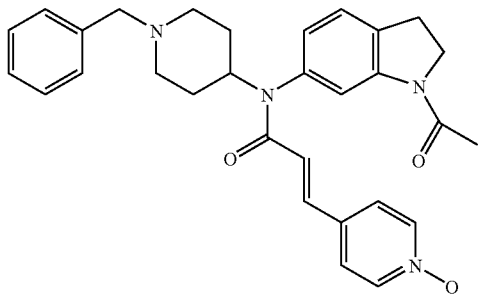

trans-N-(1-Acetyl-2,3-dihydro-1H-indol-6-yl)-N-(1-benzyl-piperidin-4-yl)-3-(1-oxy-pyridin-4-yl)-acrylamide The title compound (194 mg, 89%) was prepared as in Example 18 using 1-oxy-pyridine-4-carbaldehyde in place of 3-phenyl-propenal. $^1$H NMR (500 MHz, CDCl$_3$): 8.04-8.03 (m, 3H), 7.47 (d, J=15.5 Hz, 1H), 7.30-7.19 (m, 6H), 7.10-7.09 (m, 2H), 6.74-6.73 (m, 1H), 6.18 (d, J=15.5 Hz, 1H), 4.69 (br s, 1H), 4.18-4.14 (m, 2H), 3.44 (s, 2H), 3.30-3.25 (m, 2H), 2.88 (br s, 2H), 2.24 (s, 3H), 2.14-2.10

(m, 2H), 1.87-1.76 (m, 2H), 1.54-1.42 (m, 2H). MS: exact mass calculated for $C_{30}H_{32}N_4O_3$, 496.25; m/z found, 497.2 [M+H]$^+$, 519.2 [M+Na]$^+$.

Example 25

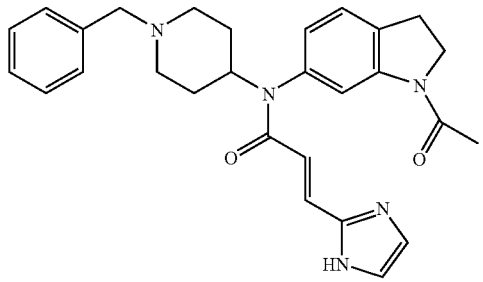

trans-N-(1-Acetyl-2,3-dihydro-1H-indol-6-yl)-N-(1-benzyl-piperidin-4-yl)-3-(1H-imidazol-2-yl)-acrylamide The title compound (154 mg, 75%) was prepared as in Example 18 using 1H-imidazole-2-carbaldehyde in place of 3-phenyl-propenal. $^1$H NMR (500 MHz, CDCl$_3$): 7.98 (br s, 1H), 7.73 (d, J=15.3 Hz, 1H), 7.28-7.19 (m, 5H), 7.00-6.91 (m, 3H), 6.66-6.65 (m, 1H), 6.34 (d, J=15.3 Hz, 1H), 4.63-4.58 (m, 1H), 4.16-4.04 (m, 2H), 3.44 (s, 2H), 3.21-3.12 (m, 2H), 2.91 (br s, 2H), 2.17 (s, 3H), 2.11-2.06 (m, 2H), 1.90-1.77 (m, 2H), 1.56-1.54 (m, 2H). MS: exact mass calculated for $C_{28}H_{31}N_5O_2$, 469.58; m/z found, 470.2 [M+H]$^+$, 492.2 [M+Na]$^+$.

Example 26

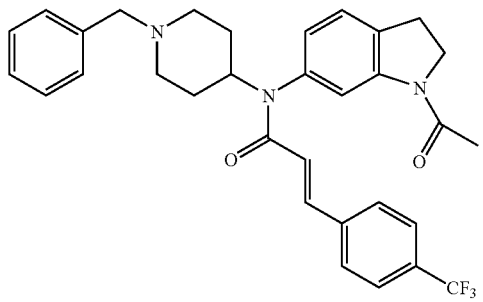

trans-N-(1-Acetyl-2,3-dihydro-1H-indol-6-yl)-N-(1-benzyl-piperidin-4-yl)-3-(4-trifluoromethyl-phenyl)-acrylamide The title compound (49.5 mg, 32%) was prepared as in Example 20 using trans-3-(4-trifluoromethyl-phenyl)-acrylic acid in place of trans-3-thiophen-3-yl-acrylic acid. $^1$H NMR (500 MHz, CDCl$_3$): 8.04 (s, 1H), 7.62 (d, J=15.5 Hz, 1H), 7.50-7.49 (m, 2H), 7.36-7.34 (m, 2H), 7.31-7.18 (m, 6H), 6.75-6.73 (m, 1H), 6.22 (d, J=15.5 Hz, 1H), 4.74-4.69 (m, 1H), 4.17-4.10 (m, 2H), 3.47 (s, 2H), 3.29-3.24 (m, 2H), 2.91 (br s, 2H), 2.23 (s, 3H), 2.19-2.13 (m, 2H), 1.89-1.78 (m, 2H), 1.57-1.45 (m, 2H). MS: exact mass calculated for $C_{32}H_{32}F_3N_3O_2$, 547.24; m/z found, 548.3 [M+H]$^+$, 570.2 [M+Na]$^+$.

Example 27

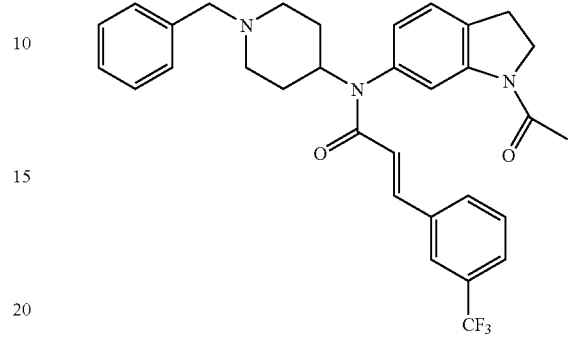

trans-N-(1-Acetyl-2,3-dihydro-1H-indol-6-yl)-N-(1-benzyl-piperidin-4-yl)-3-(3-trifluoromethyl-phenyl)-acrylamide The title compound (80.7 mg, 52%) was prepared as in Example 20 using trans-3-(3-trifluoromethyl-phenyl)-acrylic acid in place of trans-3-thiophen-3-yl-acrylic acid. $^1$H NMR (500 MHz, CDCl$_3$): 8.05 (s, 1H), 7.63 (d, J=15.5 Hz, 1H), 7.50-7.36 (m, 5H), 7.30-7.18 (m, 6H), 6.75-6.74 (m, 1H), 6.19 (d, J=15.5 Hz, 1H), 4.74-4.70 (m, 1H), 4.18-4.11 (m, 2H), 3.45 (s, 2H), 3.30-3.24 (m, 2H), 2.89 (br s, 2H), 2.24 (s, 3H), 2.15-2.11 (m, 2H), 1.89-1.77 (m, 2H), 1.56-1.43 (m, 2H). MS: exact mass calculated for $C_{32}H_{32}F_3N_3O_2$, 547.24; m/z found, 548.3 [M+H]$^+$, 570.2 [M+Na]$^+$.

Example 28

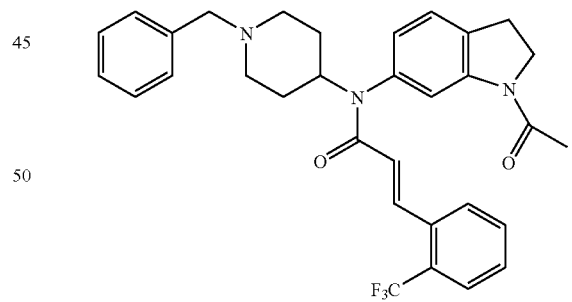

trans-N-(1-Acetyl-2,3-dihydro-1H-indol-6-yl)-N-(1-benzyl-piperidin-4-yl)-3-(2-trifluoromethyl-phenyl)-acrylamide The title compound (144 mg, 92%) was prepared as in Example 20 using trans-3-(2-trifluoromethyl-phenyl)-acrylic acid in place of trans-3-thiophen-3-yl-acrylic acid. $^1$H NMR (500 MHz, CDCl$_3$): 8.05 (s, 1H), 8.00-7.97 (m, 1H), 7.61-7.59 (m, 1H), 7.38-7.15 (m, 9H), 6.74-6.73 (m, 1H), 6.13 (d, J=15.3 Hz, 1H), 4.75-4.70 (m, 1H), 4.14-4.09

(m, 2H), 3.44 (s, 2H), 3.23 (br s, 2H), 2.89 (br s, 2H), 2.22 (s, 3H), 2.14-2.09 (m, 2H), 1.90-1.77 (m, 2H), 1.58-1.42 (m, 2H). MS: exact mass calculated for C$_{32}$H$_{32}$F$_3$N$_3$O$_2$, 547.24; m/z found, 548.3 [M+H]$^+$, 570.2 [M+Na]$^+$.

Example 29

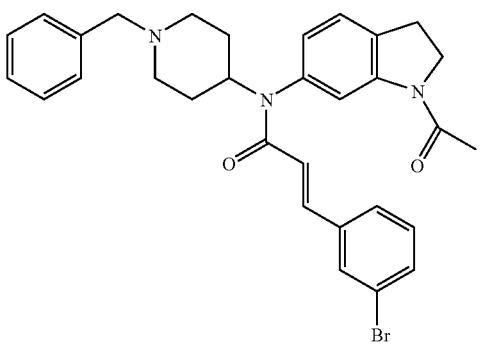

trans-N-(1-Acetyl-2,3-dihydro-1H-indol-6-yl)-N-(1-benzyl-piperidin-4-yl)-3-(3-bromo-phenyl)-acrylamide The title compound (134 mg, 84%) was prepared as in Example 20 using trans-3-(3-bromo-phenyl)-acrylic acid in place of trans-3-thiophen-3-yl-acrylic acid. $^1$H NMR (500 MHz, CDCl$_3$): 8.04 (s, 1H), 7.54 (d, J=15.5 Hz, 1H), 7.37-7.35 (m, 2H), 7.28-7.10 (m, 9H), 6.13 (d, J=15.5 Hz, 1H), 4.74-4.69 (m, 1H), 4.20-4.09 (m, 2H), 3.44 (s, 2H), 3.29-3.23 (m, 2H), 2.90-2.87 (m, 2H), 2.21 (s, 3H), 2.14-2.10 (m, 2H), 1.88-1.76 (m, 2H), 1.55-1.42 (m, 2H). MS: exact mass calculated for C$_{31}$H$_{32}$BrN$_3$O$_2$, 557.17; m/z found, 560.2 [M+H]$^+$.

Example 30

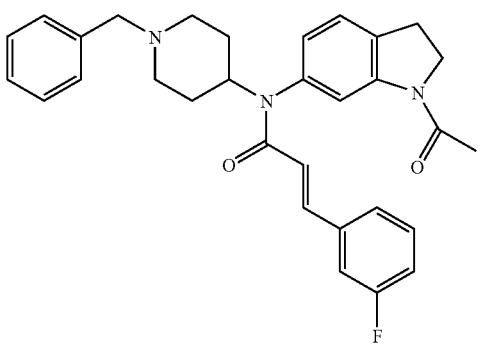

trans-N-(1-Acetyl-2,3-dihydro-1H-indol-6-yl)-N-(1-benzyl-piperidin-4-yl)-3-(3-fluoro-phenyl)-acrylamide The title compound (94 mg, 66%) was prepared as in Example 20 using trans-3-(3-fluoro-phenyl)-acrylic acid in place of trans-3-thiophen-3-yl-acrylic acid. $^1$H NMR (500 MHz, CDCl$_3$): 8.04 (s, 1H), 7.58 (d, J=15.5 Hz, 1H), 7.30-7.17 (m, 8H), 7.06-7.05 (m, 1H), 6.96-6.92 (m, 1H), 6.74-6.73 (m, 1H), 6.14 (d, J=15.5 Hz, 1H), 4.74 (m, 1H), 4.19-4.11 (m, 2H), 3.44 (s, 2H), 3.31-3.24 (m, 2H), 2.91-2.87 (m, 2H), 2.25 (s, 3H), 2.15-2.10 (m, 2H), 1.88-1.76 (m, 2H), 1.55-1.43 (m, 2H). MS: exact mass calculated for C$_{31}$H$_{32}$FN$_3$O$_2$, 497.25; m/z found, 498.2 [M+H]$^+$, 520.2 [M+Na]$^+$.

Example 31

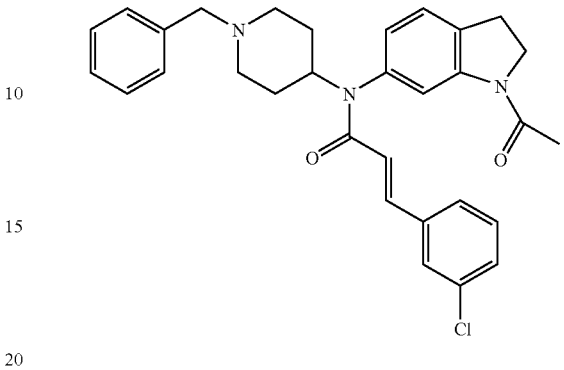

trans-N-(1-Acetyl-2,3-dihydro-1H-indol-6-yl)-N-(1-benzyl-piperidin-4-yl)-3-(3-chloro-phenyl)-acrylamide The title compound (71 mg, 48%) was prepared as in Example 20 using trans-3-(3-chloro-phenyl)-acrylic acid in place of trans-3-thiophen-3-yl-acrylic acid. $^1$H NMR (500 MHz, CDCl$_3$): 8.04 (s, 1H), 7.56 (d, J=15.5 Hz, 1H), 7.28-7.14 (m, 10H), 6.74-6.72 (m, 1H), 6.14 (d, J=15.5 Hz, 1H), 4.74-4.69 (m, 1H), 4.19-4.13 (m 2H), 3.44 (s, 2H), 3.31-3.24 (m, 2H), 2.91-2.87 (m, 2H), 2.24 (s, 3H), 2.15-2.10 (m, 2H), 1.89-1.76 (m, 2H), 1.56-1.42 (m, 2H). MS: exact mass calculated for C$_{31}$H$_{32}$ClN$_3$O$_2$, 513.22; m/z found, 514.2 [M+H]$^+$, 536.2 [M+Na]$^+$.

Example 32

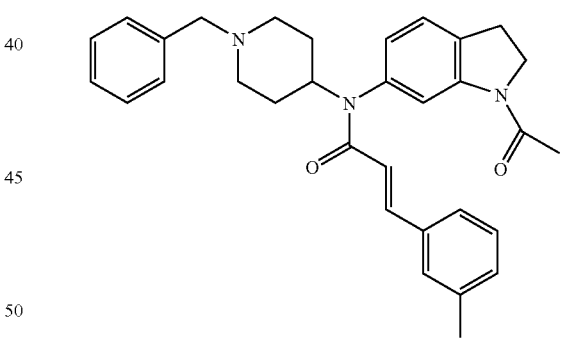

trans-N-(1-Acetyl-2,3-dihydro-1H-indol-6-yl)-N-(1-benzyl-piperidin-4-yl)-3-m-tolyl-acrylamide The title compound (112 mg, 78%) was prepared as in Example 20 using trans-3-m-tolyl-acrylic acid in place of trans-3-thiophen-3-yl-acrylic acid. $^1$H NMR (500 MHz, CDCl$_3$): 8.05 (s, 1H), 7.60 (d, J=15.5 Hz, 1H), 7.28-7.18 (m, 5H), 7.16 (d, J=7.8 Hz, 1H), 7.12 (d, J=7.1 Hz, 1H), 6.74 (d, J=7.9 Hz, 1H), 6.12 (d, J=15.5 Hz, 1H), 4.76-4.71 (m, 1H), 4.16-4.11 (m, 2H), 3.44 (s, 2H), 3.28-3.23 (m, 2H), 2.90-2.85 (m, 2H), 2.28 (s, 3H), 2.23 (s, 3H), 2.12 (t, J=11.4 Hz, 2H), 1.89-1.87 (m, 1H), 1.78-1.76 (m, 1H), 1.55-1.53 (m, 1H), 1.44-1.41 (m, 1H). MS: exact mass calculated for C$_{32}$H$_{35}$N$_3$O$_2$, 493.27; m/z found, 494.2 [M+H]$^+$.

Example 33

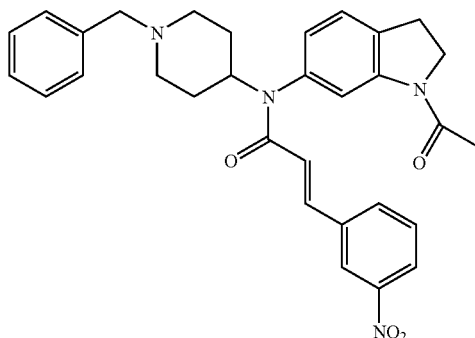

trans-N-(1-Acetyl-2,3-dihydro-1H-indol-6-yl)-N-(1-benzyl-piperidin-4-yl)-3-(3-nitro-phenyl)-acrylamide The title compound (118 mg, 79%) was prepared as in Example 20 using trans-3-(3-nitro-phenyl)-acrylic acid in place of trans-3-thiophen-3-yl-acrylic acid. $^1$H NMR (500 MHz, CDCl$_3$): 8.10-8.05 (m, 2H), 7.65 (d, J=15.5 Hz, 1H), 7.58-7.57 (m, 1H), 7.46-7.43 (m, 1H), 7.30-7.20 (m, 7H), 6.76-6.74 (m, 1H), 6.26 (d, J=15.5 Hz, 1H), 4.74-4.69 (m, 1H), 4.20-4.11 (m, 2H), 3.45 (s, 2H), 3.32-3.23 (m, 2H), 2.90 (br s, 2H), 2.19 (s, 3H), 2.15-2.11 (m, 2H), 1.89-1.78 (m, 2H), 1.56-1.42 (m, 2H). MS: exact mass calculated for C$_{31}$H$_{32}$N$_4$O$_4$, 524.24; m/z found, 525.3 [M+H]$^+$, 547.2 [M+Na]$^+$.

Example 34

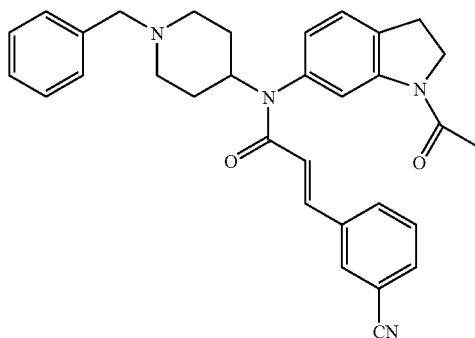

trans-N-(1-Acetyl-2,3-dihydro-1H-indol-6-yl)-N-(1-benzyl-piperidin-4-yl)-3-(3-cyano-phenyl)-acrylamide The title compound (68.4 mg, 72%) was prepared as in Example 20 using trans-3-(3-cyano-phenyl)-acrylic acid in place of trans-3-thiophen-3-yl-acrylic acid. $^1$H NMR (500 MHz, CDCl$_3$): 8.05 (s, 1H), 7.58 (d, J=15.5 Hz, 1H), 7.53-7.48 (m, 3H), 7.40-7.37 (m, 1H), 7.28-7.20 (m, 6H), 6.75-6.73 (m, 1H), 6.20 (d, J=15.5 Hz, 1H), 4.73-4.69 (m, 1H), 4.23-4.13 (m, 2H), 3.45 (s, 2H), 3.37-3.26 (m, 2H), 2.89 (br s, 2H), 2.25 (s, 3H), 2.15-2.10 (m, 2H), 1.88-1.77 (m, 2H), 1.55-1.44 (m, 2H). MS: exact mass calculated for C$_{32}$H$_{32}$N$_4$O$_2$, 504.25; m/z found, 505.2 [M+H]$^+$, 527.2 [M+Na]$^+$.

Example 35

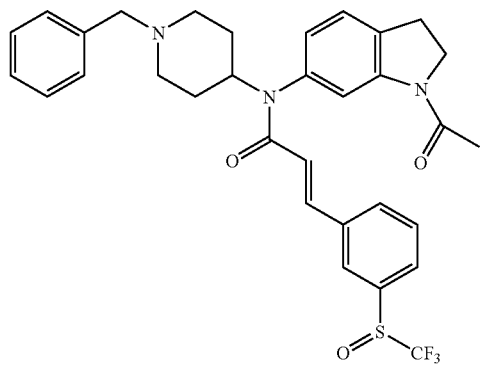

trans-N-(1-Acetyl-2,3-dihydro-1H-indol-6-yl)-N-(1-benzyl-piperidin-4-yl)-3-(3-trifluoromethanesulfinyl-phenyl)-acrylamide The title compound (66 mg, 55%) was prepared as in Example 18 using 3-(3-trifluoromethanesulfinyl-phenyl)-propenal in place of 3-phenyl-propenal. $^1$H NMR (500 MHz, CDCl$_3$): 8.05 (s, 1H), 7.65-7.62 (m, 3H), 7.53-7.48 (m, 2H), 7.28-7.18 (m, 6H), 6.74 (d, J=7.4 Hz, 1H), 6.23 (d, J=15.0 Hz, 1H), 4.74-4.69 (m, 1H), 4.18-4.13 (m, 2H), 3.45 (s, 2H), 3.30-3.24 (m, 2H), 2.94-2.84 (m, 2H), 2.23 (s, 3H), 2.13 (t, J=10.4 Hz, 2H), 1.89-1.86 (m, 1H), 1.79-1.77 (m, 1H), 1.58-1.52 (m, 1H), 1.48-1.43 (m, 1H). MS: exact mass calculated for C$_{32}$H$_{32}$F$_3$N$_3$O$_3$S, 595.21; m/z found, 596.2 [M+H].

Example 36

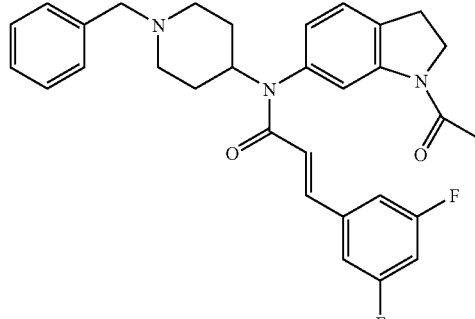

trans-N-(1-Acetyl-2,3-dihydro-1H-indol-6-yl)-N-(1-benzyl-piperidin-4-yl)-3-(3,5-difluoro-phenyl)-acrylamide The title compound (151 mg, 100%) was prepared as in Example 20 using trans-3-(3,5-difluoro-phenyl)-acrylic acid in place of trans-3-thiophen-3-yl-acrylic acid. $^1$H NMR (500 MHz, CDCl$_3$): 8.04 (s, 1H), 7.51 (d, J=15.5 Hz, 1H), 7.33-7.23 (m, 6H), 6.77-6.68 (m, 4H), 6.14 (d, J=15.5 Hz, 1H), 4.73-4.68 (m, 1H), 4.20-4.14 (m, 2H), 3.44 (s, 2H), 3.32-3.25 (m, 2H), 2.91-2.87 (m, 2H), 2.24 (s, 3H), 2.15-2.10 (m, 2H), 1.88-1.76 (m, 2H), 1.55-1.42 (m, 2H). MS: exact mass calculated for C$_{31}$H$_{31}$F$_2$N$_3$O$_2$, 515.24; m/z found, 516.3 [M+H]$^+$, 538.3 [M+Na]$^+$.

Example 37

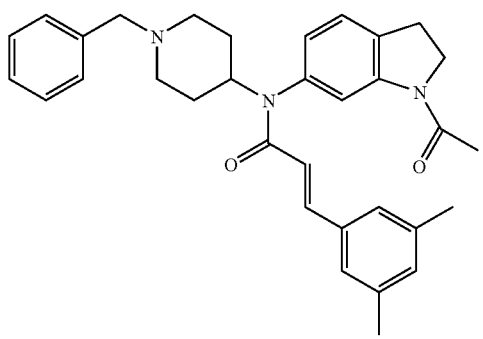

trans-N-(1-Acetyl-2,3-dihydro-1H-indol-6-yl)-N-(1-benzyl-piperidin-4-yl)-3-(3,5-dimethyl-phenyl)-acrylamide The title compound (67 mg, 70%) was prepared as in Example 20 using trans-3-(3,5-dimethyl-phenyl)-acrylic acid in place of trans-3-thiophen-3-yl-acrylic acid. $^1$H NMR (500 MHz, CDCl$_3$): 8.05 (s, 1H), 7.57 (d, J=15.5 Hz, 1H), 7.28-7.16 (m, 6H), 6.89-6.88 (m, 3H), 6.74-6.73 (m, 1H), 6.10 (d, J=15.5 Hz, 1H), 4.76-4.71 (m, 1H), 4.17-4.11 (m, 2H), 3.44 (s, 2H), 3.28-3.23 (m, 2H), 2.88 (br s, 2H), 2.24 (s, 9H), 2.15-2.10 (m, 2H), 1.90-1.75 (m, 2H), 1.56-1.40 (m, 2H). MS: exact mass calculated for C$_{33}$H$_{37}$N$_3$O$_2$, 507.29; m/z found, 508.3 [M+H]$^+$, 530.2 [M+Na]$^+$.

Example 38

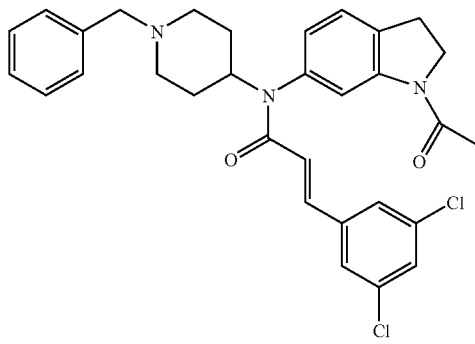

trans-N-(1-Acetyl-2,3-dihydro-1H-indol-6-yl)-N-(1-benzyl-piperidin-4-yl)-3-(3,5-dichloro-phenyl)-acrylamide The title compound (68.3 mg, 65%) was prepared as in Example 20 using trans-3-(3,5-dichloro-phenyl)-acrylic acid in place of trans-3-thiophen-3-yl-acrylic acid. $^1$H NMR (500 MHz, CDCl$_3$): 8.04 (s, 1H), 7.48 (d, J=15.5 Hz, 1H), 7.28-7.19 (m, 7H), 7.12 (s, 2H), 6.73-6.72 (m, 1H), 6.14 (d, J=15.5 Hz, 1H), 4.72-4.67 (m, 1H), 4.21-4.14 (m, 2H), 3.44 (s, 2H), 3.32-3.25 (m, 2H), 2.91-2.87 (m, 2H), 2.24 (s, 3H), 2.14-2.10 (m, 2H), 1.88-1.75 (m, 2H), 1.55-1.42 (m, 2H). MS: exact mass calculated for C$_{31}$H$_{31}$Cl$_2$N$_3$O$_2$, 547.18; m/z found, 548.2 [M+H]$^+$, 550.2 [M+H]$^+$, 570.2 [M+Na]$^+$.

Example 39

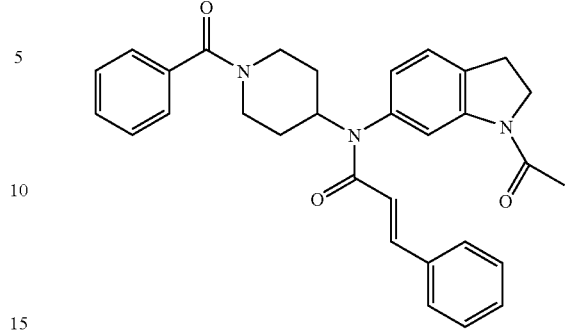

trans-N-(1-Acetyl-2,3-dihydro-1H-indol-6-yl)-N-(1-benzoyl-piperidin-4-yl)-3-phenyl-acrylamide Step A. 1-[6-(1-Benzoyl-piperidin-4-ylamino)-2,3-dihydro-indol-1-yl]-ethanone. To a solution of 1-benzoyl-4-piperidone (250 mg, 1.2 mmol) and 1-acetyl-6-aminoindoline (220 mg, 1.2 mmol), in CH$_2$Cl$_2$ (0.2 M) was added AcOH (73 µL, 1.2 mmol), followed by Na(OAc)$_3$BH (390 mg, 1.8 mmol). The resulting solution was allowed to stir overnight. The reaction was quenched by the addition of satd. aq. NaHCO$_3$ and CH$_2$Cl$_2$. The layers were separated, and the organic portion was washed with brine, dried with Na$_2$SO$_4$ and concentrated. Purification by silica gel chromatography (1 to 5% MeOH/CH$_2$Cl$_2$) provided the desired intermediate (132 mg, 30%).

Step B. The product from Step A (93 mg, 0.26 mmol) was acylated as in Example 2, Step C to provide the title compound (43 mg, 34%). $^1$H NMR (500 MHz, CDCl$_3$): 8.09-7.98 (br m, 1H), 7.63 (d, J=15.5 Hz, 1H), 7.49-7.03 (m, 11H), 6.80-6.61 (br m, 1H), 6.14 (d, J=15.5 Hz, 1H), 5.01-4.90 (m, 1H), 4.83-4.68 (br m, 1H), 3.85-3.72 (br m, 1H), 3.22-3.08 (br m, 2H), 2.92-2.78 (br m, 1H), 2.05-1.78 (br m, 3H), 1.51-1.29 (br m, 3H). MS: exact mass calculated for C$_{31}$H$_{31}$N$_3$O$_3$, 493.24; m/z found, 494.2 [M+H]$^+$.

Example 40

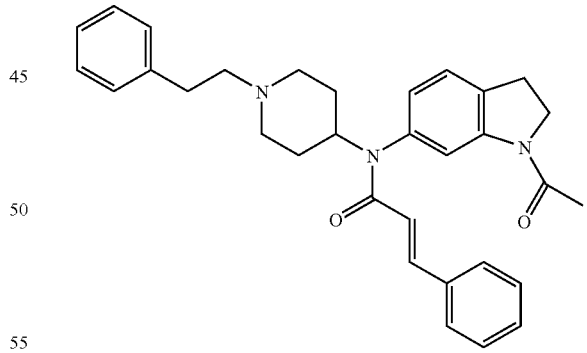

trans-N-(1-Acetyl-2,3-dihydro-1H-indol-6-yl)-N-(1-phenethyl-piperidin-4-yl)-3-phenyl-acrylamide Step A. 1-[6-(1-Phenethyl-piperidin-4-ylamino)-2,3-dihydro-indol-1-yl]-ethanone. The desired compound (133 mg, 64%) was prepared as in Example 39, Step A, employing 1-phenethylpiperidone in place of 1-benzoyl-4-piperidone and using 1,2-dichloroethane as the solvent. $^1$H NMR (500 MHz, CDCl$_3$): 7.64 (d, J=1.4 Hz, 1H), 7.31-7.20 (m, 2H), 7.20-7.15 (m, 3H), 6.94 (d, J=7.9 Hz, 1H), 6.27 (dd, J=8.2, 1.8 Hz, 1H), 4.06-3.95 (m, 2H), 3.39-3.29 (m, 1H), 3.10-

3.02 (m, 2H), 2.97-2.90 (m, 2H), 2.84-2.77 (m, 2H), 2.63-2.57 (m, 2H), 2.20 (s, 3H), 2.25-2.18 (m, 2H), 2.12-2.02 (m, 2H), 1.55-1.40 (m, 2H). MS: exact mass calculated for $C_{23}H_{29}N_3O$, 363.23; m/z found, 364.2 [M+H]$^+$.

Step B. The title compound (45 mg, 67%) was prepared from the product of Step A (50 mg, 0.1 mmol) as in Example 2, Step C. $^1$H NMR (500 MHz, CDCl$_3$): 8.65 (s, 1H), 7.63 (d, J=15.5 Hz, 1H), 7.30-7.22 (m, 7H), 7.20-7.12 (m, 4H), 6.76 (dd, J=8.2, 1.4 Hz, 1H), 6.18 (d, J=15.5 Hz, 1H), 4.80-4.70 (m, 1H), 4.14 (dd, J=16.8, 8.0 Hz, 2H), 3.31-3.19 (m, 2H), 3.07-2.95 (m, 2H), 2.78-2.60 (m, 2H), 2.58-2.50 (m, 2H), 2.23 (s, 3H), 2.21-2.15 (m, 2H), 1.98-1.81 (m, 2H), 1.65-1.46 (m, 2H). MS: exact mass calculated for $C_{32}H_{35}N_3O_2$, 493.27; m/z found, 494.2 [M+H]$^+$.

Example 41

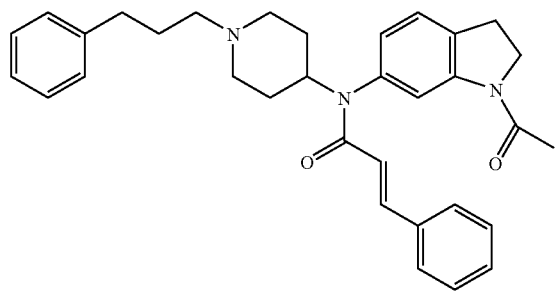

trans-N-(1-Acetyl-2,3-dihydro-1H-indol-6-yl)-3-phenyl-N-[1-(3-phenyl-propyl)-piperidin-4-yl]-acrylamide Step A. 4-(1-Acetyl-2,3-dihydro-1H-indol-6-ylamino)-piperidine-1-carboxylic acid tert-butyl ester. The desired ester (2.37 g, 68%) was prepared as in Example 39, using 4-oxo-piperidine-1-carboxylic acid tert-butyl ester (3.9 g, 19 mmol), 1-acetyl-6-aminoindoline (1.7 g, 9.8 mmol), Na(OAc)$_3$BH (6.2 g, 29 mmol) and AcOH (3 mL, 50 mmol) in 1,2-dichloroethane (50 mL).

Step B. trans-4-[(1-Acetyl-2,3-dihydro-1H-indol-6-yl)-(3-phenyl-acryloyl)-amino]-piperidine-1-carboxylic acid tert-butyl ester. The title compound (2.26 g, 70%) was made from the product of Step A, as described in Example 2, Step C. $^1$H NMR (500 MHz, CDCl$_3$): 8.04 (s, 1H), 7.64 (d, J=15.5 Hz, 1H), 7.36-7.21 (m, 5H), 7.19 (d, J=7.7 Hz, 1H), 6.74 (dd, J=8.4, 1.3 Hz, 1H), 6.15 (d, J=15.5 Hz, 1H), 4.90-4.80 (m, 1H), 4.21-3.98 (m, 4H), 3.33-3.21 (m, 2H), 2.90-2.75 (m, 2H), 2.24 (s, 3H), 1.96-1.72 (m, 2H), 1.49-1.31 (m, 2H), 1.40 (s, 9H). MS: exact mass calculated for $C_{29}H_{35}N_3O_4$, 489.26; m/z found, 512.3 [M+Na]$^+$.

Step C. trans-N-(1-Acetyl-2,3-dihydro-1H-indol-6-yl)-3-phenyl-N-piperidin-4-yl-acrylamide. The product from Step B (100 mg, 0.2 mmol) was dissolved in 2 mL of CH$_2$Cl$_2$ and then TFA (2 mL) was added. After stirring for 1 h, the reaction mixture was concentrated under reduced pressure to provide the desired product (80 mg, 69%). $^1$H NMR (500 MHz, CDCl$_3$): 9.20-9.14 (m, 1H), 8.61-8.49 (m, 1H), 8.00 (s, 1H), 7.64 (d, J=15.5 Hz, 1H), 7.32-7.27 (m, 5H), 7.23 (d, J=7.8 Hz, 1H), 7.67 (d, J=6.7 Hz, 1H), 6.17 (d, J=15.5 Hz, 1H), 4.97-4.85 (m, 1H), 4.21-4.15 (m, 2H), 3.54-3.35 (m, 2H), 3.21-3.16 (m, 2H), 3.07-2.93 (m, 2H), 2.24 (s, 3H), 2.16-1.95 (m, 2H), 1.82-162 (m, 2H). MS: exact mass calculated for $C_{24}H_{27}N_3O_2$, 389.21; n/z found, 390.3 [M+H]$^+$.

Step D. To a solution of 4-phenyl-butyraldehyde (104 mg, 0.780 mmol) and the acrylamide from Step C (232 mg, 0.60 mmol) in CH$_2$Cl$_2$ (0.2 M) was added Na(OAc)$_3$BH (160 mg, 0.78 mmol). The resulting mixture was allowed to stir overnight. The reaction was quenched by the addition of satd. aq. NaHCO$_3$ and CH$_2$Cl$_2$. The layers were separated, and the organic portion was extracted with brine, dried with Na$_2$SO$_4$, and concentrated. Purification by silica gel chromatography (1 to 5% MeOH/CH$_2$Cl$_2$) provided 77 mg (25%) of the desired product. $^1$H NMR (500 MHz, CDCl$_3$): 7.93 (d, J=1.8 Hz, 1H), 7.56 (d, J=15.4 Hz, 1H), 7.25-7.10 (m, 10H), 7.07 (dd, J=8.3, 1.5 Hz, 1H), 6.68 (dd, J=7.8, 2.0 Hz, 1H), 6.10 (d, J=15.6 Hz, 1H), 4.83-4.68 (m, 1H), 4.15-4.02 (m, 2H), 3.25-3.15 (m, 2H), 2.62-2.53 (m, 4H), 2.16 (s, 3H), 2.08-1.81 (m, 10H). MS: exact mass calculated for $C_{33}H_{37}N_3O_2$, 507.29; m/z found, 508.4 [M+H]$^+$.

Example 42

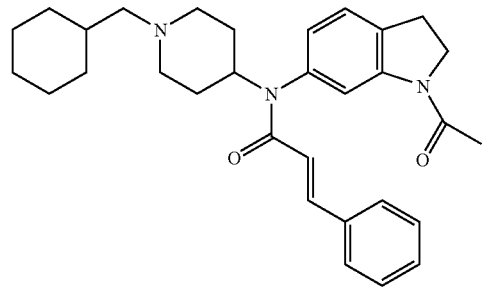

trans-N-(1-Acetyl-2,3-dihydro-1H-indol-6-yl)-N-(1-cyclohexylmethyl-piperidin-4-yl)-3-phenyl-acrylamide The title compound (238 mg, 50%) was prepared as in Example 41, Step D, employing cyclohexane-carboxaldehyde in place of 4-phenylbutyraldehyde. $^1$H NMR (500 MHz, CDCl$_3$): 7.91 (s, 1H), 7.52 (d, J=15.4 Hz, 1H), 7.21-7.12 (m, 5H), 7.09 (d, J=8.1 Hz, 1H), 6.64 (dd, J=7.8, 2.0 Hz, 1H), 6.06 (d, J=15.6 Hz, 1H), 4.80-4.50 (m, 1H), 4.04 (t, J=8.6 Hz, 2H), 3.19-2.84 (m, 4H), 2.32-2.01 (m, 3H), 1.88 (s, 3H), 1.83-1.70 (m, 2H), 1.69-1.44 (m, 8H), 1.18-0.93 (m, 4H), 0.89-0.62 (m, 2H). MS: exact mass calculated for $C_{31}H_{39}N_3O_2$, 485.30; m/z found, 486.4 [M+H]$^+$.

Example 43

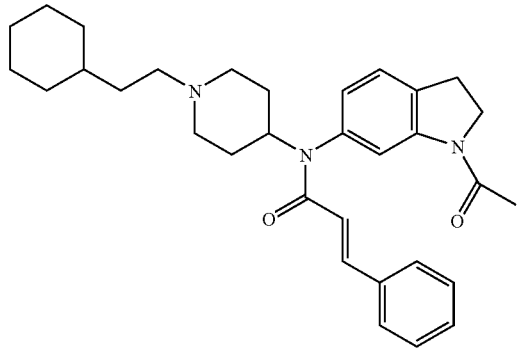

trans-N-(1-Acetyl-2,3-dihydro-1H-indol-6-yl)-N-[1-(2-cyclohexyl-ethyl)-piperidin-4-yl]-3-phenyl-acrylamide The title compound (67 mg, 54%) was prepared as in Example 41, Step D, employing cyclohexyl-acetaldehyde in place of 4-phenylbutyraldehyde. ¹H NMR (500 MHz, CDCl₃): 7.97 (s, 1H), 7.56 (d, J=15.4 Hz, 1H), 7.25-7.15 (m, 5H), 7.10 (d, J=8.3 Hz, 1H), 6.68 (dd, J=7.8, 1.5 Hz, 1H), 6.10 (d, J=15.7 Hz, 1H), 4.78-4.58 (br m, 1H), 4.13-3.98 (m, 2H), 3.28-3.08 (m, 2H), 2.98-2.80 (m, 2H), 2.35-2.19 (m, 2H), 2.16 (s, 3H), 2.10-1.91 (m, 3H), 1.87-1.69 (m, 2H), 1.64-1.49 (m, 5H), 1.33-1.20 (m, 2H), 1.99-0.98 (m, 5H), 0.90-0.71 (m, 2H). MS: exact mass calculated for C₃₂H₄₁N₃O₂, 499.32; m/z found, 500.4 [M+H]⁺.

Example 44

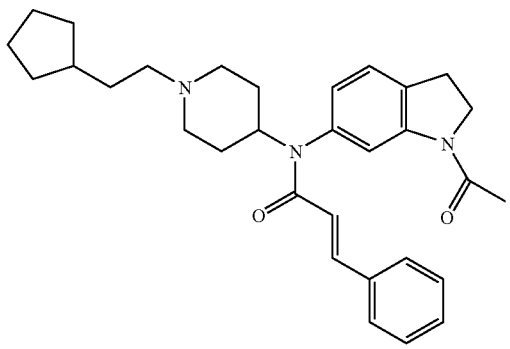

trans-N-(1-Acetyl-2,3-dihydro-1H-indol-6-yl)-N-[1-(2-cyclopentyl-ethyl)-piperidin-4-yl]-3-phenyl-acrylamide The title compound (53 mg, 37%) was prepared as in Example 41, Step D, employing cyclopentyl-acetaldehyde in place of 4-phenylbutyraldehyde. ¹H NMR (500 MHz, CDCl₃): 7.90-7.85 (br m, 1H), 7.56 (d, J=15.6 Hz, 1H), 6.69 (br d, J=7.9 Hz, 1H), 6.10 (d, J=15.9 Hz,1H), 4.74-4.66 (br m, 1H), 4.11-4.04 (br m, 2H), 3.23-3.14 (m, 2H), 3.10-2.91 (m, 2H), 2.16 (s, 3H), 1.91-1.70 (m, 4H), 1.71-1.61 (m, 3H), 1.62-1.29 (m, 8H), 1.14-0.97 (m, 4H). MS: exact mass calculated for C₃₁H₃₉N₃O₂, 485.30; m/z found, 486.5 [M+H]⁺.

Example 45

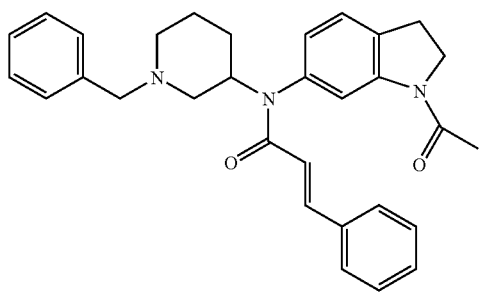

trans-N-(1-Acetyl-2,3-dihydro-1H-indol-6-yl)-N-(1-benzyl-piperidin-3-yl)-3-phenyl-acrylamide Step A. 1-[6-(1-Benzyl-piperidin-3-ylamino)-2,3-dihydro-indol-1-yl]-ethanone. The desired intermediate (116 mg, 30%) was prepared as in Example 39, Step A, employing 1-benzyl-3-piperidone (510 mg, 4.4 mmol), 1-acetyl-6-aminoindoline (200 mg, 1 mmol), Na(OAc)₃BH (910 mg, 4.3 mmol), and AcOH (340 µL, 5.4 mmol) in 1,2-dichloroethane (20 mL).

Step B. The above intermediate (0.10 g, 0.29 mmol) was then reacted with cinnamoyl chloride (62 mg, 0.37 mmol) as in Example 2, Step C to provide 145 mg (99%) of the desired product. ¹H NMR (500 MHz, CDCl₃): 8.04 (s, 1H), 7.62 (d, J=15.5 Hz, 1H), 7.30-7.18 (m, 10H), 7.15 (d, J=7.8 Hz, 1H), 6.74 (dd, J=7.3, 1.4 Hz, 1H), 6.16 (d, J=15.5 Hz, 1H), 4.79-4.68 (m, 1H), 4.18-4.07 (m, 2H), 3.30-3.15 (m, 2H), 2.98-2.85 (m, 2H), 2.26-2.23 (m, 2H), 2.21 (s, 3H), 2.15-2.01 (m, 2H), 1.93-1.75 (m, 2H), 1.60-1.35 (m, 3H). MS: exact mass calculated for C₃₁H₃₃N₃O₂, 479.26; m/z found, 480.2 [M+H]⁺.

Example 46

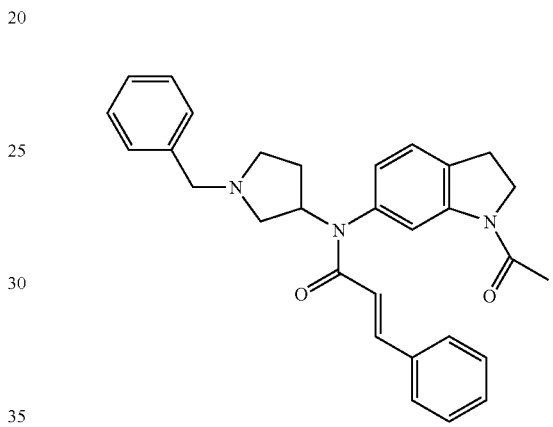

trans-N-(1-Acetyl-2,3-dihydro-1H-indol-6-yl)-N-(1-benzyl-pyrrolidin-3-yl)-3-phenyl-acrylamide Step A. 1-[6-(1-benzyl-pyrrolidin-3-ylamino)-2,3-dihydro-indol-1-yl]-ethanone. The desired intermediate (84 mg, 44%) was prepared as in Example 39, Step A, using 1-benzyl-3-pyrrolidinone (0.20 g, 1.1 mmol), 1-acetyl-6-aminoindoline (0.10 g, 0.57 mmol), Na(OAc)₃BH (360 mg, 1.7 mmol), and AcOH (171 µL, 3.0 mmol) in 1,2-dichloroethane (10 mL). ¹H NMR (500 MHz, CDCl₃): 7.61 (s, 1H), 7.35-7.28 (m, 4H), 7.28-7.20 (m, 1H), 6.93 (d, J=8.1 Hz,1H), 6.24 (dd, J=8.2, 1.9 Hz, 1H), 4.05-3.96 (m, 3H), 3.68-3.56 (m, 2H), 3.10-3.01 (m, 2H), 2.80-2.71 (m, 2H), 2.59-2.51 (m, 1H), 2.48-2.39 (m, 1H), 2.38-2.22 (m, 1H), 2.20 (s, 3H), 1.71-1.56 (m, 1H). MS: exact mass calculated for C₂₁H₂₅N₃O, 335.20; m/z found, 336.1 [M+H]⁺.

Step B. The above intermediate (49 mg, 0.29 mmol) was reacted with with cinnamoyl chloride (2 76 mg, 0.2 mmol) as in Example 2, Step C to provide 79 mg (74%) of the desired product. ¹H NMR (500 MHz, CDCl₃): 8.09 (s, 1H), 7.62 (d, J=15.5 Hz, 1H), 7.30-7.15 (m, 1H), 6.78 (d, J=7.0 Hz, 1H), 6.17 (d, J=15.5 Hz, 1H), 5.15-5.05 (br m, 1H), 4.19-4.08 (m, 2H), 3.70-3.51 (m, 2H), 3.29-3.20 (m, 2H), 3.07-2.95 (br m, 1H), 2.76-2.57 (br m, 3H), 2.30-2.22 (m, 1H), 2.21 (s, 3H), 1.98-1.83 (m, 1H). MS: exact mass calculated for C₃₀H₃₁N₃O₂, 465.24; m/z found, 466.2 [M+H]⁺.

Example 47

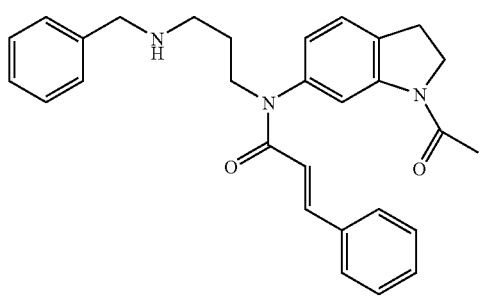

trans-N-(1-Acetyl-2,3-dihydro-1H-indol-6-yl)-N-(3-benzylamino-propyl)-3-phenyl-acrylamide Step A. [3-(1-Acetyl-2,3-dihydro-1H-indol-6-ylamino)-propyl]-carbamic acid tert-butyl ester. A mixture of 1-(6-amino-2,3-dihydro-indol-1-yl)-ethanone (837 mg, 4.8 mmol), (3-bromo-propyl)-carbamic acid tert-butyl ester (1.1 g, 4.8 mmol) and $K_2CO_3$ (1.3 g, 9.5 mmol) in acetonitrile (15 mL) was heated at reflux for 48 h. A white precipitate was filtered off and the filtrate was concentrated under reduced pressure. The residue was purified on silica gel (50% EtOAc/hexanes) to give the desired product as a white solid (320 mg, 20%).

Step B. trans-{3-[(1-Acetyl-2,3-dihydro-1H-indol-6-yl)-(3-phenyl-acryloyl)-amino]-propyl}-carbamic acid tert-butyl ester. The ester from Step A (270 mg, 0.80 mmol) was acylated with cinnamoyl chloride (203 mg, 1.2 mmol) as in Example 2, Step C to provide the desired ester (345 mg, 92%).

Step C. trans-N-(1-acetyl-2,3-dihydro-1H-indol-6-yl)-N-(3-amino-propyl)-3-phenyl-acrylamide. The ester from Step B (345 mg, 0.7 mmol) was dissolved in $CH_2Cl_2$ (5.0 mL) and was treated with TFA (2.5 mL). After 3 h, the reaction mixture was concentrated. The resulting salt was diluted with EtOAc and treated with 1 N NaOH until pH 10 was achieved. The organic layer was then separated and concentrated under reduced pressure to give the desired amine (268 mg, 100%), which was used without further purification.

Step D. trans-N-(1-Acetyl-2,3-dihydro-1H-indol-6-yl)-N-(3-benzylamino-propyl)-3-phenyl-acrylamide. The primary amine from Step C (268 mg, 0.74 mmol) and benzaldehyde (0.08 mL, 0.74 mmol) were dissolved in MeOH and the resulting reaction mixture was stirred at rt for 20 h. Sodium borohydride (45 mg, 1.2 mmol) was added. After 10 min, the reaction mixture was quenched with 1 N NaOH and then extracted with EtOAc. The organic layer was concentrated under reduced pressure. The crude product was purified on silica gel (EtOAc) to give the title compound (235 mg, 70%). $^1$H NMR (500 MHz, CDCl$_3$): 8.14 (s, 1H), 7.65 (d, J=15.5 Hz, 1H), 7.31-7.29 (m, 5H), 7.27-7.26 (m, 5H), 7.17 (d, J=7.9Hz, 1H), 6.78 (d, J=7.1 Hz, 1H), 6.32 (d, J=15.5 Hz, 1H), 4.15 (t, J=8.4 Hz, 2H), 3.91 (br s, 2H), 3.76 (s, 2H), 3.25 (t, J=8.5 Hz, 2H), 2.66 (t, J=6.9 Hz, 2H), 2.24 (s, 3H), 1.80-1.74 (m, 2H). MS: exact mass calculated for $C_{29}H_{31}N_3O_2$, 453.24; m/z found, 454.2 [M+H]$^+$.

Example 48

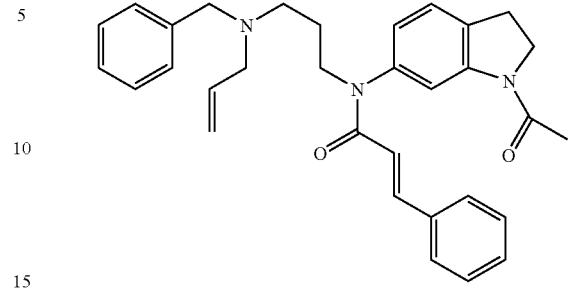

trans-N-(1-Acetyl-2,3-dihydro-1H-indol-6-yl)-N-[3-(allyl-benzyl-amino)-propyl]-3-phenyl-acrylamide A mixture of trans-N-(1-acetyl-2,3-dihydro-1H-indol-6-yl)-N-(3-benzylamino-propyl)-3-phenyl-acrylamide (Example 47, 39 mg, 0.090 mmol), allyl iodide (0.01 mL, 0.1 mmol), and diisopropylethylamine (0.03 mL, 0.2 mmol) in $CH_2Cl_2$ (3.0 mL) was stirred at rt for 20 h. The reaction mixture was concentrated under reduced pressure and the crude product was purified on silica gel (60% EtOAc/hexanes) to provide the title compound (37 mg, 87%). $^1$H NMR (500 MHz, CDCl$_3$): 8.13 (s, 1H), 7.65 (d, J=15.5 Hz, 1H), 7.31-7.24 (m, 10H), 7.15 (d, J=7.6 Hz, 1H), 6.71 (d, J=7.3 Hz, 1H), 6.30 (d, J=16.5 Hz, 1H), 5.84-5.80 (m, 1H), 5.10 (dd, J=17.0, 10.1 Hz, 2H), 4.11 (t, J=7.3 Hz, 2H), 3.84 (br s, 2H), 3.50 (s, 2H), 3.24 (t, J=8.5 Hz, 2H), 3.02 (d, J=6.3 Hz, 2H), 2.46 (t, J=7.1 Hz, 2H), 2.23 (s, 3H), 1.81-1.75 (m, 2H). MS: exact mass calculated for $C_{32}H_{35}N_3O_2$, 493.64; m/z found, 494.2 [M+H]$^+$.

Example 49

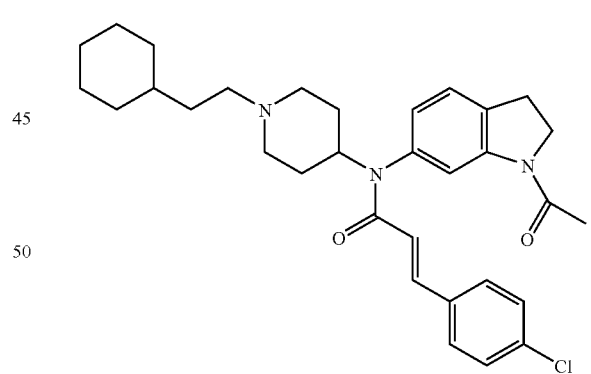

trans-N-(1-Acetyl-2,3-dihydro-1H-indol-6-yl)-3-(4-chloro-phenyl)-N-[1-(2-cyclohexyl-ethyl)-piperidin-4-yl]-acrylamide Step A. trans-4-{(1-Acetyl-2,3-dihydro-1H-indol-6-yl)-[3-(4-chloro-phenyl)-acryloyl]-amino}-piperidine-1-carboxylic acid tert-butyl ester. The ester (1.26 g, 87%) was prepared as in Example 20 using trans-3-(4-chloro-phenyl)-acrylic acid in place of trans-3-thiophen-3-yl-acrylic acid and 4-(1-acetyl-2,3-dihydro-1H-ylamino)-piperidine-1-carboxylic acid tert-butyl ester (Example 41, Step A) in place of 1-[6-(1-benzyl-piperidin-4-ylamino)-2,3-dihydro-indol-1-yl]-ethanone. $^1$H NMR (500 MHz, CDCl$_3$): 8.02 (s, 1H), 7.56 (d, J=15.5 Hz, 1H), 7.21-7.17 (m, 5H), 6.73-6.71 (m, 1H), 6.10 (d, J=15.5 Hz, 1H), 4.84-4.79 (m, 1H), 4.17-4.12 (m, 4H), 3.29-3.24 (m, 2H), 2.80 (br s, 2H), 2.23 (s, 3H), 1.90-1.77 (m, 2H), 1.51-1.27 (m, 11H). MS: exact mass calculated for C$_{29}$H$_{34}$ClN$_3$O$_4$, 523.22; m/z found, 546.2 [M+Na]$^+$, 548.2 [M+Na]$^+$.

Step B. trans-N-(1-Acetyl-2,3-dihydro-1H-indol-6-yl)-3-(4-chloro-phenyl)-N-piperidin-4-yl-acrylamide. The intermediate from Step A (1.22 g, 2.32 mmol) was dissolved in CH$_2$Cl$_2$ (10 mL) and was treated with TFA (10 mL). The mixture was stirred for 30 min at rt and then was concentrated in vacuo. The residue was dissolved in CH$_2$Cl$_2$ and treated with Dowex 550A resin. After stirring for several hours, the mixture was filtered and concentrated in vacuo to give 966 mg (98%) of the desired compound, which was taken on to the next step without further purification.

Step C. The title compound (54 mg, 61%) was prepared from the intermediate from Step B (70.0 mg, 0.165 mmol) as in Example 43, using 1,2-dichloroethane as the solvent. $^1$H NMR (500 MHz, CDCl$_3$): 8.04 (s, 1H), 7.57 (d, J=15.5 Hz, 1H), 7.30-7.16 (m, 5H), 6.75 (br s, 1H), 6.14 (d, J=15.5 Hz, 1H), 4.75 (br s, 1H), 4.17-4.14 (m, 2H) 3.53-3.27 (m, 4H), 2.92 (br s, 2H), 2.28-2.23 (m, 4H), 2.07-2.04 (m, 2H), 1.66-1.43 (m, 9H), 1.29-1.11 (m, 5H), 0.89-0.86 (m, 2H). MS: exact mass calculated for C$_{32}$H$_{40}$ClN$_3$O$_2$, 533.28; m/z found, 534.2 [M+H]$^+$, 556.3 [M+Na]$^+$.

Example 50

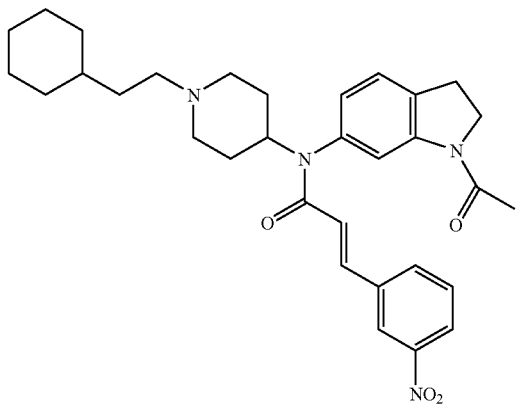

trans-N-(1-Acetyl-2,3-dihydro-1H-indol-6-yl)-N-[1-(2-cyclohexyl-ethyl)-piperidin-4-yl]-3-(3-nitro-phenyl)-acrylamide The title compound (54 mg, 62%) was prepared as in Example 49, using trans-3-(3-nitro-phenyl)-acrylic acid in place of trans-3-(4-chloro-phenyl)-acrylic acid. $^1$H NMR (500 MHz, CDCl$_3$): 8.10-8.05 (m, 3H), 7.66 (d, J=15.5 Hz, 1H), 7.59-7.57 (m, 1H), 7.46-7.43 (m, 1H), 7.21-7.19 (m, 1H), 6.77-6.75 (m, 1H), 6.28 (d, J=15.5 Hz, 1H), 4.75-4.70 (m, 1H), 4.19-4.13 (m, 2H), 3.31-3.20 (m, 3H), 2.98 (br s, 2H), 2.33 (br s, 2H), 2.23 (s, 3H), 2.10 (br s, 2H), 1.89-1.86 (m, 2H), 1.70-1.55 (m, 6H), 1.32-1.10 (m, 6H), 0.91-0.84 (m, 2H). MS: exact mass calculated for C$_{32}$H$_{40}$N$_4$O$_4$, 544.30; m/z found, 545.3 [M+H]$^+$, 567.3 [M+Na]$^+$.

Example 51

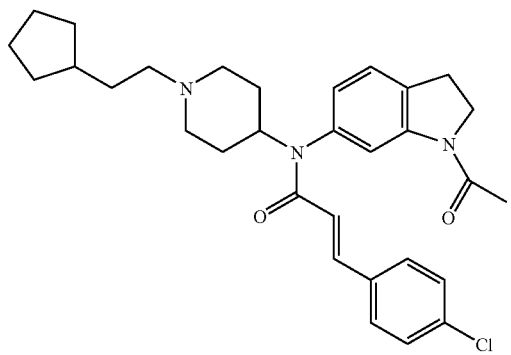

trans-N-(1-Acetyl-2,3-dihydro-1H-indol-6-yl)-3-(4-chloro-phenyl)-N-[1-(2-cyclopentyl-ethyl)-piperidin-4-yl]-acrylamide The title compound (72 mg, 60%) was prepared as in Example 49, using cyclopentyl-acetaldehyde in place of cyclohexyl-acetaldehyde. $^1$H NMR (500 MHz, CDCl$_3$): 8.04 (s, 1H), 7.57 (d, J=15.5 Hz, 1H), 7.23-7.16 (m, 5H), 6.75-6.73 (m, 1H), 6.14 (d, J=15.5 Hz, 1H), 4.75-4.70 (m, 1H), 4.17-4.10 (m, 2H), 3.32-3.22 (m, 2H), 2.98-2.96 (m, 2H), 2.39-2.18 (m, 7H), 2.16-2.09 (m, 2H), 1.92-1.40 (m, 11H), 1.07-1.05 (m, 2H). MS: exact mass calculated for C$_{31}$H$_{38}$ClN$_3$O$_2$, 519.27; m/z found, 520.2 [M+H]$^+$, 522.2 [M+H]$^+$, 543.2 [M+Na]$^+$.

Example 52

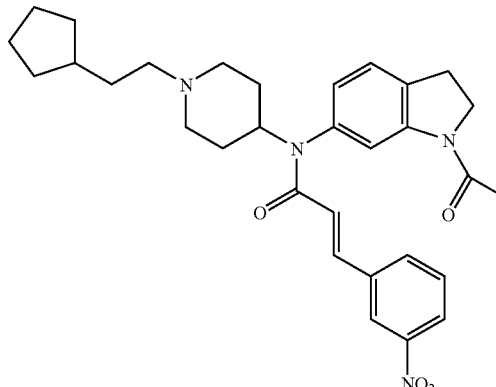

trans-N-(1-Acetyl-2,3-dihydro-1H-indol-6-yl)-N-[1-(2-cyclopentyl-ethyl)-piperidin-4-yl]-3-(3-nitro-phenyl)-acrylamide The title compound (67.1 mg, 55%) was prepared as in Example 50, using cyclopentyl-acetaldehyde in place of cyclohexyl-acetaldehyde. $^1$H NMR (500 MHz, CDCl$_3$): 8.10-8.07 (m, 3H), 7.66 (d, J=15.5 Hz, 1H), 7.59-7.57 (m, 1H), 7.46-7.43 (m, 1H), 7.20-7.19 (m, 1H), 6.77-6.75 (m, 1H), 6.28 (d, J=15.5 Hz, 1H), 4.74-4.71 (m, 1H), 4.19-4.10 (m, 2H), 3.31-3.23 (m, 2H), 2.96-2.94 (m, 2H), 2.31-2.18 (m, 5H), 2.07-2.04 (m, 2H), 1.78-1.44 (m, 13H), 1.07-1.04 (m, 2H). MS: exact mass calculated for C$_{31}$H$_{38}$N$_4$O$_4$, 530.29; m/z found, 531.3 [M+H]$^+$, 553.3 [M+Na]$^+$.

Example 53

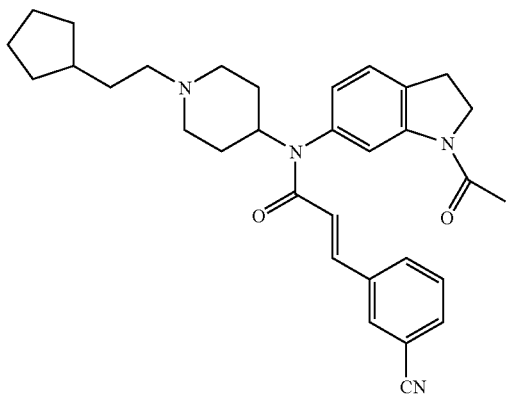

trans-N-(1-Acetyl-2,3-dihydro-1H-indol-6-yl)-3-(3-cyano-phenyl)-N-[1-(2-cyclopentyl-ethyl)-piperidin-4-yl]-acrylamide The title compound (61 mg, 50%) was prepared as in Example 52, using trans-3-(3-cyano-phenyl)-acrylic acid in place of trans-3-(4-chloro-phenyl)-acrylic acid. $^1$H NMR (500 MHz, CDCl$_3$): 8.04 (s, 1H), 7.59 (d, J=15.5 Hz, 1H), 7.53-7.49 (m, 3H), 7.40-7.37 (m, 1H), 7.20-7.19 (m, 1H), 6.78-6.73 (m, 1H), 6.22 (d, J=15.5 Hz, 1H), 4.72 (br s, 1H), 4.22-4.11 (m, 2H), 3.34-3.24 (m, 2H), 2.96 (br s, 1H), 2.30-2.24 (m, 5H), 2.08-1.86 (m, 6H), 1.71-1.44 (m, 10H), 1.07-1.03 (m, 2H). MS: exact mass calculated for C$_{32}$H$_{38}$N$_4$O$_2$, 510.30; m/z found, 511.2 [M+H]$^+$, 533.3 [M+Na]$^+$.

Example 54

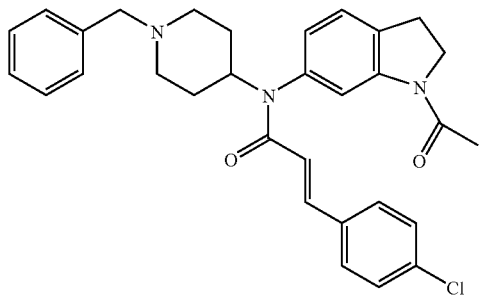

trans-N-(1-Acetyl-2,3-dihydro-1H-indol-6-yl)-N-(1-benzyl-piperidin-4-yl)-3-(4-chloro-phenyl)-acrylamide The title compound (135 mg, 92%) was prepared as in Example 20 using trans-3-(4-chloro-phenyl)-acrylic acid in place of trans-3-thiophen-3-yl-acrylic acid. $^1$H NMR (500 MHz, CDCl$_3$): 8.04 (s, 1H), 7.56 (d, J=15.5 Hz, 1H), 7.31-7.15 (m, 10H), 6.73 (dd, J=8.1, 1.5 Hz, 1H), 6.12 (d, J=15.5 Hz, 1H), 4.75-4.68 (m, 1H), 4.18-4.12 (m, 2H), 3.44 (s, 2H), 3.31-3.22 (m, 2H), 2.91-2.86 (m, 2H), 2.23 (s, 3H), 2.18-2.05 (m, 2H), 1.90-1.70 (m, 2H), 1.60-1.51 (m, 1H), 1.50-1.37 (m, 1H). MS: exact mass calculated for C$_{31}$H$_{32}$ClN$_3$O$_2$, 513.22; m/z found, 514.2 [M+H]$^+$.

Example 55

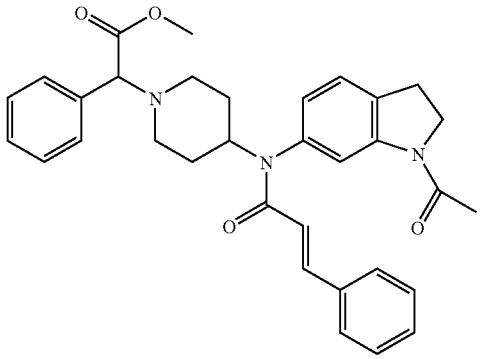

trans-{4-[(1-Acetyl-2,3-dihydro-1H-indol-6-yl)-(3-phenyl-acryloyl)-amino]-piperidin-1-yl}-phenyl-acetic acid methyl ester To a solution of trans-N-(1-acetyl-2,3-dihydro-1H-indol-6-yl)-3-phenyl-N-piperidin-4-yl-acrylamide (Example 41, Step C; 49 mg, 0.13 mmol) in DMF (0.5 mL) and DCM (2 mL) was added Na$_2$CO$_3$ (41 mg, 0.39 mmol) followed by methyl α-bromophenylacetate (26 μL, 0.16 mmol). After stirring overnight, the reaction mixture was poured into H$_2$O and DCM was added. The organic fraction was washed with brine (3×), dried (Na$_2$SO$_4$), and concentrated. Purification by silica gel chromatography (2% methanol (2 M NH$_3$) in DCM) afforded 59 mg (84%) of the title compound. $^1$H NMR (400 MHz, CDCl$_3$): 8.04 (br d, J=12.4 Hz, 1H), 7.62 (d, J=15.4 Hz, 1H), 7.38-7.22 (m, 10H), 7.18 (dd, J=8.8, 8.0 Hz, 1H), 6.73 (dd, J=17.2, 7.8 Hz, 1H), 6.15 (d, J=15.6 Hz, 1H), 4.74 (br dd, J=12.4, 12.1 Hz, 1H), 4.17 (dd, J=8.8, 8.3 Hz, 2H), 3.94 (d, J=3.8 Hz, 1H), 3.65 (s, 3H), 3.31-3.24 (m, 2H), 3.01-2.94 (m, 1H), 2.76-2.69 (m, 1H), 2.34-2.22 (m, 1H), 2.24 (d, J=5.3 Hz, 3H), 2.02-1.76 (m, 2H), 1.76-1.63 (m, 1H), 1.61 (s, 3H), 1.58-1.40 (m, 1H). MS: exact mass calculated for C$_{33}$H$_{35}$N$_3$O$_4$, 537.3; m/z found, 538.5 [M+H]$^+$.

Example 56

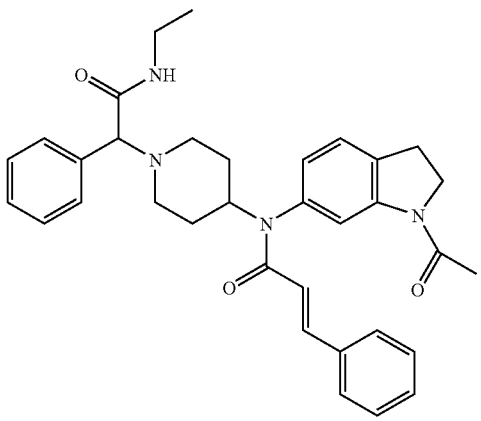

trans-N-(1-Acetyl-2,3-dihydro-1H-indol-6-yl)-N-[1-(ethylcarbamoyl-phenyl-methyl)-piperidin-4-yl]-3-phenyl-acrylamide The title compound (x mg, x%) was prepared from trans-N-(1-acetyl-2,3-dihydro-1H-indol-6-yl)-3-phenyl-N-piperidin-4-yl-acrylamide and 2-bromo-N-ethyl-2-phenyl-acetamide as described in Example 55. After silica gel chromatography, the compound was further purified by reverse-phase HPLC to yield the desired product as its TFA salt. $^1$H NMR (400 MHz, CDCl$_3$): 8.58-8.48 (m, 1H), 8.06-7.91 (m, 1H), 7.57 (d, J=15.6 Hz, 1H), 7.55-7.46 (m, 5H), 7.46-7.34 (m, 1H), 7.34-7.23 (m, 3H), 7.00-6.85 (m, 1H), 6.22 (d, J=15.4 Hz, 1H), 4.47-4.67 (m, 1H), 4.30-4.18 (m, 2H), 3.85-3.68 (m, 1H), 3.37-3.14 (m, 9H), 3.13-3.01 (m, 1H), 2.99-2.84 (m, 1H), 2.25 (br s, 3H), 2.10-1.71 (m, 2H), 1.03 (t, J=7.3 Hz, 3H). MS: exact mass calculated for C$_{34}$H$_{38}$N$_4$O$_3$, 550.3; m/z found, 551.5 [M+H]$^+$.

Assay Methods

Radioligand Binding Assay

KAN-Ts endogenously expressing Y2 receptors were used for the radioligand binding assay. Cells were grown to confluence on 150 cm$^2$ tissue culture plates, washed with phosphate-buffered saline (PBS), and scraped into 50 mL tubes. After centrifugation, the supernatant was aspirated, and the pellets frozen and stored at –80° C. Thawed pellets were homogenized with a polytron tissue grinder for 15 sec in 20 mM Tris-HCl, 5 mM EDTA. The homogenate was centrifuged at 800×g for 5 min and the collected supernatant was recentrifuged at 25000×g for 25 min. The resulting pellet was resuspended in binding buffer (20 mM HEPES, 120 mM NaCl, 0.22 mM KH$_2$PO$_4$, 1.3 mM CaCl$_2$, 0.8 mM MgSO$_4$). Membranes were incubated with [$^{125}$I]PYY (80 pM) in the presence or absence of test compound for 1 h at rt. The reaction was stopped by filtration through GF/C filter plates pre-soaked in 0.3% polyethylenimine and subsequently washed with Tris 50 mM, 5 mM EDTA buffer. Plates were dried for 1 h in a 55° C. oven, scintillation fluid was added and the radioactivity was counted in a Packard TopCount. Specific binding to the NPY receptor subtypes was determined by radioactivity that was bound in the presence of 1 mM NPY. Each binding experiment was repeated three to eight times, each in duplicate. IC$_{50}$ values (i.e. concentration of unlabelled peptide or antagonist required to compete for 50% of specific binding to the radioligand) were calculated using the GraphPad Prism software (GraphPad Software Inc., San Diego Calif.) with a fit to a sigmoidal dose response curve. Data were expressed as pIC$_{50}$ values where pIC$_{50}$=–log IC$_{50}$. Data is presented in Table 1.

TABLE 1

| EX | IC$_{50}$ (μM) |
|---|---|
| 1 | 4.0 |
| 2 | 22 |
| 3 | 3.5 |
| 4 | 4.8 |
| 5 | 4.8 |
| 6 | 5.3 |
| 7 | 15 |
| 8 | 30 |
| 9 | 10 |
| 10 | 30 |
| 11 | 30 |
| 12 | 18 |
| 13 | 11 |
| 14 | 30 |
| 15 | 30 |
| 16 | 9.2 |
| 17 | 22 |
| 18 | 2.8 |
| 19 | 30 |

TABLE 1-continued

| EX | IC$_{50}$ (μM) |
|---|---|
| 20 | 3.2 |
| 21 | 30 |
| 22 | 30 |
| 23 | 12 |
| 24 | 30 |
| 25 | 17 |
| 26 | 2.8 |
| 27 | 8.9 |
| 28 | 30 |
| 29 | 3.3 |
| 30 | 3.6 |
| 31 | 3.0 |
| 32 | 1.4 |
| 33 | 1.9 |
| 34 | 1.0 |
| 35 | 5.8 |
| 36 | 2.5 |
| 37 | 3.9 |
| 38 | 30 |
| 39 | 29 |
| 40 | 26 |
| 41 | 2.3 |
| 42 | 1.1 |
| 43 | 0.6 |
| 44 | 0.8 |
| 45 | 16 |
| 46 | 18 |
| 47 | 12 |
| 48 | 12 |
| 49 | 1.1 |
| 50 | 0.5 |
| 51 | 1.1 |
| 52 | 0.35 |
| 53 | 0.1 |
| 54 | 3.6 |
| 55 | 6.3 |
| 56 | 30 |

[$^{35}$S] GTPγS Binding Assay in KAN-Ts Cells

Membranes from KAN-Ts cells were prepared as described above. Membranes were thawed on ice and diluted in 50 mM Tris-HCl buffer, pH 7.4 containing 10 mM MgC$_2$, 1 mM EDTA, 100 mM NaCl, 5 mM GDP, 0.25% BSA. Assay mixtures (150 mL) were preincubated with compounds for 30 min at rt. Then, 50 mL of [$^{35}$S]GTPγS in assay buffer was added to a final concentration of 200 pM and the assay mixtures were incubated for 1 h at rt. Reactions were terminated by rapid filtration thought GF/C filters. Filters were washes twice with ice cold 50 mM Tris-HCl, pH 7.4 containing 10 mM MgCl$_2$. Basal [$^{35}$S]GTPγS was measured in the absence of compounds. In initial experiments, non-specific binding was measured in the presence of 100 mM GTPγS. This nonspecific binding never exceeded 10% of basal binding and was thus not subtracted from experimental data. Stimulation of [$^{35}$S]GTPγS is presented as percentage over basal and was calculated as one hundred times the difference between stimulated and basal binding (in cpm). Agonist concentration-response curves for increases in [$^{35}$S]GTPγS binding and antagonist inhibition curves for inhibition of PYY (300 nM)-stimulated [$^{35}$S]GTPγS binding were analyzed by non-linear regression using GraphPad Prism software (GraphPad Software Inc., San Diego Calif.). EC$_{50}$ (concentration of compound at which 50% of its own maximal stimulation is obtained) and IC$_{50}$ (concentration of its own maximal inhibition of PYY-stimulated [$^{35}$S]GTPγS binding is obtained) were derived from the curves. IC$_{50}$ values were corrected as follows: corrected IC$_{50}$(IC$_{50}$corr)= IC$_{50}$/(1+[PYY]/EC$_{50}$(PYY)) and pIC$_{50}$corr=–log IC$_{50}$corr.

The title compound of Example 53 was demonstrated to be a competitive in this assay (pIC$_{50}$=7.20).

What is claimed is:

1. A compound of the formula:

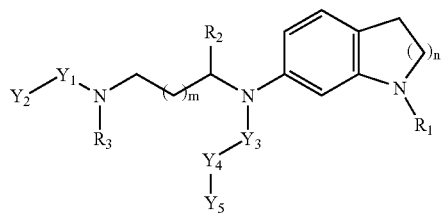
(I)

wherein the fused pyrrolidine ring optionally contains a single carbon-carbon double bond or a single carbon ring member adjacent to the nitrogen is optionally =O substituted;

n is 1 or 2;

m is 0, 1, or 2;

$Y_1$ is a $C_{0-5}$ alkylene, $C_{0-5}$ alkenylene, $C_{0-5}$ alkynylene, $C_{0-5}$acylene; —CH(CONR$^f$R$^g$)— (where R$^f$ and R$^g$ are independently H or $C_{1-4}$alkyl), or —CH(CO$_2$C$_{1-4}$ alkyl)—;

$Y_2$ is H, phenyl, $C_{4-8}$ cycloalkyl or $C_{4-8}$ cycloalkenyl, each ring optionally substituted with R$^q$;

$Y_3$ is —CH$_2$—, carbonyl or sulfone;

$Y_4$ is a substituted or unsubstituted $C_{2-7}$ alkyl, $C_{2-7}$ alkenyl, $C_{2-7}$ alkynyl or $C_{3-7}$cycloalkyl;

$Y_5$ is phenyl, furanyl, thiophenyl, pyrrolyl, pyrrolinyl, pyrrolidinyl, dioxolanyl, oxazolyl, thiazolyl, imidazolyl, imidazolidinyl, pyrazolyl, pyrazolinyl, pyrazolidinyl, oxadiazolyl, triazolyl, thiadiazolyl, pyranyl, pyridyl, piperidinyl, dioxanyl, morpholinyl, dithianyl, thiomorpholinyl, pyridazinyl, pyrimidinyl, pyrazinyl, piperazinyl, naphthalenyl, quinolonyl, purinyl, indolyl, benzofuranyl, or benzothiophenyl, each optionally mono-, di- or tri-substituted with R$^q$;

$R_1$ is H or is

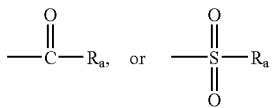

where $R_a$ is H, a substituted or unsubstituted $C_{1-5}$ alkyl, $C_{1-5}$ alkenyl, $C_{1-5}$ alkynyl or $C_{1-5}$ acyl, where the substituent is $C_{1-4}$alkoxy or one or more fluoro;

$R_2$ and $R_3$ are independently selected from H, a substituted or unsubstituted $C_{1-5}$ alkyl, $C_{1-5}$ alkenyl, or $C_{1-5}$ alkynyl, or $R_2$ and $R_3$ may be taken together with the nitrogen of $R_3$ attachment to form piperidine or pyrrolidine or azepine; and $R^q$ is selected from the group consisting of —OH, —$C_{1-6}$ alkyl, —O$C_{1-6}$ alkyl, Ph—, —OPh, benzyl, —Obenzyl, —$C_{3-6}$ cycloalkyl, —O$C_{3-6}$ cycloalkyl, —CN, —NO$_2$, —N(R$^y$)R$^z$ (wherein R$^y$ and R$^z$ are independently selected from H, $C_{1-6}$ alkyl, $C_{1-6}$ alkenyl, or R$^y$ and R$^z$ may be taken together with the nitrogen of attachment to form an otherwise aliphatic hydrocarbon ring, said ring having 4 to 7 members, optionally having one carbon replaced with O, =N—, NH or N(C$_{1-4}$alkyl), optionally having one carbon substituted with —OH, and optionally having one or two unsaturated bonds in the ring), —(C=O)N(R$^y$)R$^z$, —(N—R$^t$)COR$^t$, —(N—R$_l^t$)SO$_2$C$_{1-6}$alkyl (wherein R$^t$ is H or C$_{1-6}$alkyl or two R$^t$ in the same substituent may be taken together with the amide of attachment to form an otherwise aliphatic hydrocarbon ring, said ring having 4 to 6 members), —(C=O)C$_{1-6}$alkyl, —(S=(O)$_n$)—C$_{1-6}$alkyl (wherein n is selected from 0, 1 or 2), —SO$_2$N(R$^y$)R$^z$, —SCF$_3$, halo, —CF$_3$, —OCF$_3$, —COOH and —COOC$_{1-6}$ alkyl;

and enantiomers, diastereomers, hydrates, solvates and pharmaceutically acceptable salts, esters and amides thereof, with the proviso that the compound of formula (I) cannot include a compound of the formula:

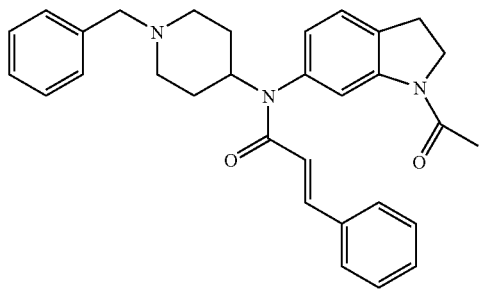

2. A compound of claim 1 of the formula:

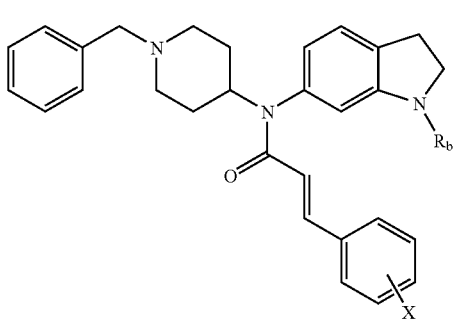
(II)

where $R_b$ is H, COCH$_3$, CHO, COCH$_2$COCH$_3$, COCO$_2$C$_2$H$_5$, CH$_3$, SO$_2$CH$_3$, or COCF$_3$ and X is 4-CF$_3$, 3-CF$_3$, 2-CF$_3$, 3-Br, 3-F, 3-Cl, 3-CH$_3$, 3-NO$_2$, 3-CN, 3-SOCF$_3$, 3,5-diF, 3,5-diCH$_3$, 3,5-diCl, or 4-Cl;

and enantiomers, diastereomers, hydrates, solvates and pharmaceutically acceptable salts, esters and amides thereof.

3. A compound of claim 1 of the formula:

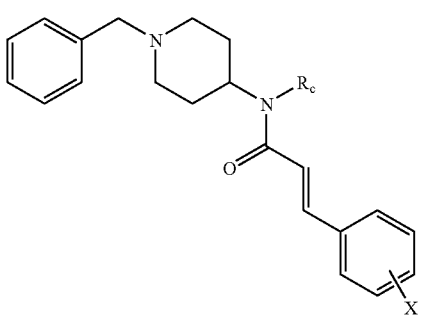
(III)

where $R_c$ is N-(1-acetyl)-tetrahydroquinolin-7-yl, 2-oxo-2,3-dihydro-1H-indol-6-yl, or N-(1-acetyl)-1H-indol-6-yl and X is 4-CF$_3$, 3-CF$_3$, 2-CF$_3$, 3-Br, 3-Cl, 3-CH$_3$, 3-NO$_2$, 3-CN, 3-SOCF$_3$, 3,5-diF, 3,5-diCH$_3$, 3,5-diCl, or 4-Cl;

and enantiomers, diastereomers, hydrates, solvates and pharmaceutically acceptable salts, esters and amides thereof.

4. A compound of claim 1 of the formula:

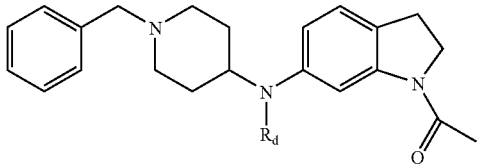
(IV)

where $R_d$ is $COCH_2CH_2C_6H_4X$, $CO(C_3H_4)C_6H_4X$, E-$CH_2CH=CHC_6H_4X$, E-$SO_2CH=CHC_6H_4X$, $COC\equiv CC_6H_4X$, Z-$COCH=CHC_6H_4X$, (E,E)—CO$(CH=CH)_2C_6H_5$, $CH=CH_2$, E-COCH=CH(3-thiophenyl)X, E-COCH=CH(pyridyl)X, E-COCH=CH(1-hydroxy-pyridyl), or E-COCH=CH(2-imidazolyl)X and X is 4-$CF_3$, 3-$CF_3$, 2-$CF_3$, 3-Br, 3-F, 3-Cl, 3-$CH_3$, 3-$NO_2$, 3-CN, 3-$SOCF_3$, 3,5-diF, 3,5-di$CH_3$, 3,5-diCl, or 4-Cl;

and enantiomers, diastereomers, hydrates, solvates and pharmaceutically acceptable salts, esters and amides thereof.

5. A compound of claim 1 of the formula:

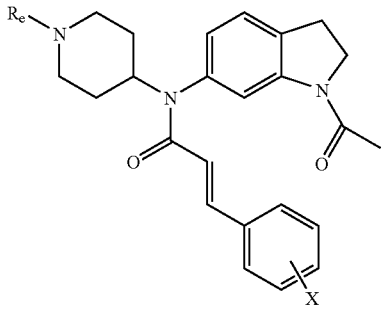
(V)

where $R_e$ is $COC_6H_5$, $CH_2CH_2C_6H_5$, $CH_2CH_2CH_2C_6H_5$, $CH(CO_2CH_3)C_6H_5$, $CH(CONHCH_2CH_3)C_6H_5$, $CH_2C_6H_{11}$, $CH_2CH_2C_6H_{11}$, or $CH_2CH_2C_5H_9$, and X is 4-$CF_3$, 3-$CF_3$, 2-$CF_3$, 3-Br, 3-F, 3-Cl, 3-$CH_3$, 3-$NO_2$, 3-CN, 3$SOCF_3$, 3,5-diF, 3,5-di$CH_3$, 3,5-diCl, or 4-Cl;

and enantiomers, diastereomers, hydrates, solvates and pharmaceutically acceptable salts, esters and amides thereof.

6. A compound of claim 1 of the formula:

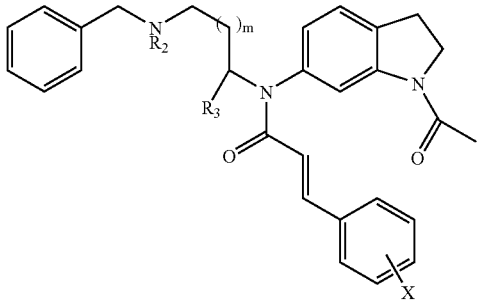
(VI)

where $R_2$ is H, $C_{1-3}$alkyl, or allyl and $R_3$ is H, or $R_2$ and $R_3$ are taken together to be a divalent moiety —$CH_2$—, m is 1 or 2, and X is 4-$CF_3$, 3-$CF_3$, 2-$CF_3$, 3-Br, 3-F, 3-Cl, 3-$CH_3$, 3-$NO_2$, 3-CN, 3-$SOCF_3$, 3,5-diF, 3,5-di$CH_3$, 3,5-diCl, or 4-Cl;

and enantiomers, diastereomers, hydrates, solvates and pharmaceutically acceptable salts, esters and amides thereof.

7. The compound of claim 1 wherein said pharmaceutically acceptable salt is an effective amino addition salt.

8. The compound of claim 1 wherein said pharmaceutically acceptable salt is selected from the group consisting of hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, saccharate, ethanesulfonate, benzenesulfonate, pamoate [i.e., 1,1'-methylene-bis-(2-hydroxy-3 naphthoate)] and laurylsulfonate.

9. A compound of claim 1, selected from the group consisting of:
trans-N-(1-Benzyl-piperidin-4-yl)-N-(2,3-dihydro-1H-indol-6-yl)-3-phenyl-acrylamide;
trans-N-(1-Benzyl-piperidin-4-yl)-N-(1-formyl-2,3-dihydro-1H-indol-6-yl)-3-phenyl-acrylamide;
trans-N-(1-Benzyl-piperidin-4-yl)-N-[1-(3-oxo-butyryl)-2,3-dihydro-1H-indol-6-yl]-3-phenyl-acrylamide;
trans-{6-[(1-Benzyl-piperidin-4-yl)-(3-phenyl-acryloyl)-amino]-2,3-dihydro-indol-1-yl}-oxo-acetic acid ethyl ester;
trans-N-(1-Benzyl-piperidin-4-yl)-N-(1-methyl-2,3-dihydro-1H-indol-6-yl)-3-phenyl-acrylamide;
trans-N-(1-Benzyl-piperidin-4-yl)-N-(1-methanesulfonyl-2,3-dihydro-1H-indol-6-yl)-3-phenyl-acrylamide;
trans-N-(1-Benzyl-piperidin-4-yl)-3-phenyl-N-[1-(2,2,2-trifluoro-acetyl)-2,3-dihydro-1H-indol-6-yl]-acrylamide;
trans-N-(1-Acetyl-1,2,3,4-tetrahydro-quinolin-7-yl)-N-(1-benzyl-piperidin-4-yl)-3-phenyl-acrylamide;
trans-N-(1-Benzyl-piperidin-4-yl)-N-(2-oxo-2,3-dihydro-1H-indol-6-yl)-3-phenyl-acrylamide;
trans-N-(1-Acetyl-1H-indol-6-yl)-N-(1-benzyl-piperidin-4-yl)-3-phenyl-acrylamide;
N-(1-Acetyl-2,3-dihydro-1H-indol-6-yl)-N-(1-benzyl-piperidin-4-yl)-3-phenyl-propionamide;
trans-2-Phenyl-cyclopropanecarboxylic acid (1-acetyl-2,3-dihydro-1H-indol-6-yl)-(1-benzyl-piperidin-4-yl)-amide;
trans-1-{6-[(1-Benzyl-piperidin-4-yl)-(3-phenyl-allyl)-amino]-2,3-dihydro-indol-1-yl}-ethanone;
trans-2-Phenyl-ethenesulfonic acid (1-acetyl-2,3-dihydro-1H-indol-6-yl)-(1-benzyl-piperidin-4-yl)-amide;
3-Phenyl-propynoic acid (1-acetyl-2,3-dihydro-1H-indol-6-yl)-(1-benzyl-piperidin-4-yl)-amide;
cis-N-(1-Acetyl-2,3-dihydro-1H-indol-6-yl)-N-(1-benzyl-piperidin-4-yl)-3-phenyl-acrylamide;
trans,trans-5-Phenyl-penta-2,4-dienoic acid (1-acetyl-2,3-dihydro-1H-indol-6-yl)-(1-benzyl-piperidin-4-yl)-amide;
N-(1-Acetyl-2,3-dihydro-1H-indol-6-yl)-N-(1-benzyl-piperidin-4-yl)-acrylamide;
trans-N-(1-Acetyl-2,3-dihydro-1H-indol-6-yl)-N-(1-benzyl-piperidin-4-yl)-3-thiophen-3-yl-acrylamide;
trans-N-(1-Acetyl-2,3-dihydro-1H-indol-6-yl)-N-(1-benzyl-piperidin-4-yl)-3-pyridin-2-yl-acrylamide;
trans-N-(1-Acetyl-2,3-dihydro-1H-indol-6-yl)-N-(1-benzyl-piperidin-4-yl)-3-pyridin-3-yl-acrylamide;
trans-N-(1-Acetyl-2,3-dihydro-1H-indol-6-yl)-N-(1-benzyl-piperidin-4-yl)-3-pyridin-4-yl-acrylamide;

trans-N-(1-Acetyl-2,3-dihydro-1H-indol-6-yl)-N-(1-benzyl-piperidin-4-yl)-3-(1-oxy-pyridin-4-yl)-acrylamide;
trans-N-(1-Acetyl-2,3-dihydro-1H-indol-6-yl)-N-(1-benzyl-piperidin-4-yl)-3-(1H-imidazol-2-yl)-acrylamide;
trans-N-(1-Acetyl-2,3-dihydro-1H-indol-6-yl)-N-(1-benzyl-piperidin-4-yl)-3-(4-trifluoromethyl-phenyl)-acrylamide;
trans-N-(1-Acetyl-2,3-dihydro-1H-indol-6-yl)-N-(1-benzyl-piperidin-4-yl)-3-(3-trifluoromethyl-phenyl)-acrylamide;
trans-N-(1-Acetyl-2,3-dihydro-1H-indol-6-yl)-N-(1-benzyl-piperidin-4-yl)-3-(2-trifluoromethyl-phenyl)-acrylamide;
trans-N-(1-Acetyl-2,3-dihydro-1H-indol-6-yl)-N-(1-benzyl-piperidin-4-yl)-3-(3-bromo-phenyl)-acrylamide;
trans-N-(1-Acetyl-2,3-dihydro-1H-indol-6-yl)-N-(1-benzyl-piperidin-4-yl)-3-(3-fluoro-phenyl)-acrylamide;
trans-N-(1-Acetyl-2,3-dihydro-1H-indol-6-yl)-N-(1-benzyl-piperidin-4-yl)-3-(3-chloro-phenyl)-acrylamide;
trans-N-(1-Acetyl-2,3-dihydro-1H-indol-6-yl)-N-(1-benzyl-piperidin-4-yl)-3-m-tolyl-acrylamide;
trans-N-(1-Acetyl-2,3-dihydro-1H-indol-6-yl)-N-(1-benzyl-piperidin-4-yl)-3-(3-nitro-phenyl)-acrylamide;
trans-N-(1-Acetyl-2,3-dihydro-1H-indol-6-yl)-N-(1-benzyl-piperidin-4-yl)-3-(3-cyano-phenyl)-acrylamide;
trans-N-(1-Acetyl-2,3-dihydro-1H-indol-6-yl)-N-(1-benzyl-piperidin-4-yl)-3-(3-trifluoromethanesulfinyl-phenyl)-acrylamide;
trans-N-(1-Acetyl-2,3-dihydro-1H-indol-6-yl)-N-(1-benzyl-piperidin-4-yl)-3-(3,5-difluoro-phenyl)-acrylamide;
trans-N-(1-Acetyl-2,3-dihydro-1H-indol-6-yl)-N-(1-benzyl-piperidin-4-yl)-3-(3,5-dimethyl-phenyl)-acrylamide;
trans-N-(1-Acetyl-2,3-dihydro-1H-indol-6-yl)-N-(1-benzyl-piperidin-4-yl)-3-(3,5-dichloro-phenyl)-acrylamide;
trans-N-(1-Acetyl-2,3-dihydro-1H-indol-6-yl)-N-(1-benzoyl-piperidin-4-yl)-3-phenyl-acrylamide;
trans-N-(1-Acetyl-2,3-dihydro-1H-indol-6-yl)-N-(1-phenethyl-piperidin-4-yl)-3-phenyl-acrylamide;
trans-N-(1-Acetyl-2,3-dihydro-1H-indol-6-yl)-3-phenyl-N-[1-(3-phenyl-propyl)-piperidin-4-yl]-acrylamide;
trans-N-(1-Acetyl-2,3-dihydro-1H-indol-6-yl)-N-(1-cyclohexylmethyl-piperidin-4-yl)-3-phenyl-acrylamide;
trans-N-(1-Acetyl-2,3-dihydro-1H-indol-6-yl)-N-[1-(2-cyclohexyl-ethyl)-piperidin-4-yl]-3-phenyl-acrylamide;
trans-N-(1-Acetyl-2,3-dihydro-1H-indol-6-yl)-N-[1-(2-cyclopentyl-ethyl)-piperidin-4-yl]-3-phenyl-acrylamide;
trans-N-(1-Acetyl-2,3-dihydro-1H-indol-6-yl)-N-(1-benzyl-piperidin-3-yl)-3-phenyl-acrylamide;
trans-N-(1-Acetyl-2,3-dihydro-1H-indol-6-yl)-N-(1-benzyl-pyrrolidin-3-yl)-3-phenyl-acrylamide;
trans-N-(1-Acetyl-2,3-dihydro-1H-indol-6-yl)-N-(3-benzylamino-propyl)-3-phenyl-acrylamide;
trans-N-(1-Acetyl-2,3-dihydro-1H-indol-6-yl)-N-[3-(allyl-benzyl-amino)-propyl]-3-phenyl-acrylamide;
trans-N-(1-Acetyl-2,3-dihydro-1H-indol-6-yl)-3-(4-chloro-phenyl)-N-[1-(2-cyclohexyl-ethyl)-piperidin-4-yl]-acrylamide;
trans-N-(1-Acetyl-2,3-dihydro-1H-indol-6-yl)-N-[1-(2-cyclohexyl-ethyl)-piperidin-4-yl]-3-(3-nitro-phenyl)-acrylamide;
trans-N-(1-Acetyl-2,3-dihydro-1H-indol-6-yl)-3-(4-chloro-phenyl)-N-[1-(2-cyclopentyl-ethyl)-piperidin-4-yl]-acrylamide;
trans-N-(1-Acetyl-2,3-dihydro-1H-indol-6-yl)-N-[1-(2-cyclopentyl-ethyl)-piperidin-4-yl]-3-(3-nitro-phenyl)-acrylamide;
trans-N-(1-Acetyl-2,3-dihydro-1H-indol-6-yl)-3-(3-cyano-phenyl)-N-[1-(2-cyclopentyl-ethyl)-piperidin-4-yl]-acrylamide;
trans-N-(1-Acetyl-2,3-dihydro-1H-indol-6-yl)-N-(1-benzyl-piperidin-4-yl)-3-(4-chloro-phenyl)-acrylamide;
trans-{4-[(1-Acetyl-2,3-dihydro-1H-indol-6-yl)-(3-phenyl-acryloyl)-amino]-piperidin-1-yl}-phenyl-acetic acid methyl ester; and
trans-N-(1-Acetyl-2,3-dihydro-1H-indol-6-yl)-N-[1-(ethylcarbamoyl-phenyl-methyl)-piperidin-4-yl]-3-phenyl-acrylamide.

10. A pharmaceutical composition comprising a pharmaceutically acceptable carrier and a therapeutically effective amount of compound of formula (I):

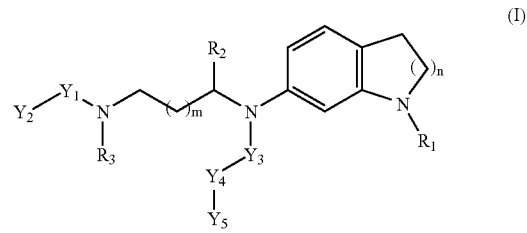

wherein
the fused pyrrolidine ring optionally contains a single carbon-carbon double bond or a single carbon ring member adjacent to the nitrogen is optionally =O substituted;
n is 1 or 2;
m is 0, 1, or 2;
$Y_1$ is a $C_{0-5}$ alkylene, $C_{0-5}$ alkenylene, $C_{0-5}$ alkynylene, $C_{0-5}$ acylene; —CH(CONR$^f$R$^g$)— (where R$^f$ and R$^g$ are independently H or $C_{1-4}$ alkyl), or —CH(CO$_2$C$_{1-4}$ alkyl)—;
$Y_2$ is H, phenyl, $C_{4-8}$ cycloalkyl or $C_{4-8}$ cycloalkenyl, each ring optionally substituted with R$^q$;
$Y_3$ is —CH$_2$—, carbonyl or sulfone;
$Y_4$ is a substituted or unsubstituted $C_{2-7}$ alkyl, $C_{2-7}$ alkenyl, $C_{2-7}$ alkynyl or $C_{3-7}$ cycloalkyl;
$Y_5$ is phenyl, furanyl, thiophenyl, pyrrolyl, pyrrolinyl, pyrrolidinyl, dioxolanyl, oxazolyl, thiazolyl, imidazolyl, imidazolidinyl, pyrazolyl, pyrazolinyl, pyrazolidinyl, oxadiazolyl, triazolyl, thiadiazolyl, pyranyl, pyridyl, piperidinyl, dioxanyl, morpholinyl, dithianyl, thiomorpholinyl, pyridazinyl, pyrimidinyl, pyrazinyl, piperazinyl, naphthalenyl, quinolonyl, purinyl, indolyl, benzofuranyl, or benzothiophenyl, each optionally mono-, di- or tri-substituted with R$^q$;
$R_1$ is H or is

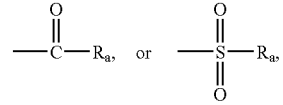

where $R_a$ is H, a substituted or unsubstituted $C_{1-5}$ alkyl, $C_{1-5}$ alkenyl, $C_{1-5}$ alkynyl or $C_{1-5}$ acyl, where the substituent is $C_{1-4}$ alkoxy or one or more fluoro;

$R_2$ and $R_3$ are independently selected from H, a substituted or unsubstituted $C_{1-5}$ alkyl, $C_{1-5}$ alkenyl, or $C_{1-5}$ alkynyl, or $R_2$ and $R_3$ may be taken together with the nitrogen of $R_3$ attachment to form piperidine or pyrrolidine or azepanyl; and $R^q$ is selected from the group consisting of —OH, —$C_{1-6}$ alkyl, —$OC_{1-6}$ alkyl, Ph—, —OPh, benzyl, —Obenzyl, —$C_{3-6}$ cycloalkyl, —$OC_{3-6}$ cycloalkyl, —CN, —$NO_2$, —N($R^y$)$R^z$ (wherein $R^y$ and $R^z$ are independently selected from H, $C_{1-6}$ alkyl, $C_{1-6}$ alkenyl, or $R^y$ and $R^z$ may be taken together with the nitrogen of attachment to form an otherwise aliphatic hydrocarbon ring, said ring having 4 to 7 members, optionally having one carbon replaced with O, =N—, NH or N($C_{1-4}$alkyl), optionally having one carbon substituted with —OH, and optionally having one or two unsaturated bonds in the ring), —(C=O)N($R^y$)$R^z$, —(N—$R^r$)COR$^r$, —(N—$R^r$)$SO_2C_{1-6}$alkyl (wherein $R^r$ is H or $C_{1-6}$alkyl or two $R^r$ in the same substituent may be taken together with the amide of attachment to form an otherwise aliphatic hydrocarbon ring, said ring having 4 to 6 members), —(C=O)$C_{1-6}$alkyl, —(S=(O)$_n$)—$C_{1-6}$alkyl (wherein n is selected from 0, 1 or 2), —$SO_2N(R^y)R^z$, —$SCF_3$, halo, —$CF_3$, —$OCF_3$, —COOH and —$COOC_{1-6}$ alkyl;

and enantiomers, diastereomers, hydrates, solvates and pharmaceutically acceptable salts, esters and amides thereof, with the proviso that the compound of the formula (I) cannot include a compound of the formula:

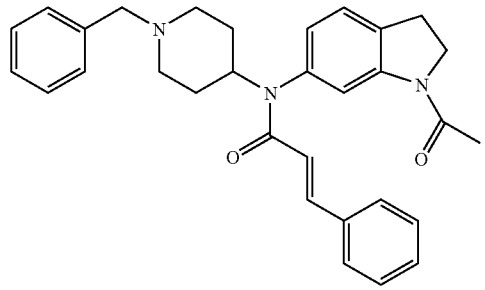

* * * * *